(12) United States Patent
Li et al.

(10) Patent No.: US 12,215,150 B2
(45) Date of Patent: Feb. 4, 2025

(54) ANTI-SLC34A2 MONOCLONAL ANTIBODIES AND USES THEREOF

(71) Applicant: LANOVA MEDICINES DEVELOPMENT CO., LTD., Shanghai (CN)

(72) Inventors: Runsheng Li, Shanghai (CN); Wentao Huang, Shanghai (CN); Yifan Li, Shanghai (CN)

(73) Assignee: LANOVA MEDICINES DEVELOPMENT CO., LTD., Shanghai (CN)

( * ) Notice: Subject to any disclaimer, the term of this patent is extended or adjusted under 35 U.S.C. 154(b) by 0 days.

(21) Appl. No.: 18/656,092

(22) Filed: May 6, 2024

(65) Prior Publication Data

US 2024/0301052 A1    Sep. 12, 2024

Related U.S. Application Data

(63) Continuation of application No. PCT/CN2023/101761, filed on Jun. 21, 2023.

(30) Foreign Application Priority Data

Jun. 22, 2022 (WO) ............... PCT/CN2022/100315

(51) Int. Cl.
*C07K 16/28* (2006.01)
*A61K 39/00* (2006.01)
*A61P 35/00* (2006.01)

(52) U.S. Cl.
CPC ............. *C07K 16/28* (2013.01); *A61P 35/00* (2018.01); *A61K 2039/505* (2013.01); *C07K 2317/565* (2013.01)

(58) Field of Classification Search
None
See application file for complete search history.

(56) References Cited

U.S. PATENT DOCUMENTS

2011/0129483 A1    6/2011 Ritter et al.

FOREIGN PATENT DOCUMENTS

WO    2009097128 A1    8/2009

OTHER PUBLICATIONS

International Search Report for PCT International Application No. PCT/CN2023/101761, dated Aug. 23, 2023, 5 pages.
Written Opinion of the International Searching Authority for PCT International Application No. PCT/CN2023/101761, dated Aug. 23, 2023, 4 pages.

*Primary Examiner* — Ruixiang Li
(74) *Attorney, Agent, or Firm* — Sheppard Mullin Richter & Hampton LLP

(57) ABSTRACT

Provided are antibodies or fragment thereof having binding specificity to the human solute carrier 34 A2 (SLC34A2) protein. These antibodies are capable of binding to SLC34A2 at high affinity and can mediate antibody-dependent cellular cytotoxicity (ADCC) and effectively induce endocytosis. Also provided are methods and uses for treating cancers.

17 Claims, 34 Drawing Sheets

Specification includes a Sequence Listing.

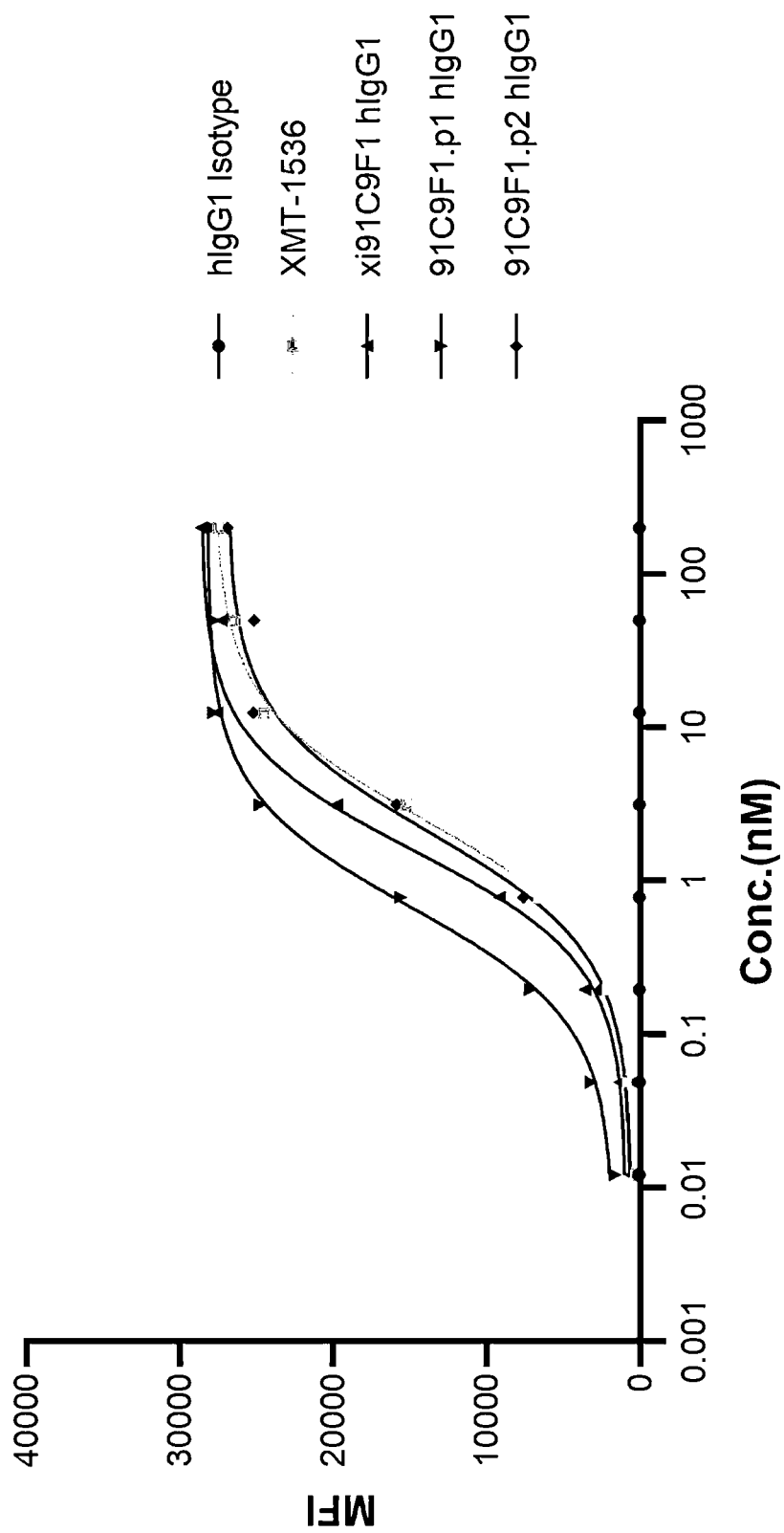

ANTI-SLC34A2 MONOCLONAL ANTIBODIES AND USES THEREOF

CROSS REFERENCE TO RELATED APPLICATIONS

The present application is a continuation of International Application No. PCT/CN2023/101761, filed Jun. 21, 2023, which claims priority to International Application No. PCT/CN2022/100315, filed Jun. 22, 2022, the content of each of which is incorporated herein by reference in its entirety in the present disclosure.

REFERENCE TO AN ELECTRONIC SEQUENCE LISTING

The content of the electronic sequence listing (351805.xml; Size: 105,368 bytes; and Date of Creation: Jun. 8, 2023) is herein incorporated by reference in its entirety.

BACKGROUND

Cell membrane transporter proteins such as transporters belonging to glucose transporter GLUT, ATP-binding cassette transporter ABC, and solute carrier transporter SLC families are frequently upregulated on cancer cells, compared to adjacent normal cells. High levels of transporters are found in a wide range of solid tumors, correlating with poor survival. One of the potential molecular tumor markers may be the sodium-dependent phosphate transporter NaPi2b encoded by the SLC34A2 (Solute carrier 34 A2) gene.

SLC34A2 encodes the type II Na/Pi co-transporter (NaPi2b) which is a multi-transmembrane sodium-dependent phosphate transporter responsible for transcellular inorganic phosphate absorption. NaPi2b is highly abundant in the brush-border membrane of the small intestine, where it is involved in the transcellular flux of inorganic phosphates via the apical membrane of epithelial cells. An altered expression of sodium-dependent phosphate transporter NaPi2b has been reported in ovarian cancer, lung cancer, gastric cancer, thyroid cancer, and other cancers.

Currently, NaPi2b is a target for therapeutic antibodies XMT-1536 and RG-7599, which are in clinical trials for the treatment of ovarian and lung cancers. There is a need to develop more efficacious and safer clinical candidates targeting this protein.

SUMMARY

Anti-SLC34A2 antibodies are discovered herein that have high binding affinity to the human SLC34A2 protein and are efficient in mediating antibody-dependent cellular cytotoxicity (ADCC), and inducing cytotoxicity. When compared to two benchmark antibodies, XMT-1536 and RG-7599, the instantly discovered antibodies exhibited higher general binding affinity, much improved cross-species reactivity, more potent ADCC and cytotoxicity. These antibodies, therefore, can be suitably used for treating diseases such as cancer.

In one embodiment, an antibody or fragment thereof is provided that has specificity to the human SLC34A2 protein. In some embodiments, the antibody or fragment thereof comprises a heavy chain variable region comprising heavy chain complementarity determining regions CDRH1, CDRH2, and CDRH3 and a light chain variable region light chain comprising complementarity determining regions CDRL1, CDRL2, and CDRL3.

Also provided, in some embodiments, are polynucleotides encoding the antibody or fragment, and compositions comprising the antibody or fragment thereof and a pharmaceutically acceptable carrier.

Methods and uses for the treatment of diseases and conditions are also provided. In one embodiment, provided is a method of treating cancer in a patient in need thereof, comprising administering to the patient the antibody or fragment thereof of the present disclosure.

BRIEF DESCRIPTION OF THE DRAWINGS

FIG. 9A-C show the binding activity of the PTM-derisked antibodies to HEC293 cells expressing human SLC34A2.

DETAILED DESCRIPTION

Definitions

Figure 1A:
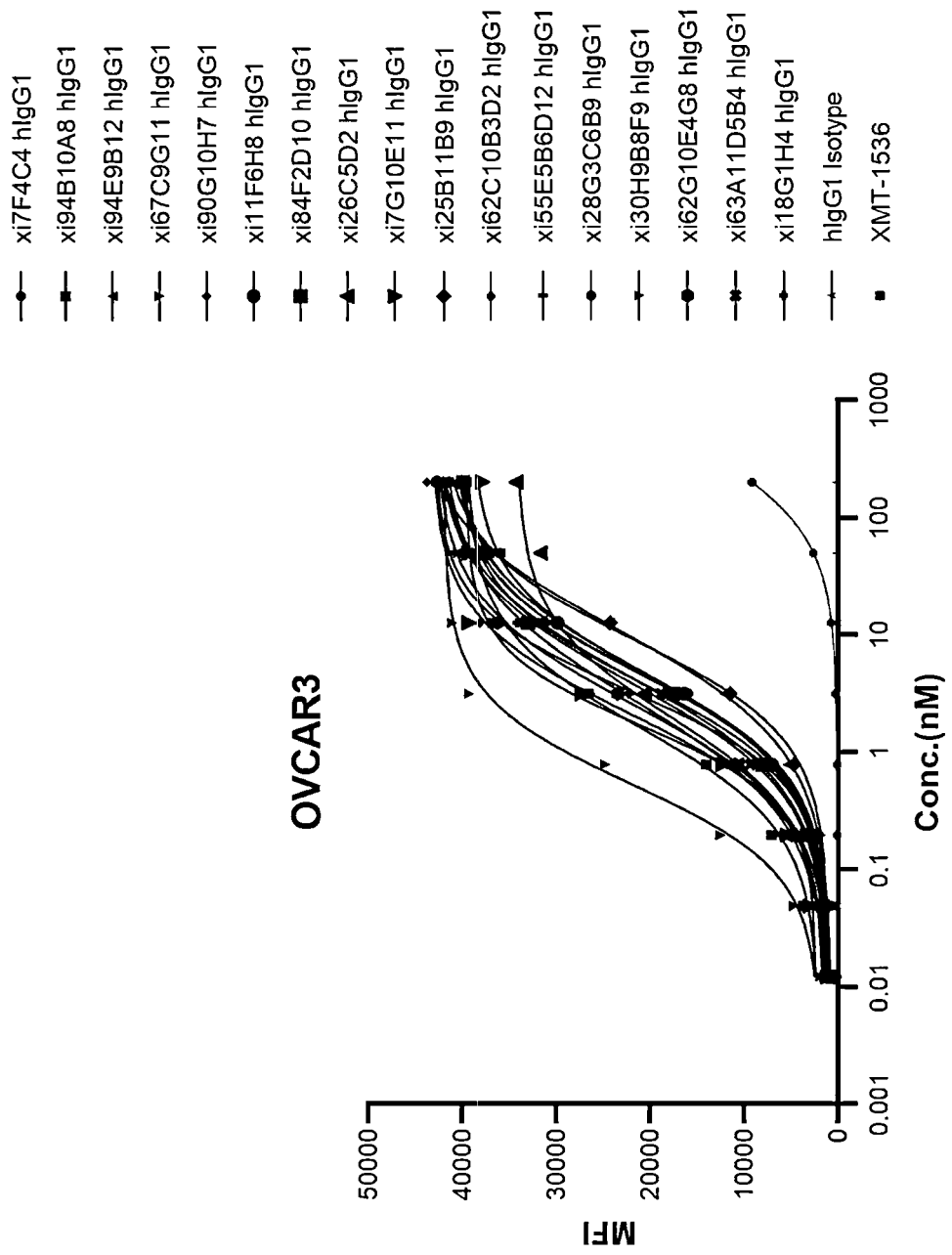
FIG. 1A-B show the binding affinity of the chimeric antibodies to endogenously expressed SLC34A2 on OVCAR3 cells.
Figure 1B:
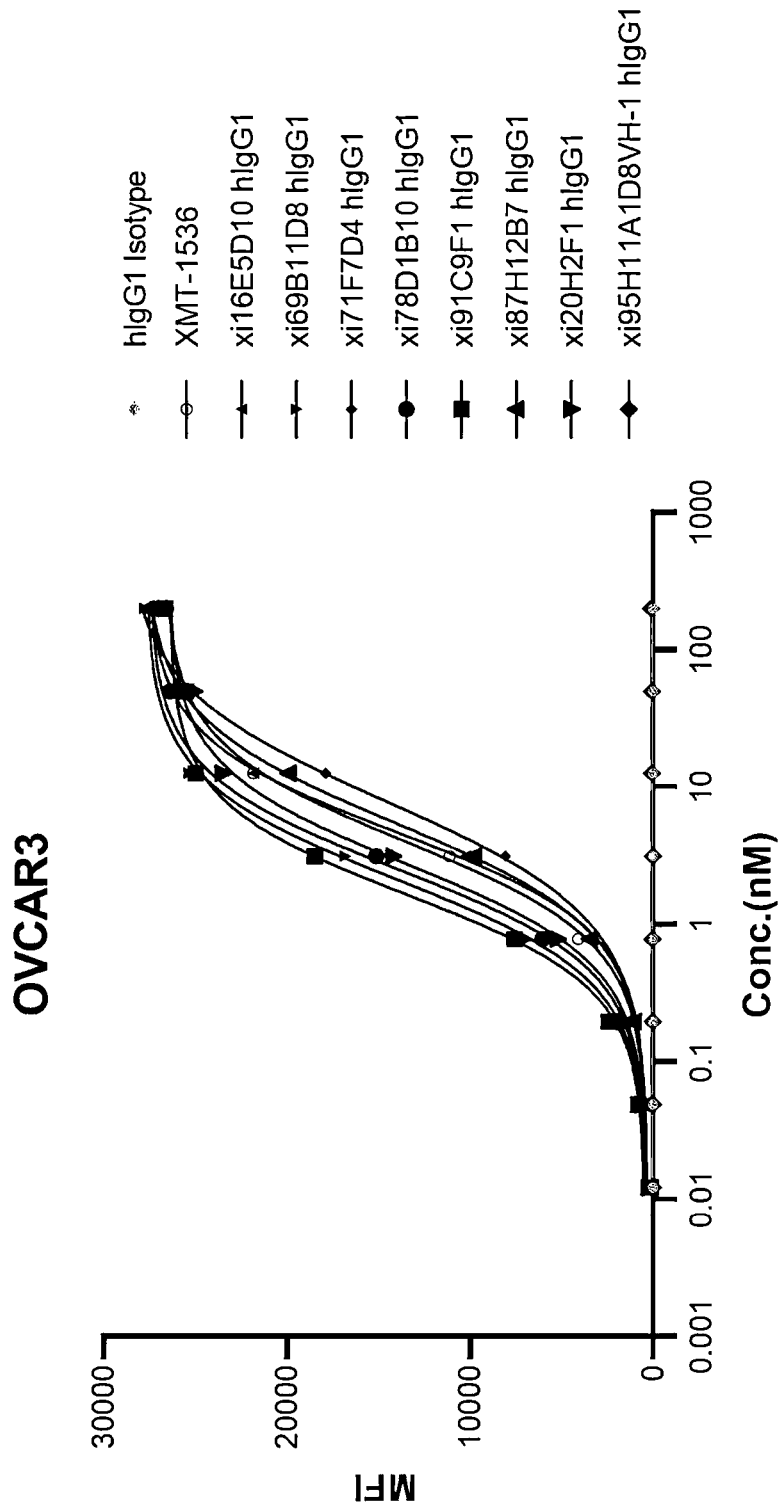
Figure 2A:
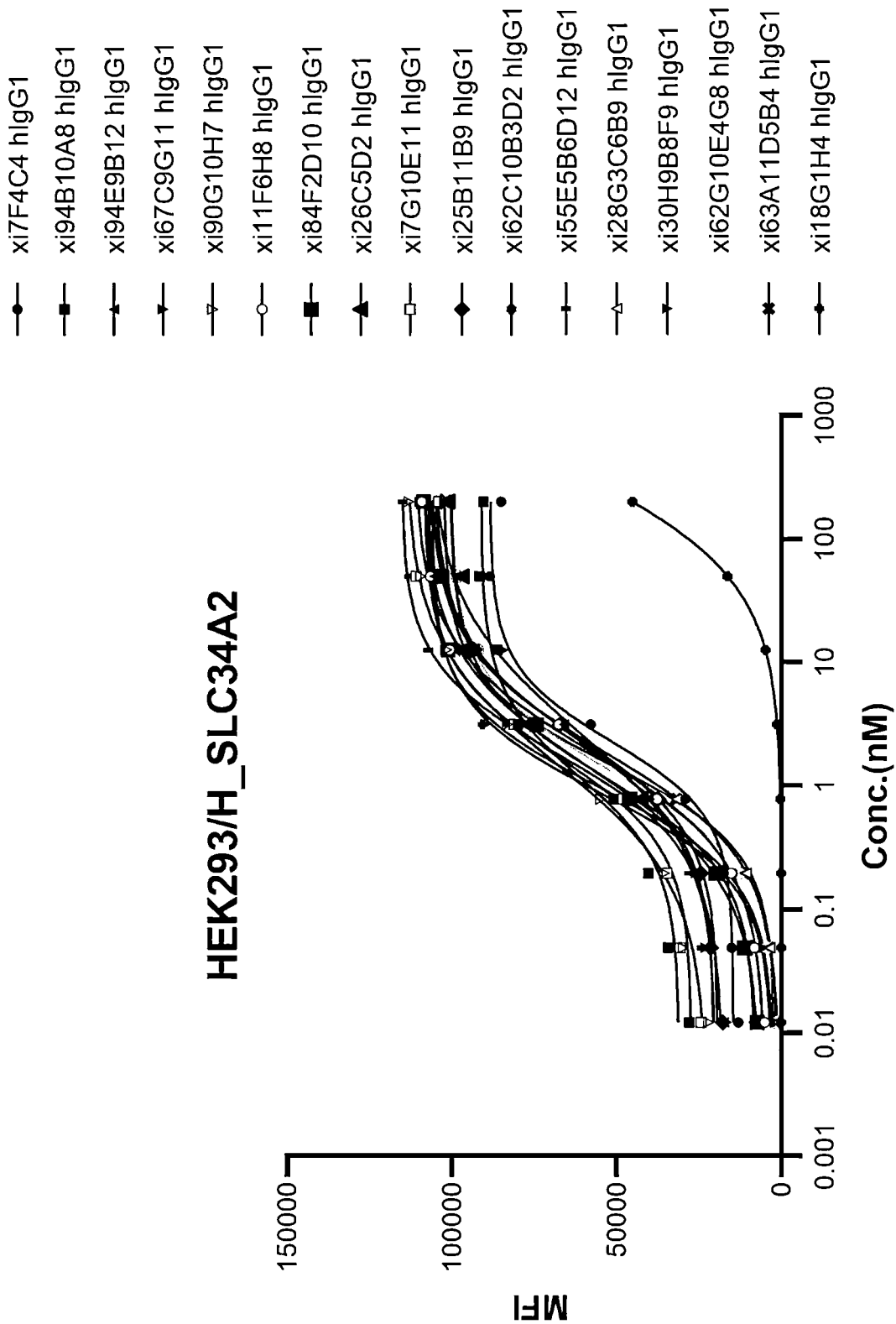
FIG. 2A-B show the binding affinity of the chimeric antibodies to human SLC34A2 expressed on HEK293 cells.
Figure 2B:
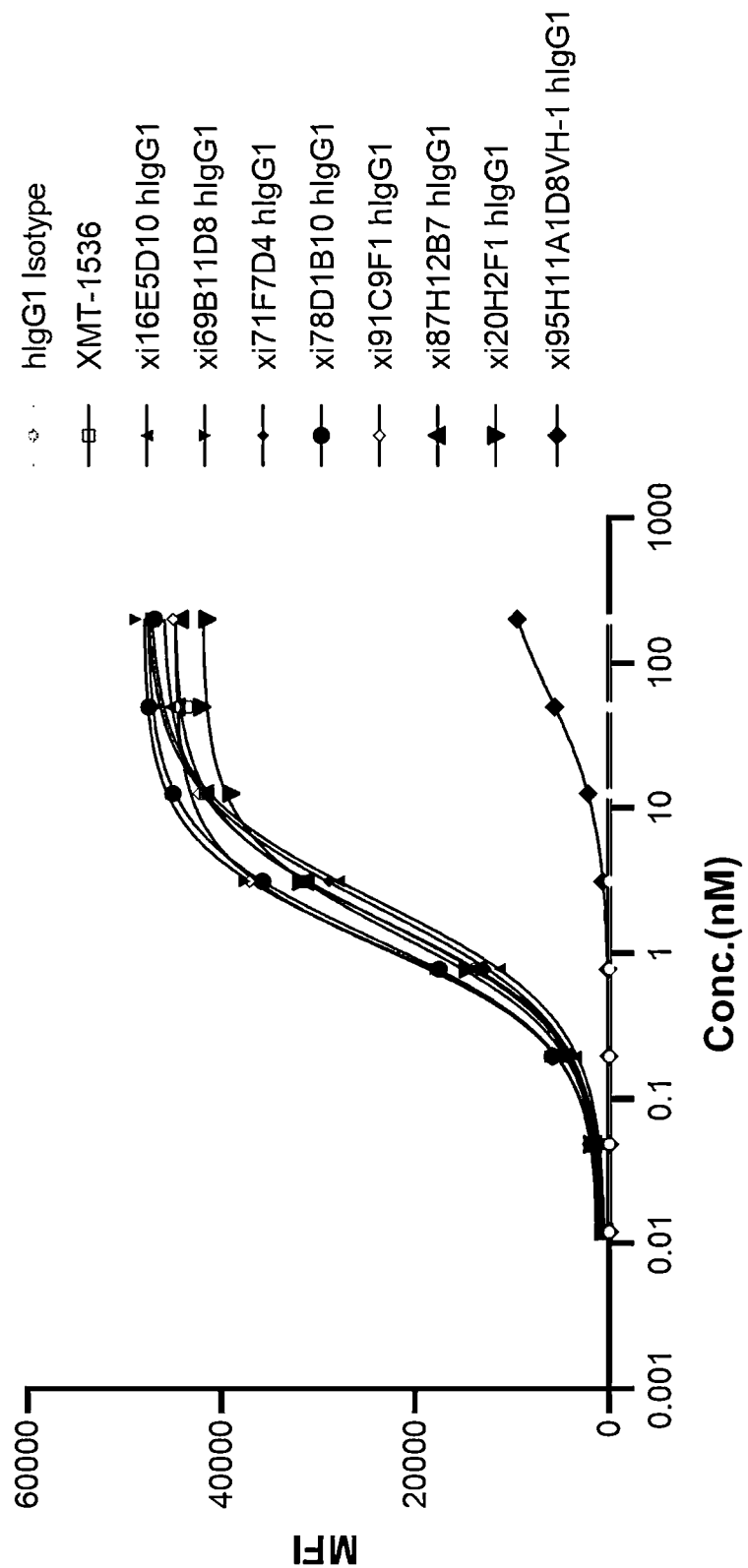

It is to be noted that the term "a" or "an" entity refers to one or more of that entity; for example, "an antibody," is understood to represent one or more antibodies. As such, the terms "a" (or "an"), "one or more," and "at least one" can be used interchangeably herein.

As used herein, the term "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids, are included within the definition of "polypeptide," and the term "polypeptide" may be used instead of, or interchangeably with any of these terms. The term "polypeptide" is also intended to refer to the products of post-expression modifications of the polypeptide, including without limitation glycosylation, acetylation, phosphorylation, amidation, derivatization by known protecting/blocking groups, proteolytic cleavage, or modification by non-naturally occurring amino acids. A polypeptide may be derived from a natural biological source or produced by recombinant technology, but is not necessarily translated from a designated nucleic acid sequence. It may be generated in any manner, including by chemical synthesis.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 40% identity, though preferably less than 25% identity, with one of the sequences of the present disclosure.

A polynucleotide or polynucleotide region (or a polypeptide or polypeptide region) has a certain percentage (for example, 60%, 65%, 70%, 75%, 80%, 85%, 90%, 95%, 98% or 99%) of "sequence identity" to another sequence means that, when aligned, that percentage of bases (or amino acids) are the same in comparing the two sequences.

The term "an equivalent nucleic acid or polynucleotide" refers to a nucleic acid having a nucleotide sequence having a certain degree of homology, or sequence identity, with the nucleotide sequence of the nucleic acid or complement thereof. A homolog of a double stranded nucleic acid is intended to include nucleic acids having a nucleotide sequence which has a certain degree of homology with or with the complement thereof. In one aspect, homologs of nucleic acids are capable of hybridizing to the nucleic acid or complement thereof. Likewise, "an equivalent polypeptide" refers to a polypeptide having a certain degree of homology, or sequence identity, with the amino acid sequence of a reference polypeptide. In some aspects, the sequence identity is at least about 70%, 75%, 80%, 85%, 90%, 95%, 98%, or 99%. In some aspects, the equivalent polypeptide or polynucleotide has one, two, three, four or five addition, deletion, substitution and their combinations thereof as compared to the reference polypeptide or polynucleotide. In some aspects, the equivalent sequence retains the activity (e.g., epitope-binding) or structure (e.g., salt-bridge) of the reference sequence.

As used herein, an "antibody" or "antigen-binding polypeptide" refers to a polypeptide or a polypeptide complex that specifically recognizes and binds to an antigen. An antibody can be a whole antibody and any antigen binding fragment or a single chain thereof. Thus the term "antibody" includes any protein or peptide containing molecule that comprises at least a portion of an immunoglobulin molecule having biological activity of binding to the antigen. Examples of such include, but are not limited to a complementarity determining region (CDR) of a heavy or light chain or a ligand binding portion thereof, a heavy chain or light chain variable region, a heavy chain or light chain constant region, a framework (FR) region, or any portion thereof, or at least one portion of a binding protein.

The terms "antibody fragment" or "antigen-binding fragment", as used herein, is a portion of an antibody such as $F(ab')_2$, $F(ab)_2$, Fab', Fab, Fv, scFv and the like. Regardless of structure, an antibody fragment binds with the same antigen that is recognized by the intact antibody. The term "antibody fragment" includes aptamers, spiegelmers, and diabodies. The term "antibody fragment" also includes any synthetic or genetically engineered protein that acts like an antibody by binding to a specific antigen to form a complex.

A "single-chain variable fragment" or "scFv" refers to a fusion protein of the variable regions of the heavy ($V_H$) and light chains ($V_L$) of immunoglobulins. In some aspects, the regions are connected with a short linker peptide of ten to about 25 amino acids. The linker can be rich in glycine for flexibility, as well as serine or threonine for solubility, and can either connect the N-terminus of the $V_H$ with the C-terminus of the $V_L$, or vice versa. This protein retains the specificity of the original immunoglobulin, despite removal of the constant regions and the introduction of the linker. ScFv molecules are known in the art and are described, e.g., in U.S. Pat. No. 5,892,019.

The term antibody encompasses various broad classes of polypeptides that can be distinguished biochemically. Those skilled in the art will appreciate that heavy chains are classified as gamma, mu, alpha, delta, or epsilon ($\gamma$, $\mu$, $\alpha$, $\delta$, $\epsilon$) with some subclasses among them (e.g., $\gamma1$-$\gamma4$). It is the nature of this chain that determines the "class" of the antibody as IgG, IgM, IgA IgG, or IgE, respectively. The immunoglobulin subclasses (isotypes) e.g., $IgG_1$, $IgG_2$, $IgG_3$, $IgG_4$, $IgG_5$, etc. are well characterized and are known to confer functional specialization. Modified versions of each of these classes and isotypes are readily discernable to the skilled artisan in view of the instant disclosure and, accordingly, are within the scope of the instant disclosure. All immunoglobulin classes are clearly within the scope of the present disclosure, the following discussion will generally be directed to the IgG class of immunoglobulin molecules. With regard to IgG, a standard immunoglobulin molecule comprises two identical light chain polypeptides of molecular weight approximately 23,000 Daltons, and two identical heavy chain polypeptides of molecular weight 53,000-70,000. The four chains are typically joined by disulfide bonds in a "Y" configuration wherein the light chains bracket the heavy chains starting at the mouth of the "Y" and continuing through the variable region.

Antibodies, antigen-binding polypeptides, variants, or derivatives thereof of the disclosure include, but are not limited to, polyclonal, monoclonal, multispecific, human, humanized, primatized, or chimeric antibodies, single chain antibodies, epitope-binding fragments, e.g., Fab, Fab' and $F(ab')_2$, Fd, Fvs, single-chain Fvs (scFv), single-chain antibodies, disulfide-linked Fvs (sdFv), fragments comprising either a VK or VH domain, fragments produced by a Fab expression library, and anti-idiotypic (anti-Id) antibodies (including, e.g., anti-Id antibodies to LIGHT antibodies disclosed herein). Immunoglobulin or antibody molecules of the disclosure can be of any type (e.g., IgG, IgE, IgM, IgD, IgA, and IgY), class (e.g., IgG1, IgG2, IgG3, IgG4, IgA1 and IgA2) or subclass of immunoglobulin molecule.

Light chains are classified as either kappa or lambda (K, λ). Each heavy chain class may be bound with either a kappa or lambda light chain. In general, the light and heavy chains are covalently bonded to each other, and the "tail" portions of the two heavy chains are bonded to each other by covalent disulfide linkages or non-covalent linkages when the immunoglobulins are generated either by hybridomas, B cells or genetically engineered host cells. In the heavy chain, the amino acid sequences run from an N-terminus at the forked ends of the Y configuration to the C-terminus at the bottom of each chain.

Both the light and heavy chains are divided into regions of structural and functional homology. The terms "constant" and "variable" are used functionally. In this regard, it will be appreciated that the variable domains of both the light (VK) and heavy (VH) chain portions determine antigen recognition and specificity. Conversely, the constant domains of the light chain (CK) and the heavy chain (CH1, CH2 or CH3) confer important biological properties such as secretion, transplacental mobility, Fc receptor binding, complement binding, and the like. By convention the numbering of the constant region domains increases as they become more distal from the antigen-binding site or amino-terminus of the antibody. The N-terminal portion is a variable region and at the C-terminal portion is a constant region; the CH3 and CK domains actually comprise the carboxy-terminus of the heavy and light chain, respectively.

As indicated above, the variable region allows the antibody to selectively recognize and specifically bind epitopes on antigens. That is, the VK domain and VH domain, or subset of the complementarity determining regions (CDRs), of an antibody combine to form the variable region that defines a three-dimensional antigen-binding site. This quaternary antibody structure forms the antigen-binding site present at the end of each arm of the Y. More specifically, the antigen-binding site is defined by three CDRs on each of the VH and VK chains (i.e. CDR-H1, CDR-H2, CDR-H3, CDR-L1, CDR-L2 and CDR-L3). In some instances, e.g., certain immunoglobulin molecules derived from camelid species or engineered based on camelid immunoglobulins, a complete immunoglobulin molecule may consist of heavy chains only, with no light chains. See, e.g., Hamers-Casterman et al., Nature 363:446-448 (1993).

In naturally occurring antibodies, the six "complementarity determining regions" or "CDRs" present in each antigen-binding domain are short, non-contiguous sequences of amino acids that are specifically positioned to form the antigen-binding domain as the antibody assumes its three dimensional configuration in an aqueous environment. The remainder of the amino acids in the antigen-binding domains, referred to as "framework" regions, show less inter-molecular variability. The framework regions largely adopt a β-sheet conformation and the CDRs form loops which connect, and in some cases form part of, the β-sheet structure. Thus, framework regions act to form a scaffold that provides for positioning the CDRs in correct orientation by inter-chain, non-covalent interactions. The antigen-binding domain formed by the positioned CDRs defines a surface complementary to the epitope on the immunoreactive antigen. This complementary surface promotes the non-covalent binding of the antibody to its cognate epitope. The amino acids comprising the CDRs and the framework regions, respectively, can be readily identified for any given heavy or light chain variable region by one of ordinary skill in the art, since they have been precisely defined (see "Sequences of Proteins of Immunological Interest," Kabat, E., et al., U.S. Department of Health and Human Services, (1983); and Chothia and Lesk, J. Mol. Biol., 196:901-917 (1987)).

In the case where there are two or more definitions of a term which is used and/or accepted within the art, the definition of the term as used herein is intended to include all such meanings unless explicitly stated to the contrary. A specific example is the use of the term "complementarity determining region" ("CDR") to describe the non-contiguous antigen combining sites found within the variable region of both heavy and light chain polypeptides. This particular region has been described by Kabat et al., U.S. Dept. of Health and Human Services, "Sequences of Proteins of Immunological Interest" (1983) and by Chothia et al., J. Mol. Biol. 196:901-917 (1987), which are incorporated herein by reference in their entireties. The CDR definitions according to Kabat and Chothia include overlapping or subsets of amino acid residues when compared against each other. Nevertheless, application of either definition to refer to a CDR of an antibody or variants thereof is intended to be within the scope of the term as defined and used herein. The appropriate amino acid residues which encompass the CDRs as defined by each of the above cited references are set forth in the table below as a comparison. The exact residue numbers which encompass a particular CDR will vary depending on the sequence and size of the CDR. Those skilled in the art can routinely determine which residues comprise a particular CDR given the variable region amino acid sequence of the antibody.

|  | Kabat | Chothia |
| --- | --- | --- |
| CDR-H1 | 31-35 | 26-32 |
| CDR-H2 | 50-65 | 52-58 |
| CDR-H3 | 95-102 | 95-102 |
| CDR-L1 | 24-34 | 26-32 |
| CDR-L2 | 50-56 | 50-52 |
| CDR-L3 | 89-97 | 91-96 |

Kabat et al. also defined a numbering system for variable domain sequences that is applicable to any antibody. One of ordinary skill in the art can unambiguously assign this system of "Kabat numbering" to any variable domain sequence, without reliance on any experimental data beyond the sequence itself. As used herein, "Kabat numbering" refers to the numbering system set forth by Kabat et al., U.S. Dept. of Health and Human Services, "Sequence of Proteins of Immunological Interest" (1983).

In addition to table above, the Kabat number system describes the CDR regions as follows: CDR-H1 begins at approximately amino acid 31 (i.e., approximately 9 residues after the first cysteine residue), includes approximately 5-7 amino acids, and ends at the next tryptophan residue. CDR-H2 begins at the fifteenth residue after the end of CDR-H1, includes approximately 16-19 amino acids, and ends at the next arginine or lysine residue. CDR-H3 begins at approximately the thirty third amino acid residue after the end of CDR-H2; includes 3-25 amino acids; and ends at the sequence W-G-X-G, where X is any amino acid. CDR-L1 begins at approximately residue 24 (i.e., following a cysteine residue); includes approximately 10-17 residues; and ends at the next tryptophan residue. CDR-L2 begins at approximately the sixteenth residue after the end of CDR-L1 and includes approximately 7 residues. CDR-L3 begins at approximately the thirty third residue after the end of CDR-L2 (i.e., following a cysteine residue); includes approximately 7-11 residues and ends at the sequence F or W-G-X-G, where X is any amino acid.

Antibodies disclosed herein may be from any animal origin including birds and mammals. Preferably, the antibodies are human, murine, donkey, rabbit, goat, guinea pig, camel, llama, horse, or chicken antibodies. In another embodiment, the variable region may be condricthoid in origin (e.g., from sharks).

As used herein, the term "heavy chain constant region" includes amino acid sequences derived from an immunoglobulin heavy chain. A polypeptide comprising a heavy chain constant region comprises at least one of: a CH1 domain, a hinge (e.g., upper, middle, and/or lower hinge region) domain, a CH2 domain, a CH3 domain, or a variant or fragment thereof. For example, an antigen-binding polypeptide for use in the disclosure may comprise a polypeptide chain comprising a CH1 domain; a polypeptide chain comprising a CH1 domain, at least a portion of a hinge domain, and a CH2 domain; a polypeptide chain comprising a CH1 domain and a CH3 domain; a polypeptide chain comprising a CH1 domain, at least a portion of a hinge domain, and a CH3 domain, or a polypeptide chain comprising a CH1 domain, at least a portion of a hinge domain, a CH2 domain, and a CH3 domain. In another embodiment, a polypeptide of the disclosure comprises a polypeptide chain comprising a CH3 domain. Further, an antibody for use in the disclosure may lack at least a portion of a CH2 domain (e.g., all or part of a CH2 domain). As set forth above, it will be understood by one of ordinary skill in the art that the heavy chain constant region may be modified such that they vary in amino acid sequence from the naturally occurring immunoglobulin molecule.

The heavy chain constant region of an antibody disclosed herein may be derived from different immunoglobulin molecules. For example, a heavy chain constant region of a polypeptide may comprise a CH1 domain derived from an $IgG_1$ molecule and a hinge region derived from an $IgG_3$ molecule. In another example, a heavy chain constant region can comprise a hinge region derived, in part, from an $IgG_1$ molecule and, in part, from an $IgG_3$ molecule. In another example, a heavy chain portion can comprise a chimeric hinge derived, in part, from an $IgG_1$ molecule and, in part, from an $IgG_4$ molecule.

As used herein, the term "light chain constant region" includes amino acid sequences derived from antibody light chain. Preferably, the light chain constant region comprises at least one of a constant kappa domain or constant lambda domain.

A "light chain-heavy chain pair" refers to the collection of a light chain and heavy chain that can form a dimer through a disulfide bond between the CL domain of the light chain and the CH1 domain of the heavy chain.

As previously indicated, the subunit structures and three-dimensional configuration of the constant regions of the various immunoglobulin classes are well known. As used herein, the term "VH domain" includes the amino terminal variable domain of an immunoglobulin heavy chain and the term "CH1 domain" includes the first (most amino terminal) constant region domain of an immunoglobulin heavy chain. The CH1 domain is adjacent to the VH domain and is amino terminal to the hinge region of an immunoglobulin heavy chain molecule.

As used herein the term "CH2 domain" includes the portion of a heavy chain molecule that extends, e.g., from about residue 244 to residue 360 of an antibody using conventional numbering schemes (residues 244 to 360, Kabat numbering system; and residues 231-340, EU numbering system; see Kabat et al., U.S. Dept. of Health and Human Services, "Sequences of Proteins of Immunological Interest" (1983). The CH2 domain is unique in that it is not closely paired with another domain. Rather, two N-linked branched carbohydrate chains are interposed between the two CH2 domains of an intact native IgG molecule. It is also well documented that the CH3 domain extends from the CH2 domain to the C-terminal of the IgG molecule and comprises approximately 108 residues.

As used herein, the term "hinge region" includes the portion of a heavy chain molecule that joins the CH1 domain to the CH2 domain. This hinge region comprises approximately 25 residues and is flexible, thus allowing the two N-terminal antigen-binding regions to move independently. Hinge regions can be subdivided into three distinct domains: upper, middle, and lower hinge domains (Roux et al., J. Immunol 161:4083 (1998)).

As used herein the term "disulfide bond" includes the covalent bond formed between two sulfur atoms. The amino acid cysteine comprises a thiol group that can form a disulfide bond or bridge with a second thiol group. In most naturally occurring IgG molecules, the CH1 and CK regions are linked by a disulfide bond and the two heavy chains are linked by two disulfide bonds at positions corresponding to 239 and 242 using the Kabat numbering system (position 226 or 229, EU numbering system).

As used herein, the term "chimeric antibody" will be held to mean any antibody wherein the immunoreactive region or site is obtained or derived from a first species and the constant region (which may be intact, partial or modified in accordance with the instant disclosure) is obtained from a second species. In certain embodiments the target binding region or site will be from a non-human source (e.g. mouse or primate) and the constant region is human.

As used herein, "percent humanization" is calculated by determining the number of framework amino acid differences (i.e., non-CDR difference) between the humanized domain and the germline domain, subtracting that number from the total number of amino acids, and then dividing that by the total number of amino acids and multiplying by 100.

By "specifically binds" or "has specificity to," it is generally meant that an antibody binds to an epitope via its antigen-binding domain, and that the binding entails some complementarity between the antigen-binding domain and the epitope. According to this definition, an antibody is said to "specifically bind" to an epitope when it binds to that epitope, via its antigen-binding domain more readily than it would bind to a random, unrelated epitope. The term "specificity" is used herein to qualify the relative affinity by which a certain antibody binds to a certain epitope. For example, antibody "A" may be deemed to have a higher specificity for a given epitope than antibody "B," or antibody "A" may be said to bind to epitope "C" with a higher specificity than it has for related epitope "D."

As used herein, the terms "treat" or "treatment" refer to both therapeutic treatment and prophylactic or preventative measures, wherein the object is to prevent or slow down (lessen) an undesired physiological change or disorder, such as the progression of cancer. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

By "subject" or "individual" or "animal" or "patient" or "mammal," is meant any subject, particularly a mammalian subject, for whom diagnosis, prognosis, or therapy is desired. Mammalian subjects include humans, domestic animals, farm animals, and zoo, sport, or pet animals such as dogs, cats, guinea pigs, rabbits, rats, mice, horses, cattle, cows, and so on.

As used herein, phrases such as "to a patient in need of treatment" or "a subject in need of treatment" includes subjects, such as mammalian subjects, that would benefit from administration of an antibody or composition of the present disclosure used, e.g., for detection, for a diagnostic procedure and/or for treatment.

Anti-SLC34A2 Antibodies

The present disclosure provides anti-SLC34A2 antibodies and fragments that have high affinity to the human SLC34A2 protein, are potent in mediating ADCC and cytotoxicity, and can effectively induce endocytosis.

In addition, these antibodies have been extensively tested in comparison with two reference antibodies, XMT-1536 and RG-7599, which are under clinical development. The new antibodies outperformed both reference antibodies in terms of general binding affinity, cross-species reactivity, ADCC and cytotoxicity. These antibodies, therefore, are suitable agents for treating various diseases featuring over-expressed SLC34A2, such as cancer.

In accordance with one embodiment of the present disclosure, therefore, provided are antibodies and antigen-binding fragments thereof that are able to bind to SLC34A2. Example antibodies include those murine ones listed in Table 1 (e.g., 30-H9(B8)F9, 62-G10(E4)G8, 63-A11(D5) B4, 91-C9F1, 7-F4C4, 94-B10A8, 94-E9B12, 67-C9G11, 90-G10H7, 11-F6H8, 84-F2D10, 26-C5D2, 7-G10E11, 25-B11B9, 62-C10(B3)D2, 55-E5(B6)D12, 28-G3(C6)B9, 18-G1H4, 16-E5D10, 69-B11D8, 71-F7D4, 78-D1B10, 87-H12B7, 20-H2F1 and 95-H11A1D8), as well as humanized ones of Tables 12-15. Also included are those that include the same CDRs as illustrated herein. In some embodiments, the disclosed antibodies and fragments include those that bind to the same epitope as those illustrated here, and those that compete with the instantly disclosed in binding to SLC34A2.

In accordance with one embodiment of the present disclosure, provided is an antibody or fragment thereof that includes the heavy chain and light chain variable domains with the CDR regions disclosed herein, as well as their biological equivalents.

In one embodiment, the CDRs are those of 30-H9(B8)F9 or its humanized counterparts, as exemplified in Table 12A. In one embodiment, the CDRH1 comprises the amino acid sequence of SEQ ID NO: 51 or a variant thereof having one, two, or three deletions, additions, substitutions or the combinations thereof, the CDRH2 comprises the amino acid sequence of SEQ ID NO: 52 or 57 or a variant thereof having one, two, or three deletions, additions, substitutions or the combinations thereof, the CDRH3 comprises the amino acid sequence of SEQ ID NO: 53 or a variant thereof having one, two, or three deletions, additions, substitutions or the combinations thereof, the CDRL1 comprises the amino acid sequence of SEQ ID NO: 54 or a variant thereof having one, two, or three deletions, additions, substitutions or the combinations thereof, the CDRL2 comprises the amino acid sequence of SEQ ID NO: 55 or a variant thereof having one, two, or three deletions, additions, substitutions or the combinations thereof, and the CDRL3 comprises the amino acid sequence of SEQ ID NO: 56 or a variant thereof having one, two, or three deletions, additions, substitutions or the combinations thereof.

As shown in the experimental examples, the CDRH2 (SEQ ID NO: 57) of 30-H9(B8)F9 includes a NG dipeptide which is likely subject to post-translational modification (PTM). Accordingly, a N=>S mutation was made to prevent such PTM, and the mutated CDRH2 is referred to a PTM-derisked CDR. Experimental data, however, have demonstrated that the PTM-derisked version was as effective as the original one.

In one embodiment, the CDRH1 comprises the amino acid sequence of SEQ ID NO: 51, the CDRH2 comprises the amino acid sequence of SEQ ID NO: 52, the CDRH3 comprises the amino acid sequence of SEQ ID NO: 53, the CDRL1 comprises the amino acid sequence of SEQ ID NO: 54, the CDRL2 comprises the amino acid sequence of SEQ ID NO: 55, and the CDRL3 comprises the amino acid sequence of SEQ ID NO: 56. In one embodiment, the CDRH1 comprises the amino acid sequence of SEQ ID NO: 51, the CDRH2 comprises the amino acid sequence of SEQ ID NO: 57, the CDRH3 comprises the amino acid sequence of SEQ ID NO: 53, the CDRL1 comprises the amino acid sequence of SEQ ID NO: 54, the CDRL2 comprises the amino acid sequence of SEQ ID NO: 55, and the CDRL3 comprises the amino acid sequence of SEQ ID NO: 56.

Also provided, in some embodiments, are those that include the same CDRs as 30-H9(B8)F9 or its humanized counterparts. In some embodiments, the disclosed antibodies and fragments include those that bind to the same epitope as 30-H9(B8)F9 or its humanized counterparts, and those that compete with any of them in binding to SLC34A2.

In some embodiments, the heavy chain variable region comprises an amino acid sequence selected from the group consisting of SEQ ID NO: 1 (mouse or chimeric) and 58-61 (humanized), or a peptide having at least 90% sequence identity to an amino acid sequence selected from the group consisting of SEQ ID NO: 1 (mouse or chimeric) and 58-61 (humanized).

In some embodiments, the light chain variable region comprises an amino acid sequence selected from the group consisting of SEQ ID NO:2 (mouse or chimeric) and 62-65 (humanized), or a peptide having at least 90% sequence identity to an amino acid sequence selected from the group consisting of SEQ ID NO: 2 (mouse or chimeric) and 62-65 (humanized).

In some embodiments, the heavy chain variable region comprises the amino acid sequence of SEQ ID NO:59 and the light chain variable region comprises the amino acid sequence of any one of SEQ ID NO:62-65. In some embodiments, the heavy chain variable region comprises the amino acid sequence of any one of SEQ ID NO: 58-61 and the light chain variable region comprises the amino acid sequence of SEQ ID NO: 62. In some embodiments, the heavy chain variable region comprises the amino acid sequence of SEQ ID NO:59 and the light chain variable region comprises the amino acid sequence of SEQ ID NO:62.

In one embodiment, the CDRs are those of 62-G10(E4) G8 or its humanized counterparts, as exemplified in Table 13A. In one embodiment, the CDRH1 comprises the amino acid sequence of SEQ ID NO: 66 or a variant thereof having one, two, or three deletions, additions, substitutions or the combinations thereof, the CDRH2 comprises the amino acid sequence of SEQ ID NO: 67 or 72 or a variant thereof having one, two, or three deletions, additions, substitutions or the combinations thereof, the CDRH3 comprises the amino acid sequence of SEQ ID NO: 68 or a variant thereof having one, two, or three deletions, additions, substitutions or the combinations thereof, the CDRL1 comprises the amino acid sequence of SEQ ID NO: 69 or a variant thereof having one, two, or three deletions, additions, substitutions or the combinations thereof, the CDRL2 comprises the amino acid sequence of SEQ ID NO: 70 or a variant thereof having one, two, or three deletions, additions, substitutions or the combinations thereof, and the CDRL3 comprises the amino acid sequence of SEQ ID NO: 71 or a variant thereof having one, two, or three deletions, additions, substitutions or the combinations thereof.

One of the CDRs, CDRH2, also included a potential PTM site, NG, which was therefore mutated to NA, as a PTM-derisked version. Experimental data have demonstrated that the PTM-derisked version was as effective as the original one.

In one embodiment, the CDRH1 comprises the amino acid sequence of SEQ ID NO: 66, the CDRH2 comprises the amino acid sequence of SEQ ID NO: 67, the CDRH3 comprises the amino acid sequence of SEQ ID NO: 68, the CDRL1 comprises the amino acid sequence of SEQ ID NO: 69, the CDRL2 comprises the amino acid sequence of SEQ ID NO: 70, and the CDRL3 comprises the amino acid sequence of SEQ ID NO: 71. In one embodiment, the CDRH1 comprises the amino acid sequence of SEQ ID NO: 66, the CDRH2 comprises the amino acid sequence of SEQ ID NO: 72, the CDRH3 comprises the amino acid sequence of SEQ ID NO: 68, the CDRL1 comprises the amino acid sequence of SEQ ID NO: 69, the CDRL2 comprises the amino acid sequence of SEQ ID NO: 70, and the CDRL3 comprises the amino acid sequence of SEQ ID NO: 71.

Also provided, in some embodiments, are those that include the same CDRs as 62-G10(E4)G8 or its humanized counterparts. In some embodiments, the disclosed antibodies and fragments include those that bind to the same epitope as 62-G10(E4)G8 or its humanized counterparts, and those that compete with any of them in binding to SLC34A2.

In some embodiments, the heavy chain variable region comprises an amino acid sequence selected from the group consisting of SEQ ID NO:3 (mouse or chimeric) and 73-76 (humanized), or a peptide having at least 90% sequence identity to an amino acid sequence selected from the group consisting of SEQ ID NO:3 (mouse or chimeric) and 73-76 (humanized).

In some embodiments, the light chain variable region comprises an amino acid sequence selected from the group consisting of SEQ ID NO:4 (mouse or chimeric) and 77-80 (humanized), or a peptide having at least 90% sequence identity to an amino acid sequence selected from the group consisting of SEQ ID NO: 4 (mouse or chimeric) and 77-80 (humanized).

In some embodiments, the heavy chain variable region comprises the amino acid sequence of SEQ ID NO:76 and the light chain variable region comprises the amino acid sequence of any one of SEQ ID NO: 77-80. In some embodiments, the heavy chain variable region comprises the amino acid sequence of any one of SEQ ID NO: 73-76 and the light chain variable region comprises the amino acid sequence of SEQ ID NO: 79. In some embodiments, the heavy chain variable region comprises the amino acid sequence of SEQ ID NO:76 and the light chain variable region comprises the amino acid sequence of SEQ ID NO:79.

In one embodiment, the CDRs are those of 63-A11(D5) B4 or its humanized counterparts, as exemplified in Table 14A. In one embodiment, the CDRH1 comprises the amino acid sequence of SEQ ID NO: 81 or a variant thereof having one, two, or three deletions, additions, substitutions or the combinations thereof, the CDRH2 comprises the amino acid sequence of SEQ ID NO: 82 or 87 or a variant thereof having one, two, or three deletions, additions, substitutions or the combinations thereof, the CDRH3 comprises the amino acid sequence of SEQ ID NO: 83 or a variant thereof having one, two, or three deletions, additions, substitutions or the combinations thereof, the CDRL1 comprises the amino acid sequence of SEQ ID NO: 84 or a variant thereof having one, two, or three deletions, additions, substitutions or the combinations thereof, the CDRL2 comprises the amino acid sequence of SEQ ID NO: 85 or a variant thereof having one, two, or three deletions, additions, substitutions or the combinations thereof, and the CDRL3 comprises the amino acid sequence of SEQ ID NO: 86 or a variant thereof having one, two, or three deletions, additions, substitutions or the combinations thereof.

One of the CDRs, CDRH2, also included a potential PTM site, NG, which was therefore mutated to SG, as a PTM-derisked version. Experimental data have demonstrated that the PTM-derisked version was as effective as the original one.

In one embodiment, the CDRH1 comprises the amino acid sequence of SEQ ID NO: 81, the CDRH2 comprises the amino acid sequence of SEQ ID NO: 82, the CDRH3 comprises the amino acid sequence of SEQ ID NO: 83, the CDRL1 comprises the amino acid sequence of SEQ ID NO: 84, the CDRL2 comprises the amino acid sequence of SEQ ID NO: 85, and the CDRL3 comprises the amino acid sequence of SEQ ID NO: 86. In one embodiment, the CDRH1 comprises the amino acid sequence of SEQ ID NO: 81, the CDRH2 comprises the amino acid sequence of SEQ ID NO: 87, the CDRH3 comprises the amino acid sequence of SEQ ID NO: 83, the CDRL1 comprises the amino acid sequence of SEQ ID NO: 84, the CDRL2 comprises the amino acid sequence of SEQ ID NO: 85, and the CDRL3 comprises the amino acid sequence of SEQ ID NO: 86.

Also provided, in some embodiments, are those that include the same CDRs as 63-A11(D5)B4 or its humanized counterparts. In some embodiments, the disclosed antibodies and fragments include those that bind to the same epitope as 63-A11(D5)B4 or its humanized counterparts, and those that compete with any of them in binding to SLC34A2.

In some embodiments, the heavy chain variable region comprises an amino acid sequence selected from the group consisting of SEQ ID NO:5 (mouse or chimeric) and 88-91 (humanized), or a peptide having at least 90% sequence identity to an amino acid sequence selected from the group consisting of SEQ ID NO:5 (mouse or chimeric) and 88-91 (humanized).

In some embodiments, the light chain variable region comprises an amino acid sequence selected from the group consisting of SEQ ID NO:6 (mouse or chimeric) and 92-95 (humanized), or a peptide having at least 90% sequence identity to an amino acid sequence selected from the group consisting of SEQ ID NO: 6 (mouse or chimeric) and 92-95 (humanized).

In some embodiments, the heavy chain variable region comprises the amino acid sequence of SEQ ID NO:90 and the light chain variable region comprises the amino acid sequence of any one of SEQ ID NO: 92-95. In some embodiments, the heavy chain variable region comprises the amino acid sequence of any one of SEQ ID NO: 88-91 and the light chain variable region comprises the amino acid sequence of SEQ ID NO: 92. In some embodiments, the heavy chain variable region comprises the amino acid sequence of SEQ ID NO:90 and the light chain variable region comprises the amino acid sequence of SEQ ID NO:92.

In one embodiment, the CDRs are those of 91-C9F1 or its humanized counterparts, as exemplified in Table 15A. In one embodiment, the CDRH1 comprises the amino acid sequence of SEQ ID NO: 96 or a variant thereof having one, two, or three deletions, additions, substitutions or the combinations thereof, the CDRH2 comprises the amino acid sequence of SEQ ID NO: 97 or 102 or a variant thereof having one, two, or three deletions, additions, substitutions or the combinations thereof, the CDRH3 comprises the amino acid sequence of SEQ ID NO: 98 or 103 or a variant thereof having one, two, or three deletions, additions, substitutions or the combinations thereof, the CDRL1 comprises the amino acid sequence of SEQ ID NO: 99 or a variant thereof having one, two, or three deletions, additions, substitutions or the combinations thereof, the CDRL2 comprises the amino acid sequence of SEQ ID NO: 100 or a variant thereof having one, two, or three deletions, additions, substitutions or the combinations thereof, and the CDRL3 comprises the amino acid sequence of SEQ ID NO: 101 or a variant thereof having one, two, or three deletions, additions, substitutions or the combinations thereof.

Two of the CDRs, CDRH2 and CDRH3, also included a potential PTM site, NG, which was therefore mutated to ND and NA respectively, as PTM-derisked versions. Experimental data have demonstrated that the PTM-derisked versions were as effective as the original one.

In one embodiment, the CDRH1 comprises the amino acid sequence of SEQ ID NO: 96, the CDRH2 comprises the amino acid sequence of SEQ ID NO: 97, the CDRH3 comprises the amino acid sequence of SEQ ID NO: 98 or 103, the CDRL1 comprises the amino acid sequence of SEQ ID NO: 99, the CDRL2 comprises the amino acid sequence of SEQ ID NO: 100, and the CDRL3 comprises the amino acid sequence of SEQ ID NO: 101. In one embodiment, the CDRH1 comprises the amino acid sequence of SEQ ID NO: 96, the CDRH2 comprises the amino acid sequence of SEQ ID NO: 97 or 102, the CDRH3 comprises the amino acid sequence of SEQ ID NO: 98, the CDRL1 comprises the amino acid sequence of SEQ ID NO: 99, the CDRL2 comprises the amino acid sequence of SEQ ID NO: 100, and the CDRL3 comprises the amino acid sequence of SEQ ID NO: 101. In one embodiment, the CDRH1 comprises the amino acid sequence of SEQ ID NO: 96, the CDRH2 comprises the amino acid sequence of SEQ ID NO: 97, the CDRH3 comprises the amino acid sequence of SEQ ID NO: 98, the CDRL1 comprises the amino acid sequence of SEQ ID NO: 99, the CDRL2 comprises the amino acid sequence of SEQ ID NO: 100, and the CDRL3 comprises the amino acid sequence of SEQ ID NO: 101.

Also provided, in some embodiments, are those that include the same CDRs as 91-C9F1 or its humanized counterparts. In some embodiments, the disclosed antibodies and fragments include those that bind to the same epitope as 91-C9F1 or its humanized counterparts, and those that compete with any of them in binding to SLC34A2.

In some embodiments, the heavy chain variable region comprises an amino acid sequence selected from the group consisting of SEQ ID NO:7 (mouse or chimeric) and 104-107 (humanized), or a peptide having at least 90% sequence identity to an amino acid sequence selected from the group consisting of SEQ ID NO:7 (mouse or chimeric) and 104-107 (humanized).

In some embodiments, the light chain variable region comprises an amino acid sequence selected from the group consisting of SEQ ID NO:8 (mouse or chimeric) and 108-111 (humanized), or a peptide having at least 90% sequence identity to an amino acid sequence selected from the group consisting of SEQ ID NO: 8 (mouse or chimeric) and 108-111 (humanized).

In some embodiments, the heavy chain variable region comprises the amino acid sequence of SEQ ID NO:105 and the light chain variable region comprises the amino acid sequence of any one of SEQ ID NO: 108-111. In some embodiments, the heavy chain variable region comprises the amino acid sequence of any one of SEQ ID NO: 104-107 and the light chain variable region comprises the amino acid sequence of SEQ ID NO: 110. In some embodiments, the heavy chain variable region comprises the amino acid sequence of SEQ ID NO:105 and the light chain variable region comprises the amino acid sequence of SEQ ID NO:110.

It is appreciated that CDRs can be modified to include those having one, two or three amino acid addition, deletion and/or substitutions. In some embodiments, the substitutions can be conservative substitutions.

A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a nonessential amino acid residue in an immunoglobulin polypeptide is preferably replaced with another amino acid residue from the same side chain family. In another embodiment, a string of amino acids can be replaced with a structurally similar string that differs in order and/or composition of side chain family members.

Non-limiting examples of conservative amino acid substitutions are provided in the table below, where a similarity score of 0 or higher indicates conservative substitution between the two amino acids.

TABLE A

Amino Acid Similarity Matrix

|   | C | G | P | S | A | T | D | E | N | Q | H | K | R | V | M | I | L | F | Y | W |
|---|---|---|---|---|---|---|---|---|---|---|---|---|---|---|---|---|---|---|---|---|
| W | −8 | −7 | −6 | −2 | −6 | −5 | −7 | −7 | −4 | −5 | −3 | −3 | 2 | −6 | −4 | −5 | −2 | 0 | 0 | 17 |
| Y | 0 | −5 | −5 | −3 | −3 | −3 | −4 | −4 | −2 | −4 | 0 | −4 | −5 | −2 | −2 | −1 | −1 | 7 | 10 | |
| F | −4 | −5 | −5 | −3 | −4 | −3 | −6 | −5 | −4 | −5 | −2 | −5 | −4 | −1 | 0 | 1 | 2 | 9 | | |
| L | −6 | −4 | −3 | −3 | −2 | −2 | −4 | −3 | −3 | −2 | −2 | −3 | −3 | 2 | 4 | 2 | 6 | | | |

TABLE A-continued

Amino Acid Similarity Matrix

| | C | G | P | S | A | T | D | E | N | Q | H | K | R | V | M | I | L | F | Y | W |
|---|---|---|---|---|---|---|---|---|---|---|---|---|---|---|---|---|---|---|---|---|
| I | -2 | -3 | -2 | -1 | -1 | 0 | -2 | -2 | -2 | -2 | -2 | -2 | -2 | 4 | 2 | 5 | | | | |
| M | -5 | -3 | -2 | -2 | -1 | -1 | -3 | -2 | 0 | -1 | -2 | 0 | 0 | 2 | 6 | | | | | |
| V | -2 | -1 | -1 | -1 | 0 | 0 | -2 | -2 | -2 | -2 | -2 | -2 | -2 | 4 | | | | | | |
| R | -4 | -3 | 0 | 0 | -2 | -1 | -1 | -1 | 0 | 1 | 2 | 3 | 6 | | | | | | | |
| K | -5 | -2 | -1 | 0 | -1 | 0 | 0 | 0 | 1 | 1 | 0 | 5 | | | | | | | | |
| H | -3 | -2 | 0 | -1 | -1 | -1 | 1 | 1 | 2 | 3 | 6 | | | | | | | | | |
| Q | -5 | -1 | 0 | -1 | 0 | -1 | 2 | 2 | 1 | 4 | | | | | | | | | | |
| N | -4 | 0 | -1 | 1 | 0 | 0 | 2 | 1 | 2 | | | | | | | | | | | |
| E | -5 | 0 | -1 | 0 | 0 | 0 | 3 | 4 | | | | | | | | | | | | |
| D | -5 | 1 | -1 | 0 | 0 | 0 | 4 | | | | | | | | | | | | | |
| T | -2 | 0 | 0 | 1 | 1 | 3 | | | | | | | | | | | | | | |
| A | -2 | 1 | 1 | 1 | 2 | | | | | | | | | | | | | | | |
| S | 0 | 1 | 1 | 1 | | | | | | | | | | | | | | | | |
| P | -3 | -1 | 6 | | | | | | | | | | | | | | | | | |
| G | -3 | 5 | | | | | | | | | | | | | | | | | | |
| C | 12 | | | | | | | | | | | | | | | | | | | |

TABLE B

Conservative Amino Acid Substitutions

| For Amino Acid | Substitution With |
|---|---|
| Alanine | D-Ala, Gly, Aib, β-Ala, L-Cys, D-Cys |
| Arginine | D-Arg, Lys, D-Lys, Orn D-Orn |
| Asparagine | D-Asn, Asp, D-Asp, Glu, D-Glu Gln, D-Gln |
| Aspartic Acid | D-Asp, D-Asn, Asn, Glu, D-Glu, Gln, D-Gln |
| Cysteine | D-Cys, S-Me-Cys, Met, D-Met, Thr, D-Thr, L-Ser, D-Ser |
| Glutamine | D-Gln, Asn, D-Asn, Glu, D-Glu, Asp, D-Asp |
| Glutamic Acid | D-Glu, D-Asp, Asp, Asn, D-Asn, Gln, D-Gln |
| Glycine | Ala, D-Ala, Pro, D-Pro, Aib, β-Ala |
| Isoleucine | D-Ile, Val, D-Val, Leu, D-Leu, Met, D-Met |
| Leucine | Val, D-Val, Met, D-Met, D-Ile, D-Leu, Ile |
| Lysine | D-Lys, Arg, D-Arg, Orn, D-Orn |
| Methionine | D-Met, S-Me-Cys, Ile, D-Ile, Leu, D-Leu, Val, D-Val |
| Phenylalanine | D-Phe, Tyr, D-Tyr, His, D-His, Trp, D-Trp |
| Proline | D-Pro |
| Serine | D-Ser, Thr, D-Thr, allo-Thr, L-Cys, D-Cys |
| Threonine | D-Thr, Ser, D-Ser, allo-Thr, Met, D-Met, Val, D-Val |
| Tyrosine | D-Tyr, Phe, D-Phe, His, D-His, Trp, D-Trp |
| Valine | D-Val, Leu, D-Leu, Ile, D-Ile, Met, D-Met |

It will also be understood by one of ordinary skill in the art that antibodies as disclosed herein may be modified such that they vary in amino acid sequence from the naturally occurring binding polypeptide from which they were derived. For example, a polypeptide or amino acid sequence derived from a designated protein may be similar, e.g., have a certain percent identity to the starting sequence, e.g., it may be 60%, 70%, 75%, 80%, 85%, 90%, 95%, 98%, or 99% identical to the starting sequence.

In certain embodiments, the antibody comprises an amino acid sequence or one or more moieties not normally associated with an antibody. Exemplary modifications are described in more detail below. For example, an antibody of the disclosure may comprise a flexible linker sequence, or may be modified to add a functional moiety (e.g., PEG, a drug, a toxin, or a label).

Antibodies, variants, or derivatives thereof of the disclosure include derivatives that are modified, i.e., by the covalent attachment of any type of molecule to the antibody such that covalent attachment does not prevent the antibody from binding to the epitope. For example, but not by way of limitation, the antibodies can be modified, e.g., by glycosylation, acetylation, pegylation, phosphorylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the antibodies may contain one or more non-classical amino acids.

The antibodies can be detectably labeled by coupling it to a chemiluminescent compound. The presence of the chemiluminescent-tagged antigen-binding polypeptide is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

The antibodies can also be detectably labeled using fluorescence emitting metals such as $^{152}$Eu, or others of the lanthanide series. These metals can be attached to the antibody using such metal chelating groups as diethylenetriaminepentacetic acid (DTPA) or ethylenediaminetetraacetic acid (EDTA). Techniques for conjugating various moieties to an antibody are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. (1985); Hellstrom et al., "Antibodies For Drug Delivery", in Controlled Drug Delivery (2nd Ed.), Robinson et al., (eds.), Marcel Dekker, Inc., pp. 623-53 (1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), and Academic Press pp. 303-16 (1985).

Bi-Functional Molecules and Combination Therapies

SLC34A2 is overexpressed on tumor cells. As a tumor antigen targeting molecule, an antibody or antigen-binding fragment specific to SLC34A2 can be combined with a second antigen-binding fragment specific to an immune cell, or an antigen-binding fragment specific to an immune checkpoint to generate a combination therapy or a bispecific antibody.

In some embodiments, the immune cell is selected from the group consisting of a T cell, a B cell, a monocyte, a macrophage, a neutrophil, a dendritic cell, a phagocyte, a natural killer cell, an eosinophil, a basophil, and a mast cell. Molecules on the immune cell which can be targeted include, for example, CCL1, CD3, CD16, CD19, CD28, and CD64. Other examples include PD-1, PD-L1, CTLA-4, LAG-3 (also known as CD223), CD28, CD122, 4-1BB (also known as CD137), TIM3, OX-40 or OX40L, CD40 or CD40L, LIGHT, ICOS/ICOSL, GITR/GITRL, TIGIT, CD27, VISTA, B7H3, B7H4, HEVM or BTLA (also known as CD272), killer-cell immunoglobulin-like receptors (KIRs), and CD47.

Different format of bispecific antibodies are also provided. In some embodiments, each of the anti-SLC34A2 fragment and the second fragment each is independently selected from a Fab fragment, a single-chain variable fragment (scFv), or a single-domain antibody. In some embodiments, the bispecific antibody further includes a Fc fragment.

Bifunctional molecules that include not just antibody or antigen binding fragment are also provided. As a tumor antigen targeting molecule, an antibody or antigen-binding fragment specific to SLC34A2, such as those described here, can be combined with an immune cytokine or ligand optionally through a peptide linker. The linked immune cytokines or ligands include, but not limited to, IL-2, IL-3, IL-4, IL-5, IL-6, IL-7, IL-10, IL-12, IL-13, IL-15, GM-CSF, TNF-α, CD40L, OX40L, CD27L, CD30L, 4-1BBL, LIGHT and GITRL. Such bi-functional molecules can combine the immune checkpoint blocking effect with tumor site local immune modulation.

Polynucleotides Encoding the Antibodies and Methods of Preparing the Antibodies

The present disclosure also provides isolated polynucleotides or nucleic acid molecules encoding the antibodies, variants or derivatives thereof of the disclosure. The polynucleotides of the present disclosure may encode the entire heavy and light chain variable regions of the antigen-binding polypeptides, variants or derivatives thereof on the same polynucleotide molecule or on separate polynucleotide molecules. Additionally, the polynucleotides of the present disclosure may encode portions of the heavy and light chain variable regions of the antigen-binding polypeptides, variants or derivatives thereof on the same polynucleotide molecule or on separate polynucleotide molecules.

Methods of making antibodies are well known in the art and described herein. In certain embodiments, both the variable and constant regions of the antigen-binding polypeptides of the present disclosure are fully human. Fully human antibodies can be made using techniques described in the art and as described herein. For example, fully human antibodies against a specific antigen can be prepared by administering the antigen to a transgenic animal which has been modified to produce such antibodies in response to antigenic challenge, but whose endogenous loci have been disabled. Exemplary techniques that can be used to make such antibodies are described in U.S. Pat. Nos. 6,150,584; 6,458,592; 6,420,140 which are incorporated by reference in their entireties.

Treatment Methods

As described herein, the antibodies, variants or derivatives of the present disclosure may be used in certain treatment and diagnostic methods.

The present disclosure is further directed to antibody-based therapies which involve administering the antibodies of the disclosure to a patient such as an animal, a mammal, and a human for treating one or more of the disorders or conditions described herein. Therapeutic compounds of the disclosure include, but are not limited to, antibodies of the disclosure (including variants and derivatives thereof as described herein) and nucleic acids or polynucleotides encoding antibodies of the disclosure (including variants and derivatives thereof as described herein).

The antibodies of the disclosure can also be used to treat or inhibit cancer. In some embodiments, the cancer cells in the patient express or overexpress SLC34A2. As provided above, SLC34A2 can be overexpressed in tumor cells, in particular gastric, pancreatic, esophageal, ovarian, and lung tumors. Inhibition of SLC34A2 has been shown to be useful for treating the tumors.

Accordingly, in some embodiments, provided are methods for treating a cancer in a patient in need thereof. The method, in one embodiment, entails administering to the patient an effective amount of an antibody of the present disclosure. In some embodiments, at least one of the cancer cells (e.g., stromal cells) in the patient over-express SLC34A2.

Cellular therapies, such as chimeric antigen receptor (CAR) T-cell therapies, are also provided in the present disclosure. A suitable cell can be used, that is put in contact with an anti-SLC34A2 antibody of the present disclosure (or alternatively engineered to express an anti-SLC34A2 antibody of the present disclosure). In some embodiments, the antibody is presented in a chimeric antigen receptor (CAR). Upon such contact or engineering, the cell can then be introduced to a cancer patient in need of a treatment. The cancer patient may have a cancer of any of the types as disclosed herein. The cell (e.g., T cell) can be, for instance, a tumor-infiltrating T lymphocyte, a CD4+ T cell, a CD8+ T cell, or the combination thereof, without limitation.

In some embodiments, the cell was isolated from the cancer patient him- or her-self. In some embodiments, the cell was provided by a donor or from a cell bank. When the cell is isolated from the cancer patient, undesired immune reactions can be minimized.

Non-limiting examples of cancers include bladder cancer, breast cancer, colorectal cancer, endometrial cancer, esophageal cancer, head and neck cancer, kidney cancer, leukemia, liver cancer, lung cancer, lymphoma, melanoma, pancreatic cancer, prostate cancer, and thyroid cancer. In some embodiments, the cancer is one or more of gastric, pancreatic, esophageal, ovarian, and lung cancers.

Additional diseases or conditions associated with increased cell survival, that may be treated, prevented, diagnosed and/or prognosed with the antibodies or variants, or derivatives thereof of the disclosure include, but are not limited to, progression, and/or metastases of malignancies and related disorders such as leukemia (including acute leukemias (e.g., acute lymphocytic leukemia, acute myelocytic leukemia (including myeloblastic, promyelocytic, myelomonocytic, monocytic, and erythroleukemia)) and chronic leukemias (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyo sarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma and retinoblastoma.

A specific dosage and treatment regimen for any particular patient will depend upon a variety of factors, including the particular antibodies, variant or derivative thereof used, the patient's age, body weight, general health, sex, and diet, and the time of administration, rate of excretion, drug combination, and the severity of the particular disease being treated. Judgment of such factors by medical caregivers is within the ordinary skill in the art. The amount will also depend on the individual patient to be treated, the route of administration, the type of formulation, the characteristics of the compound used, the severity of the disease, and the desired effect. The amount used can be determined by pharmacological and pharmacokinetic principles well known in the art.

Methods of administration of the antibodies, variants or include but are not limited to intradermal, intramuscular, intraperitoneal, intravenous, subcutaneous, intranasal, epidural, and oral routes. The antigen-binding polypeptides or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Thus, pharmaceutical compositions containing the antigen-binding polypeptides of the disclosure may be administered orally, rectally, parenterally, intracisternally, intravaginally, intraperitoneally, topically (as by powders, ointments, drops or transdermal patch), bucally, or as an oral or nasal spray.

The term "parenteral" as used herein refers to modes of administration which include intravenous, intramuscular, intraperitoneal, intrasternal, subcutaneous and intra-articular injection and infusion.

Administration can be systemic or local. In addition, it may be desirable to introduce the antibodies of the disclosure into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

It may be desirable to administer the antigen-binding polypeptides or compositions of the disclosure locally to the area in need of treatment; this may be achieved by, for example, and not by way of limitation, local infusion during surgery, topical application, e.g., in conjunction, with a wound dressing after surgery, by injection, by means of a catheter, by means of a suppository, or by means of an implant, said implant being of a porous, non-porous, or gelatinous material, including membranes, such as sialastic membranes, or fibers. Preferably, when administering a protein, including an antibody, of the disclosure, care must be taken to use materials to which the protein does not absorb.

The amount of the antibodies of the disclosure which will be effective in the treatment, inhibition and prevention of an immune or malignant disease, disorder or condition can be determined by standard clinical techniques. In addition, in vitro assays may optionally be employed to help identify optimal dosage ranges. The precise dose to be employed in the formulation will also depend on the route of administration, and the seriousness of the disease, disorder or condition, and should be decided according to the judgment of the practitioner and each patient's circumstances. Effective doses may be extrapolated from dose-response curves derived from in vitro or animal model test systems.

As a general proposition, the dosage administered to a patient of the antigen-binding polypeptides of the present disclosure is typically 0.1 mg/kg to 100 mg/kg of the patient's body weight, between 0.1 mg/kg and 20 mg/kg of the patient's body weight, or 1 mg/kg to 10 mg/kg of the patient's body weight. Generally, human antibodies have a longer half-life within the human body than antibodies from other species due to the immune response to the foreign polypeptides. Thus, lower dosages of human antibodies and less frequent administration is often possible. Further, the dosage and frequency of administration of antibodies of the disclosure may be reduced by enhancing uptake and tissue penetration (e.g., into the brain) of the antibodies by modifications such as, for example, lipidation.

In an additional embodiment, the compositions of the disclosure are administered in combination with cytokines. Cytokines that may be administered with the compositions of the disclosure include, but are not limited to, IL-2, IL-3, IL-4, IL-5, IL-6, IL-7, IL-10, IL-12, IL-13, IL-15, anti-CD40, CD40L, and TNF-α.

In additional embodiments, the compositions of the disclosure are administered in combination with other therapeutic or prophylactic regimens, such as, for example, radiation therapy.

Diagnostic Methods

Over-expression of SLC34A2 is observed in certain tumor samples, and patients having SLC34A2-over-expressing cells are likely responsive to treatments with the anti-SLC34A2 antibodies of the present disclosure. Accordingly, the antibodies of the present disclosure can also be used for diagnostic and prognostic purposes.

A sample that preferably includes a cell can be obtained from a patient, which can be a cancer patient or a patient desiring diagnosis. The cell be a cell of a tumor tissue or a tumor block, a blood sample, a urine sample or any sample from the patient. Upon optional pre-treatment of the sample, the sample can be incubated with an antibody of the present disclosure under conditions allowing the antibody to interact with an SLC34A2 protein potentially present in the sample. Methods such as ELISA can be used, taking advantage of the anti-SLC34A2 antibody, to detect the presence of the SLC34A2 protein in the sample.

Presence of the SLC34A2 protein in the sample (optionally with the amount or concentration) can be used for diagnosis of cancer, as an indication that the patient is suitable for a treatment with the antibody, or as an indication that the patient has (or has not) responded to a cancer treatment. For a prognostic method, the detection can be done at once, twice or more, at certain stages, upon initiation of a cancer treatment to indicate the progress of the treatment.

Compositions

The present disclosure also provides pharmaceutical compositions. Such compositions comprise an effective amount of an antibody, and an acceptable carrier. In some embodiments, the composition further includes a second anticancer agent (e.g., an immune checkpoint inhibitor).

In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. Further, a "pharmaceutically acceptable carrier" will generally be a non-toxic solid, semisolid or liquid filler, diluent, encapsulating material or formulation auxiliary of any type.

The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents such as acetates, citrates or phosphates. Antibacterial agents such as benzyl alcohol or methyl parabens; antioxidants such as ascorbic acid or sodium bisulfite; chelating agents such as ethylenediaminetetraacetic acid; and agents for the adjustment of tonicity such as sodium chloride or dextrose are also envisioned. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in Remington's Pharmaceutical Sciences by E. W. Martin, incorporated herein by reference. Such compositions will contain a therapeutically effective amount of the antigen-binding polypeptide, preferably in purified form, together with a suitable amount of carrier so as to provide the form for proper administration to the patient. The formulation should suit the mode of administration. The parental preparation can be enclosed in ampoules, disposable syringes or multiple dose vials made of glass or plastic.

In an embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compounds of the disclosure can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

EXAMPLES

Example 1: Generation of Murine Monoclonal Antibodies Against Human SLC34A2

The human SLC34A2 protein was used to immunize different strains of mice, and hybridomas were generated accordingly. SLC34A2 positive binders were selected and subcloned. Subsequently, in vitro binding and functional screening were carried out and lead antibodies with highest binding affinity and strongest functional potency were identified.

The VH/VL sequences of 25 lead murine antibodies are provided in Table 1 below.

TABLE 1

| VH/VL sequence of the lead murine antibodies | | |
|---|---|---|
| Antibody chain | Sequence (CDRs are underlined) | SEQ ID NO: |
| 30-H9(B8)F9 VH | QVQLQQPGAELVKPGASVKMSCKTSGYTFTTNNMHWVKQTPGQGLEWIGAIY PGNGATAYNQKFKGKATLTADKSSSTAYMQLSSLTSEASAVYYCARGMYGHG AMDYWGQGTSVIVSS | 1 |
| 30-H9(B8)F9 VL | DIVMTQSHKFMSRSVGDRVRITCKASQDVGTAVAWYQQKPGQSPKLLIYWAT TRHSGVPDRFTGSGSGTDFIFTISNVQSEDLADYFCQQYSSNPLTFGAGTKL ELK | 2 |
| 62-G10(E4)G8 VH | QVQLQQSGAEVVKPGASVKMSCKASGYTFPSYITHWVKQTPGQGLEWIGAIY PGNGDTSYIQKFKGKATLTADKSSSTAYMQLSSLTSEDSAVYYCARGTYGTS AWFTYWGQGTLVTVSA | 3 |
| 62-G10(E4)G8 VL | DIVLTQSPATLSVTPGDSVSLCRARQNIGNNLYWYQQKSHESPRLLIKYAS QSISGIPSRFSGSGSGTDFTLTINSVETEDFGVYFCQQSFSWPLTFGAGTKL ELK | 4 |
| 63-A11(D5)B4 VH | QVQLQQPGAELVKPGASVKMSCRTSGYTFITYNMHWVKQTPGQGREWIGAIY PGNGDTSYNQKFKGKATLTADKSSSTAYMQLNSLTSEDSAVYYCSISTIITT GAVDYWGQGTSVTVAS | 5 |

TABLE 1-continued

VH/VL sequence of the lead murine antibodies

| Antibody chain | Sequence (CDRs are underlined) | SEQ ID NO: |
|---|---|---|
| 63-A11(D5)B4 VL | DIVMTQSHKFMSTSVGDRVSITCKASQDVGTAVAWYQQKAGQSPKLLIYWTS TRHTGVPDRFTGSGSGTDFTLIIRSLQSEDLADYFCQQYSRIPLTFGSGTKL EIK | 6 |
| 91-C9F1 VH | EVQLQQSGPELVKPGTSVKISCKTSGFFFTEYIIHWVKQSHGRSLEWIGGII PNNGVTNYKQNFRGKAALTADKSSNTAYMELRSLTSEDSAVYYCARWRNGYY SAMDSWGQGTSVTVSS | 7 |
| 91-C9F1 VL | DIVVTQSHKFMSTSLGDRVSITCTASQDVGTAVAWYQQKPGHSPKLLIYWAS TRHTGVPERFTGSGSGTDFTLTITNVQSEDLADYFCQQYRTSPLTFGVGTKL ELK | 8 |
| 7-F4C4 VH | QVQLQQPGAELVKPGASVKMSCKASGYTFTSYNIHWVKQTPGQGLEWIGAVY PGNGDTSYNQKFRGKATLTSDKSSNTAYMQLSSLTSEDSAVFYCARGIYGHG AMDSWGQGTSVTVSS | 9 |
| 7-F4C4 VL | DIVMTQSHKFMSTSLGARVSITYKASQDVGTAVAWYQQKPGQSPKLLIYWAS TRHTGVPDRFTGSGSGTDFTLTISNVQSEDLADYFCQQYSSNPLTFGAGTKL ELK | 10 |
| 94-B10A8 VH | QVQLQQTGAELVKPGASVKMSCKASGYTFTGYIIHWIKQRPGQGLEWIGAIY PGNGDTSYNQKIKGRATLTADKSSTTAYMQLSSLTSEDSAVYYCARGDYGNP AWFAYWGQGTLVTVSA | 11 |
| 94-B10A8 VL | DVVLTQSPATLSVTPGDRVSLSCRASQSISNYLYWYQQKAHESPRLLIKFAS QSISGIPSRFRGSGSGTDFTLSINSVETEDFGMYFCQQSNKWPLTFGAGTKL ELK | 12 |
| 94-E9B12 VH | QVQLQQPGAELVKPGASVKMSCKASGYTFTSYNMQWVKQTYGQGLEWIGAIS PGSGETSYNQNFKVKATLTADKISSTAYMQLSSLTSEDSAVYYCARAARAEG WFAYWGQGTLVTVSA | 13 |
| 94-E9B12 VL | DIVMTQSHKFMSTSVGDRVSITCKASQDVGHAVVWYQQKPGQFPKLLIYWAS TRHAGVPDRFTGSGSGTDFTLTISNVQSEDLADYFCQQFRSIPLTFGSGTKL EIK | 14 |
| 67-C9G11 VH | DVKLVESGGGLVKLGGSLKLSCAASGFTFSSYFMSWIRQTPEKRVDLVAVIN SNGGSTYSPDTVKGRFTISRDNAKNTLYLQMTSLKSEDTALYYCARHFYSYD GAWFPYWGQGTLVTVSA | 15 |
| 67-C9G11 VL | DIVMTQSHKFMSTLVGDRVSITCKASQDVSTSVAWYQQKPGQSPKLLIYWAS TRHTGVPDRFTGSGSGTDFTLTISSVQAEDLALYYCQQHHSTPITFGVGTKL ELK | 16 |
| 90-G10H7 VH | QVQLQQPGAVLVKPGASVKMSCKASGYTFTSYIIHWVKQTPGQGLEWVGAIY PGNGDASSIQKFKGKATLTVDKSSTAYMQLSSLTSADSAVYYCARGHYYGS AAWFAYWGQGTLVTVSA | 17 |
| 90-G10H7 VL | DILLTQSPAILSVSPGERVSFSCRASQNIGTGIHWYQQRINGSLRLLIKYAS ESISGIPSRFSGSGSGTDFTLSINSVESEDIADYYCQQSNSWPLTFGAGTKL ELK | 18 |
| 11-F6H8 VH | EVQLQQSGPELVKPGASVKISCKTSGFTFTEYTMHWVKQSHGKSLEWIGGIN PNNGISSYNQNFKGKATLTVDKSSTAYMELRSLTSEDSTVYYCARCRYYDT SYYDMDYWGQGTSVTVSS | 19 |
| 11-F6H8 VL | DIQMTQTTSSLSASLGDRVTISCRASQDIRNFLNWYQQKPDGTVKLLIYYTS RLHSGVPSRFSGSGSGTDYSLTISNLEEEDIATYFCQQSNTLPWTFGGGTKL EIK | 20 |
| 84-F2D10 VH | QVQLQQPGAVLVKPGASVKMSCKASGYTFTSYNLHWVKQTPGQGLEWIGAIY PGNGDTSYIQKFKGKATLTADKSSTAYMQLSSLTSEDSAVYYCARGKYGNY EGFAYWGQGTLVTVSA | 21 |
| 84-F2D10 VL | DILLTQSPAILSVSPGERVSISCRASQSIGTSIYWYQQRRNGSPRLLIKFAS ESISGIPSRFSGSGSGTDFTLSINSVESEDIADYYCQQNNRWPFTFGSGTKL EIK | 22 |
| 26-C5D2 VH | QVQLLQPGAELVKPGASVLMSCKTSGYTFTTYNMHWVKQTPGQGLEWTGVIS PGNGATSYTQKFKGKATLTADKSSNTVYMQLRSLTSEDSAVYNCARYGNTG AMDHWGQGTSVTVSS | 23 |
| 26-C5D2 VL | DIVMTQSHKFISTSVGERVIITCKASQDVGTAVTWYQRKPRQSPKLLISWAS TRHTGVPDRFTGSGSGTDFTFTINNVQSEDLADYFCQQYRAIPLTFGAGTKL ELK | 24 |

TABLE 1-continued

VH/VL sequence of the lead murine antibodies

| Antibody chain | Sequence (CDRs are underlined) | SEQ ID NO: |
|---|---|---|
| 7-G10E11 VH | DVKLVESGGGLIKLGGSLKLSCAASGFTFSGYYMSWFRQTPEKRLELVAVIN SNGGSTYYAVTVKGRFTISRDNAKNTLYLQMSSLKSEDTALYYCARHEGSQA WFAHWGQGTLVTVSA | 25 |
| 7-G10E11 VL | DIVMTQSHKFMSTSVGDRVSITCKASQDVTTAVAWYQQKPGQSPKLLIYWAS TRHTGVPDRFTGSGSGTDYTLTISSVQAEDLALYYCQQHHSTPLTFGAGTKL ELK | 26 |
| 25-B11B9 VH | DVKLVESGGGLVRLGGSLKLSCAASGFTFSSHYMSWVRQTPKKRLELVATIN SSGGNTYYPDTVKGRFTISRDNARTLFLQMTSLKSEDTALYYCARQPINTV AYFDYWGQGTTLTVSS | 27 |
| 25-B11B9 VL | DIVMTQSHEFMSTSVGARVSITCKASQDLTTAVAWYQQKPGQSPKLLIYWAS TRHIGVPDRFTGSGSGADYTLTISSVQAEDLALYYCQQYHSTPLTFGAGTKL ELK | 28 |
| 62-C10(B3)D2 VH | QVHQQQSGPELVKPGASVRISCKASGYTFTSYYIHWVKQRPGQGLEWIGCIY PGNLFTKYNEKFKDKATLTADTSSTTAYMHLSSLTSEDSAVYFCARFLNWNA WYFDVWGAGTTVSVSS | 29 |
| 62-C10(B3)D2 VL | DVLMTQTPLSLPVSLGDQASISCRSSQSIEHSNGNTNLEWYLQKPGQSPRLL IYKVSNRFSGVPDRFSGSGSGTDFTLKITGVEAEDLGVYYCFQGSHFPWTFG GGTKLEIK | 30 |
| 55-E5(B6)D12 VH | QVQLQQSGAEVVNSGASVKMSCKASGYTFTTYNMHWVKQTPGQGLEWIGAIY PGNGDTSYNQRFKGKATFTADRSSGTAYMQLSSLPSEDSAVYYCARGGYANG ALVDWGQGTLVTVSA | 31 |
| 55-E5(B6)D12 VL | DILMTQSHKFMSTSVGDRVTITCKASQDVGTAVAWYQNKPGQSPKLLIFWTS TRHTGVPDRFTGSGSGTDFTLTISNVQSEDLADYFCQQYSRQPLTFGPGTKL EIK | 32 |
| 28-G3(C6)B9 VH | QVQLQQPGAEVVKPGASVKMSCKASGYTFTSYIIHWVKQAPGQGLEWIGAIY PGNGDTSYSQRFKGKAKLTADKSSSTAYMQLNSLTSEDSVVYYCARGNNYGS PAWFGYWGQGTLVTVSA | 33 |
| 28-G3(C6)B9 VL | DIVLTQSPVTLSVTPGDRVSLSCRASQSIGNFLYWYQQKSHESPRLLIKYAS QSMSGIPSRFSGSGSGTDFTLSISRVETEDFGMYFCQQSNSWPVTFGAGTKL ELK | 34 |
| 18-G1H4 VH | QVQLQQPGAELVKPGASVRMSCKASAYTFTTYNLHWVKQTPGQGLEWIGAIS PGNGVTSYNQKFRGKATLTADKSSSTAYMQLSSLTSEDSAVYYCARYGYSV GAMDYWGQGTSVTVSS | 35 |
| 18-G1H4 VL | DIQMTQTTSSLSASLGDRVNISCSASQGIGNFLNWYQQKPDGTVKLLIYYTS SLHSGVPPRFSGSGSGTDYSLTISNLEPEDIATYYCQQYHKLPLTFGAGTKL ELK | 36 |
| 16-E5D10 VH | QVQLQQPGAENQKPGASVMMSCKASGYTFSNHNLHWLKKTPGQGLDWIGAIY PGNGDTSYNQKFKGRATLTVDKSSNTAYMQFSSLTSEDSAVFYCARKYGNG AMDYWGQGTAVTVSS | 37 |
| 16-E5D10 VL | DIVMTQSHKFMSTSVGDRVSITCRASQDVGTAVVWYQQKLGQSPKLLFDWAS SRHTGVPDRFTGSGSGTDFTLTITDVQSEDLADYFCQQYSRQPLTFGAGTKL ELK | 38 |
| 69-B11D8 VH | EVQLQQSGPELVKPGAAVKISCKTSGYTFTDYTMHWVRQSHGKSLEWIGGIH PNNGGTGYNQKLRGKATLTVDKSSSTAYMELRSLTSDDSAVYYCARGRESDG WFTYWGQGTLVTFSA | 39 |
| 69-B11D8 VL | DVHMTQTTSSLSASLGDRVTITCSASQGIGNSLNWYQQPDGTVKLLIYYTS RLHSGVPSRFSGSGSGTDYSLTISNLEPEDLATYYCQQYSRFPPTFGGGTKL EIK | 40 |
| 71-F7D4 VH | DVKLVESGGDLVKLGGSLKLSCAASGFTFSNYYMSWVRQTPEKRLELVAVIN SNGGTTYYPDNMKGRFTISRDNAKNTLYLQTSSLKSEDTALYYCGRHEHYYG TNIAWFAYWGQGTLVTVSA | 41 |
| 71-F7D4 VL | DIVMTQSHKFMSTSVGDRVSITCKASQDVTTAVAWYQQKPGQSPKLLIYWAS TRHTGVPDRFTGSGSGTDHTLTISSVQAEDLALYYCQQHYSTPVTFGGGTKL EIK | 42 |

TABLE 1-continued

VH/VL sequence of the lead murine antibodies

| Antibody chain | Sequence (CDRs are underlined) | SEQ ID NO: |
|---|---|---|
| 78-D1B10 VH | QVQLQQPGADLVKPGASVKLSCKASGFTFTSYIIHWVKQTPGQGLEWIGAIY PGNGDTSYIQKFKGRATLTADKSSTTAYMQLGGLTSEDSAVYYCARGTYGSS AWFVYWGQGTLVTVSA | 43 |
| 78-D1B10 VL | DIVLTQSPATLSVTPGDSVSLSCRASQSISNNLYWYQQKSHESPRLLIKYAS QSISGIPSRFRGSGSGTDFTLSINSVETEDFGMYFCQQSNSWPLTFGAGTKL ELK | 44 |
| 87-H12B7 VH | QVQLQQPGAEVVRPGASVKMSCKASGYTFTSYIVHWVKQPPGQGLEWIGAIY PGNGDTSYIQKFKGRATLTADKSSSTVYMQLSSLTSEDSAVYYCARGHYYGS AAWFGFWGQGTLVTVSA | 45 |
| 87-H12B7 VL | DILLTQSPAILSVSPGERVSFSCRASQNIGTSIHWYQQRTNDSPRLLMRYAS ESVSGIPSRFSGSGSGTDFTLSINSVESEDIADYYCQQSNTWPLTFGAGTKL ELK | 46 |
| 20-H2F1 VH | EVKLVESGGNLVKPGGSLKLSCAASGFTFSSYAMSWVRQTPEKRLEWVASIS NGGTTYYPDSVKGRFTISRDVARNILYLQMTSLRSEDTAMYYCARTHYRDFV YWGQGTLVTVSA | 47 |
| 20-H2F1 VL | EIVLTQAAFSNPVTLGTSASISCRSSKSLLHSNGITYLYWYLQKPGQSPQLL IYQMSNLASGVPDRFSCSGSGTDFTLRISRVEAEDVGVYYCAQNLEFPWTFG GGTKLEIK | 48 |
| 95-H11A1D8 VH | QVQLQQPGAELVKPGASVKMSCKTSGYTFTTNNMHWVKQTPGQGLEWIGAIY PGNGATAYNQKFKGKATLTADKSSSTAYMQLSSLTSEASAVYYCARGMYGHG AMDYWGQGTSVIVSS | 49 |
| 95-H11A1D8 VL | DIVLTQSPATLSVTPGDSVSLSCRARQNIGNNLYWYQQKSNESPRLLIKYAS QSISGIPSRFSGSGSGTDFTLTINSVETEDFGVYFCQQSFSWPLTFGAGTKL ELK | 50 |

Example 2. FACS Binding of Chimeric Abs to Human SLC34A2

In this example, cell based binding of chimeric antibodies (hIgG1) prepared from the murine antibodies on human SLC34A2 expressing cells were assessed using flow cytometry.

Briefly, OVCAR3 cells or HEK293 cells expressing human SLC34A2 were incubated with chimeric antibodies (from 200 nM, 4 folds dilution, 8 points). After incubation at 4° C. for 60 minutes, the cells were washed with FACS buffer twice, then stained with fluorescent conjugated secondary antibody at 4° C. for 30 minutes. After that the cells were washed twice and analyzed by flow cytometry.

The results of the study (FIGS. 1A-B and 2A-B and Tables 2-3) showed that all chimeric antibodies can bind to human SLC34A2 with high affinity, except for the slight decline of chimeric 62-C10(B3)D2 and 95-H11A1D8 at highest concentrations, compared with reference antibody XMT-1536.

TABLE 2

Binding Affinity of Chimeric Antibodies to OVCAR3 Cells

| | $EC_{50}$ (nM) | Top (MFI) |
|---|---|---|
| Antibody (1st Batch) | | |
| xi7F4C4 hIgG1 | 4.49 | 39014 |
| xi94B10A8 hIgG1 | 1.57 | 39619 |
| xi94E9B12 hIgG1 | 11.01 | 46222 |
| xi67C9G11 hIgG1 | 4.67 | 41042 |
| xi90G10H7 hIgG1 | 2.14 | 43252 |

TABLE 2-continued

Binding Affinity of Chimeric Antibodies to OVCAR3 Cells

| | $EC_{50}$ (nM) | Top (MFI) |
|---|---|---|
| xi11F6H8 hIgG1 | 4.90 | 41330 |
| xi84F2D10 hIgG1 | 3.84 | 40519 |
| xi26C5D2 hIgG1 | 1.99 | 34227 |
| xi7G10E11 hIgG1 | 1.68 | 39625 |
| xi25B11B9 hIgG1 | 9.06 | 42516 |
| xi62C10B3D2 hIgG1 | 408.50 | 29476 |
| xi55E5B6D12 hIgG1 | 3.31 | 42934 |
| xi28G3C6B9 hIgG1 | 4.27 | 42993 |
| xi30H9B8F9 hIgG1 | 0.53 | 41946 |
| xi62G10E4G8 hIgG1 | 2.55 | 43000 |
| xi63A11D5B4 hIgG1 | 3.85 | 42986 |
| xi18G1H4 hIgG1 | 2.75 | 42473 |
| hIgG1 Isotype | ~2895 | ~1566 |
| XMT-1536 | 4.31 | 40189 |
| Antibody (2nd Batch) | | |
| xi16E5D10 hIgG1 | 4.66 | 27607 |
| xi69B11D8 hIgG1 | 2.12 | 27681 |
| xi71F7D4 hIgG1 | 7.86 | 28910 |
| xi78D1B10 hIgG1 | 2.52 | 27502 |
| xi91C9F1 hIgG1 | 1.64 | 26417 |
| xi87-H12B7 hIgG1 | 5.43 | 27824 |
| xi20H2F1 hIgG1 | 2.73 | 26495 |
| xi95H11A1D8VH-1 hIgG1 | NA | NA |
| hIgG1 Isotype | NA | NA |
| XMT-1536 | 3.99 | 26673 |

TABLE 3

Binding Affinity of Chimeric Antibodies to HEK293 cells expressing human SLC34A2

| | $EC_{50}$ (nM) | Top (MFI) |
|---|---|---|
| Antibody (1st Batch) | | |
| xi7F4C4 hIgG1 | 2.27 | 88468 |
| xi94B10A8 hIgG1 | 1.17 | 91255 |
| xi94E9B12 hIgG1 | 2.48 | 105603 |
| xi67C9G11 hIgG1 | 2.82 | 107055 |
| xi90G10H7 hIgG1 | 1.52 | 114272 |
| xi11F6H8 hIgG1 | 1.92 | 111432 |
| xi84F2D10 hIgG1 | 1.37 | 109026 |
| xi26C5D2 hIgG1 | 1.20 | 100725 |
| xi7G10E11 hIgG1 | 1.72 | 108524 |
| xi25B11B9 hIgG1 | 2.51 | 105605 |
| xi62C10B3D2 hIgG1 | 378.40 | 127984 |
| xi55E5B6D12 hIgG1 | 1.80 | 115440 |
| xi28G3C6B9 hIgG1 | 1.88 | 106874 |
| xi30H9B8F9 hIgG1 | 0.96 | 107226 |
| xi62G10E4G8 hIgG1 | 1.28 | 100511 |
| xi63A11D5B4 hIgG1 | 1.50 | 102578 |
| xi18G1H4 hIgG1 | 0.86 | 106260 |
| XMT-1536 | — | — |
| Antibody (2nd Batch) | | |
| xi16E5D10 hIgG1 | 2.29 | 47483 |
| xi69B11D8 hIgG1 | 1.19 | 48044 |
| xi71F7D4 hIgG1 | 2.11 | 47863 |
| xi78D1B10 hIgG1 | 1.26 | 47662 |
| xi91C9F1 hIgG1 | 1.06 | 44788 |
| xi87-H12B7 hIgG1 | 1.62 | 44894 |
| xi20H2F1 hIgG1 | 1.31 | 41969 |
| xi95H11A1D8VH-1 hIgG1 | 63.4 | 12705 |
| hIgG1 | NA | NA |
| 117-BMK | 1.67 | 46062 |

Based on the foregoing cell-based binding results, some of the chimeric antibodies were selected for further cell based binding on human SLC34A2 expressing cells using flow cytometry. RMG-1 cells were incubated with the selected chimeric antibodies (from 200 nM, 4 folds dilution, 8 points). After incubation at 4° C. for 60 minutes, the cells were washed with FACS buffer twice, then stained with fluorescent conjugated secondary antibody at 4° C. for 30 minutes. Afterwards the cells were washed twice and analyzed by flow cytometry.

Figure 3:
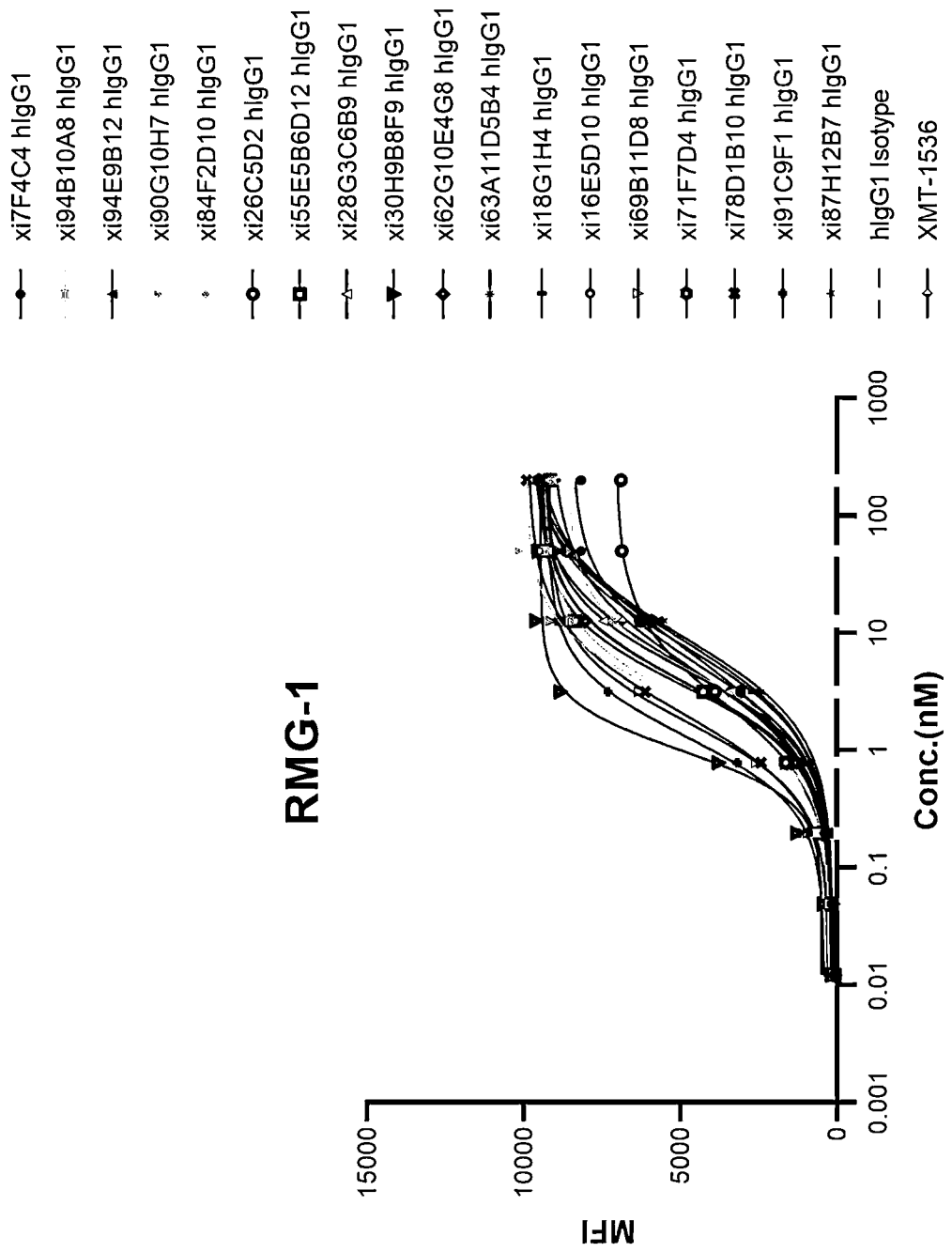
FIG. 3 shows the binding affinity of the chimeric antibodies to human SLC34A2 on RMG-1 cells.

The results of the study (FIG. 3 and Table 4) show that the chimeric antibodies can bind to human SLC34A2 with high affinity, as compared with reference antibody XMT-1536.

TABLE 4

Binding Affinity of Selected Chimeric Antibodies to RMG-1 Cells

| Antibody | $EC_{50}$ (nM) | Top (MFI) |
|---|---|---|
| xi7F4C4 hIgG1 | 5.03 | 8461 |
| xi94B10A8 hIgG1 | 2.58 | 9373 |
| xi94E9B12 hIgG1 | 9.05 | 10003 |
| xi90G10H7 hIgG1 | 2.77 | 9922 |
| xi84F2D10 hIgG1 | 4.33 | 8596 |
| xi26C5D2 hIgG1 | 2.52 | 7062 |
| xi55E5B6D12 hIgG1 | 3.48 | 9502 |
| xi28G3C6B9 hIgG1 | 4.73 | 9424 |
| xi30H9B8F9 hIgG1 | 0.99 | 9470 |
| xi62G10E4G8 hIgG1 | 3.65 | 9371 |
| xi63A11D5B4 hIgG1 | 5.32 | 9768 |
| xi18G1H4 hIgG1 | 7.91 | 9800 |
| xi16E5D10 hIgG1 | 3.76 | 9495 |
| xi69B11D8 hIgG1 | 1.70 | 9201 |
| xi71F7D4 hIgG1 | 8.36 | 10204 |
| xi78D1B10 hIgG1 | 2.10 | 9860 |
| xi91C9F1 hIgG1 | 1.30 | 9233 |
| xi87H12B7 hIgG1 | 9.11 | 9657 |
| hIgG1 Isotype | NA | NA |
| XMT-1536 | 4.87 | 9114 |

Example 3. Cross Reactivity Binding of Chimeric Abs to Rhesus and Cynomolgus SLC34A2 Proteins In this example, cell based binding of chimeric Abs on Rhesus and Cynomolgus SLC34A2 expressing cells were assessed using flow cytometry.

Briefly, the Rhesus SLC34A2 expressing HEK293 engineering cells (HEK293/Rhesus_SLC34A2) were incubated with chimeric Abs (from 200 nM, 4 folds dilution, 8 points). After incubation at 4° C. for 60 minutes, the cells were washed with FACS buffer twice, then stained with fluorescent conjugated secondary antibody at 4° C. for 30 minutes. After that the cells were washed twice and analyzed by flow cytometry.

Figure 4:
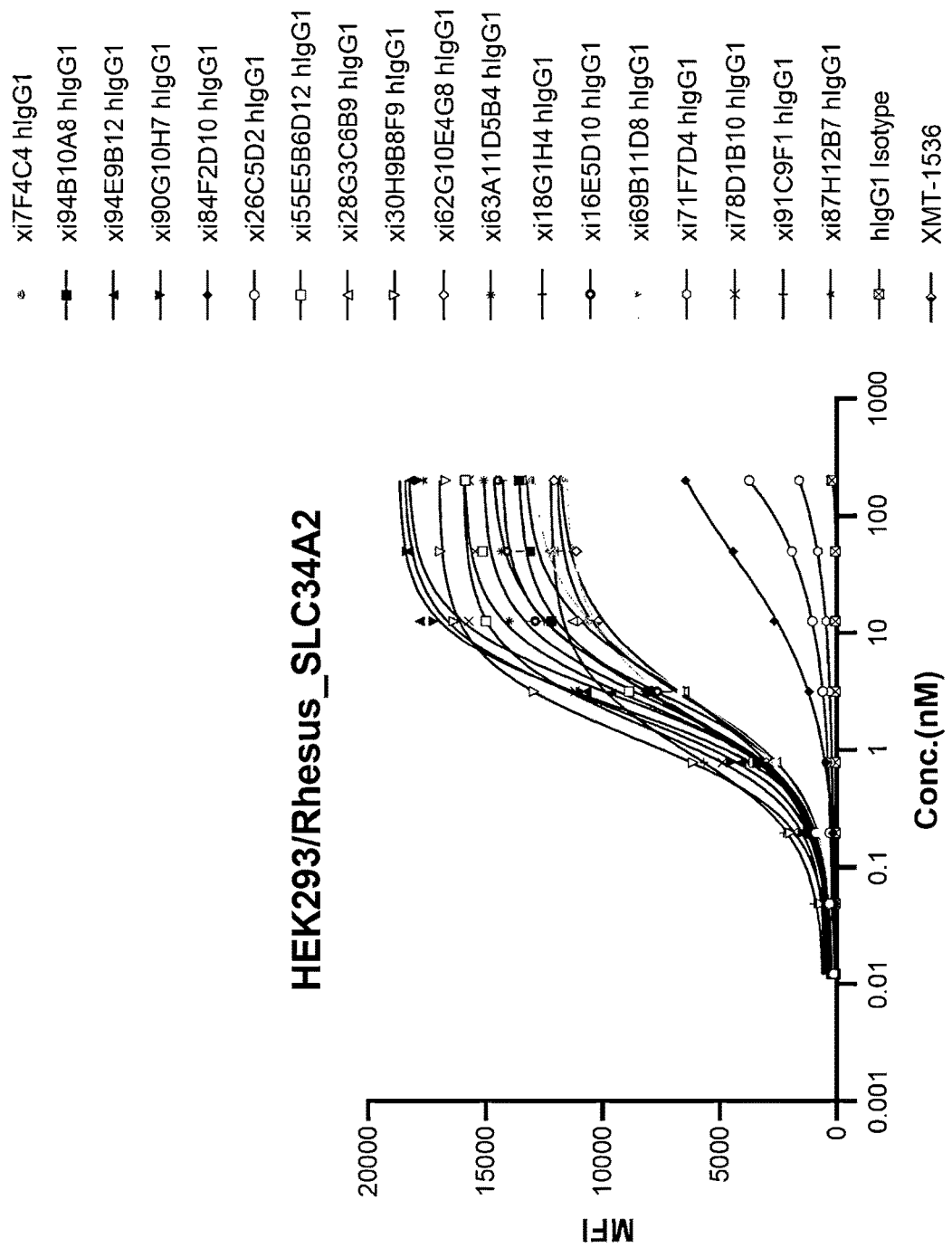
FIG. 4 shows the binding affinity of the chimeric antibodies to Rhesus SLC34A2 expressed on HEC293 cells.

The results of the study (FIG. 4 and Table 5) show that most of the chimeric Abs can bind to Rhesus SLC34A2 with high affinity.

TABLE 5

Cross Reactivity Binding to Rhesus

| Antibody | $EC_{50}$ (nM) | Top (MFI) |
|---|---|---|
| xi7F4C4 hIgG1 | 3.09 | 13074 |
| xi94B10A8 hIgG1 | 2.24 | 13671 |
| xi94E9B12 hIgG1 | 2.38 | 18712 |
| xi90G10H7 hIgG1 | 2.19 | 18502 |
| xi84F2D10 hIgG1 | 46.04 | 8844 |
| xi26C5D2 hIgG1 | NA | NA |
| xi55E5B6D12 hIgG1 | 2.46 | 15942 |
| xi28G3C6B9 hIgG1 | 3.19 | 13396 |
| xi30H9B8F9 hIgG1 | 1.26 | 17011 |
| xi62G10E4G8 hIgG1 | 2.53 | 11975 |
| xi63A11D5B4 hIgG1 | 2.56 | 15148 |
| xi18G1H4 hIgG1 | 2.90 | 14349 |
| xi16E5D10 hIgG1 | 2.72 | 14803 |
| xi69B11D8 hIgG1 | 1.68 | 11619 |
| xi71F7D4 hIgG1 | NA | ~5396799 |
| xi78D1B10 hIgG1 | 1.58 | 15959 |
| xi91C9F1 hIgG1 | 0.95 | 12220 |
| xi87H12B7 hIgG1 | 2.85 | 18333 |
| hIgG1 Isotype | NA | NA |
| XMT-1536 | 2.54 | 11913 |

Figure 5:
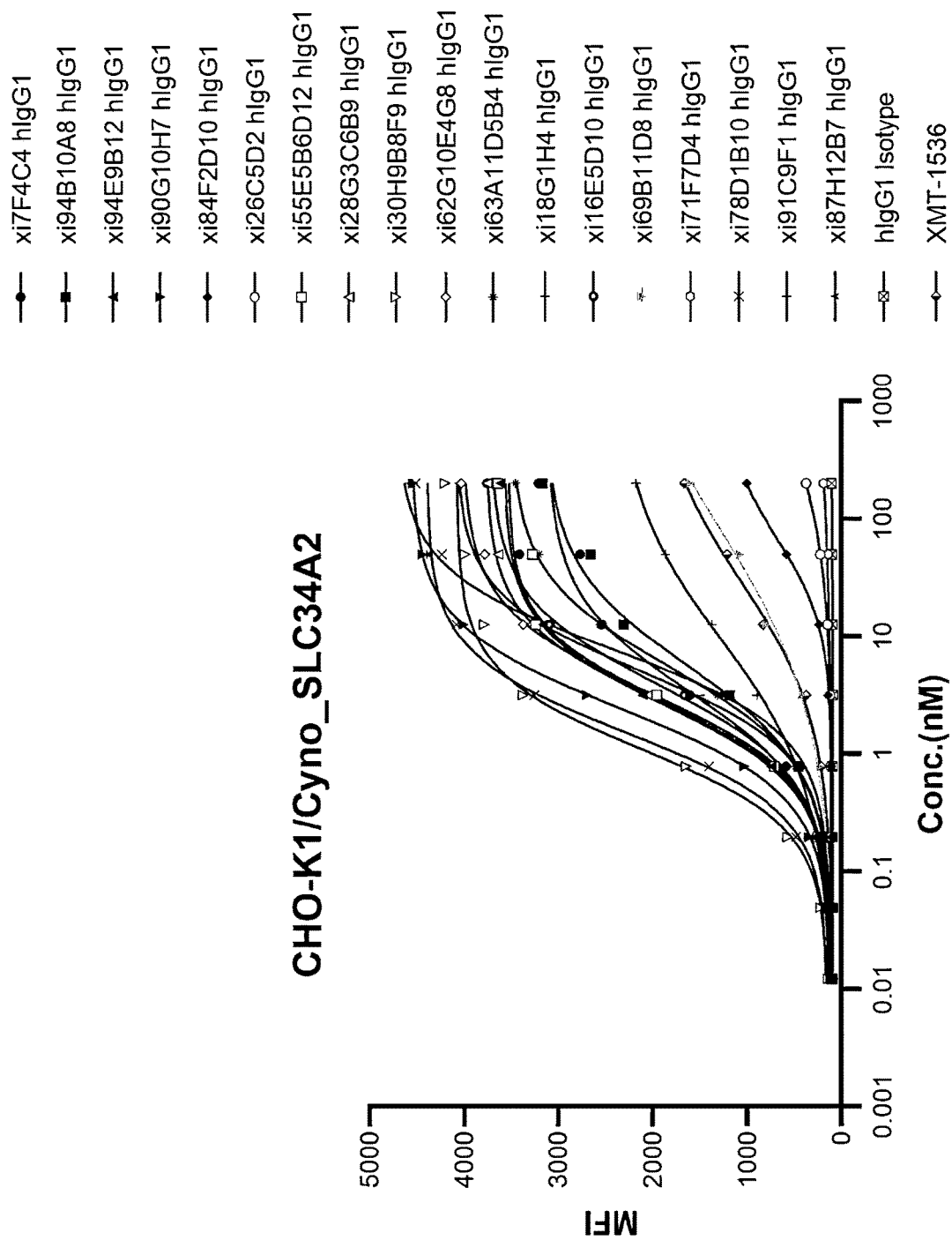
FIG. 5 shows the binding affinity of the chimeric antibodies to Cyno SLC34A2 expressed on CHC-K1 cells.

Likewise, the chimeric antibodies' binding to Cynomolgus SLC34A2 were measured, and the results are shown in FIG. 5 and Table 6. The results show that most of the chimeric Abs can bind to Cynomolgus SLC34A2 with high affinity.

TABLE 6

Cross Reactivity Binding to Cynomolgus

| Antibody | $EC_{50}$ (nM) | Top (MFI) |
|---|---|---|
| xi7F4C4 hIgG1 | 3.30 | 3121 |
| xi94B10A8 hIgG1 | 5.47 | 3149 |
| xi94E9B12 hIgG1 | 2.51 | 3579 |
| xi90G10H7 hIgG1 | 2.40 | 4561 |
| xi84F2D10 hIgG1 | 68.46 | 1275 |
| xi26C5D2 hIgG1 | 945.60 | 1208 |

TABLE 6-continued

Cross Reactivity Binding to Cynomolgus

| Antibody | EC$_{50}$ (nM) | Top (MFI) |
|---|---|---|
| xi55E5B6D12 hIgG1 | 2.70 | 3541 |
| xi28G3C6B9 hIgG1 | 2.81 | 3772 |
| xi30H9B8F9 hIgG1 | 1.08 | 4079 |
| xi62G10E4G8 hIgG1 | 3.33 | 4016 |
| xi63A11D5B4 hIgG1 | 5.33 | 3508 |
| xi18G1H4 hIgG1 | 4.93 | 4086 |
| xi16E5D10 hIgG1 | 3.79 | 3728 |
| xi69B11D8 hIgG1 | 88.35 | 2566 |
| xi71F7D4 hIgG1 | NA | NA |
| xi78D1B10 hIgG1 | 1.50 | 4398 |
| xi91C9F1 hIgG1 | 9.11 | 2434 |
| xi87H12B7 hIgG1 | 7.66 | 4711 |
| hIgG1 Isotype | NA | NA |
| XMT-1536 | 29.31 | 2052 |

Example 4. Cross Reactivity Binding to Rat SLC34A2 Protein

In this example, cell based binding of chimeric Abs on rat SLC34A2 expressing cells were assessed using flow cytometry.

Briefly, the rat and mouse SLC34A2-expressing HEK293 engineering cells (HEK293/Rat_SLC34A2, HEK293/Mouse_SLC34A2) were incubated with chimeric Abs (10 ug/ml). After incubation at 4° C. for 60 minutes, the cells were washed with FACS buffer twice, then stained with fluorescent conjugated secondary antibody at 4° C. for 30 minutes. After that the cells were washed twice and analyzed by flow cytometry.

Figure 6A:
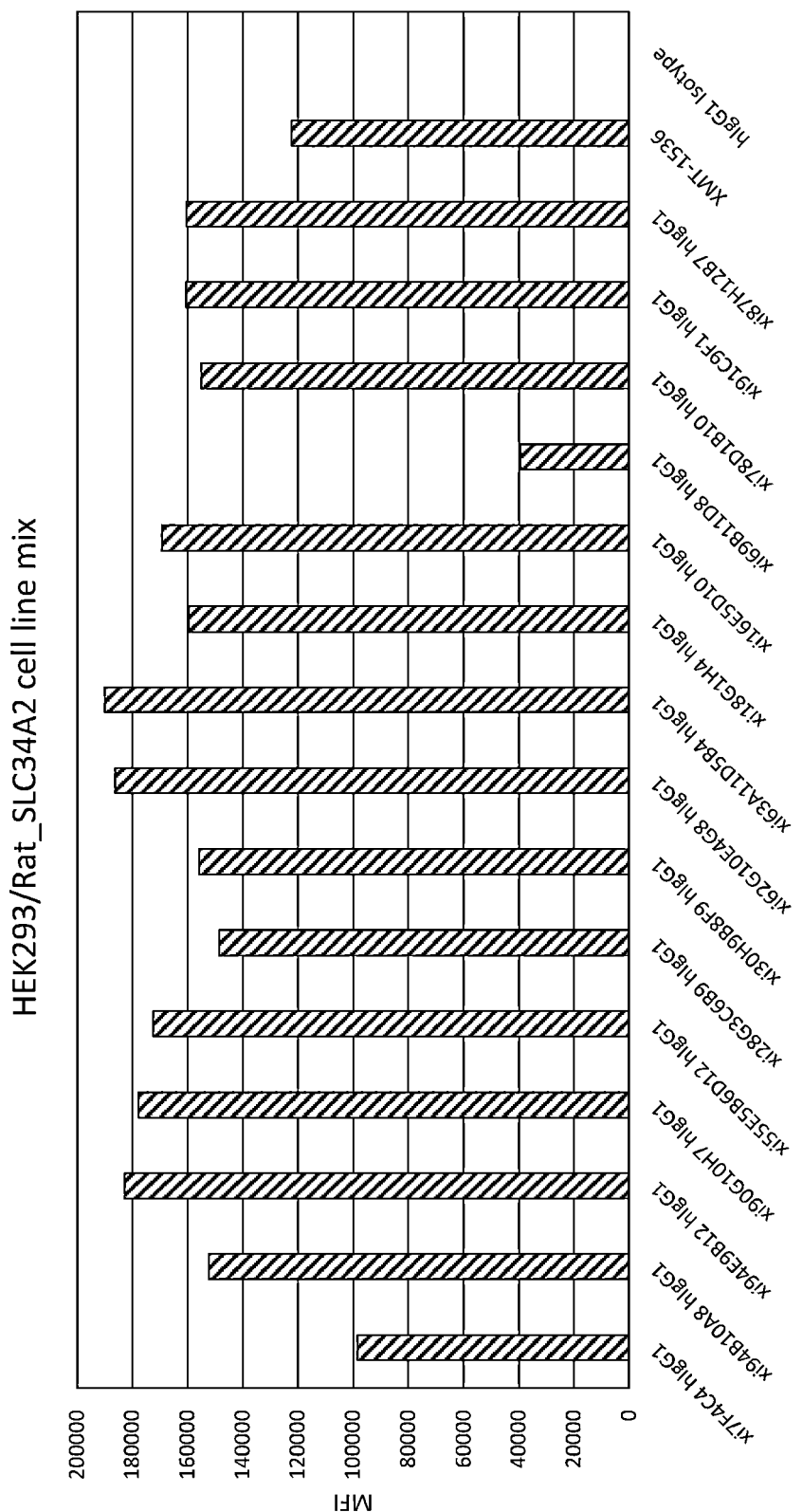
FIG. 6A-B show the binding affinity of the chimeric antibodies to rat (6A) and mouse (6B) SLC34A2 expressed on HEC293 cells.
Figure 6B:
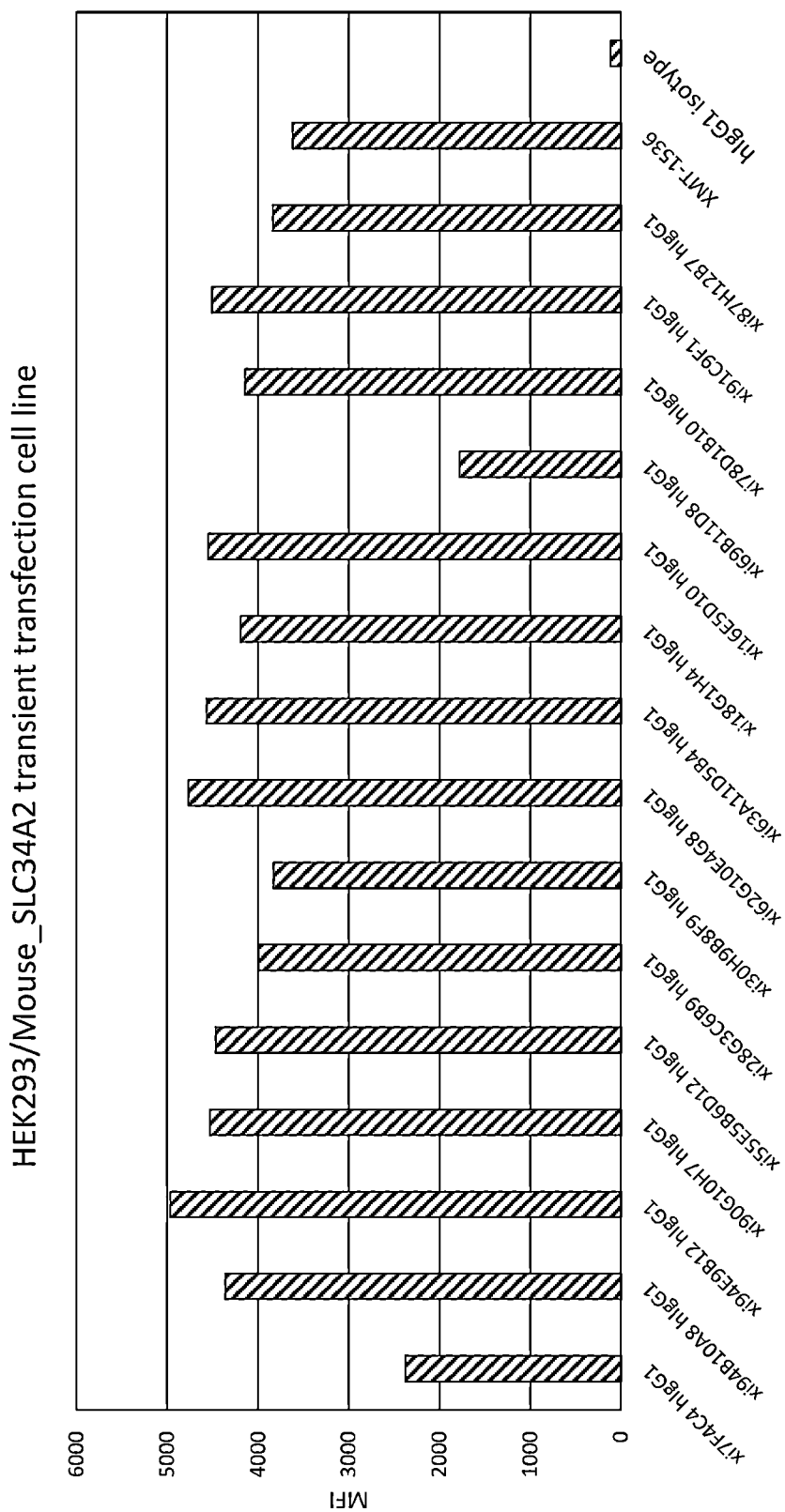

The results of the study (FIG. 6A-B) show that most of the chimeric Abs can bind to rodent SLC34A2 with high affinity.

Example 5. ADCC Against Human SLC34A2-Expressing Cells

This example evaluated the chimeric antibodies' ability to induce antibody-dependent cytotoxic activities.

The ADCC Reporter Bioassay employed here uses an alternative readout at an earlier point in ADCC MOA pathway activation: the activation of gene transcription through the NFAT (nuclear factor of activated T-cells) pathway in the effector cell. In addition, the ADCC Reporter Bioassay uses engineered Jurkat cells stably expressing the FcγRIIIa receptor, V158 (high affinity) variant, and an NFAT response element driving expression of firefly luciferase as effector cells. Antibody biological activity in ADCC MOA is quantified through the luciferase produced as a result of NFAT pathway activation; luciferase activity in the effector cell is quantified with luminescence readout. Signal is high, and assay background is low.

Figure 7A:
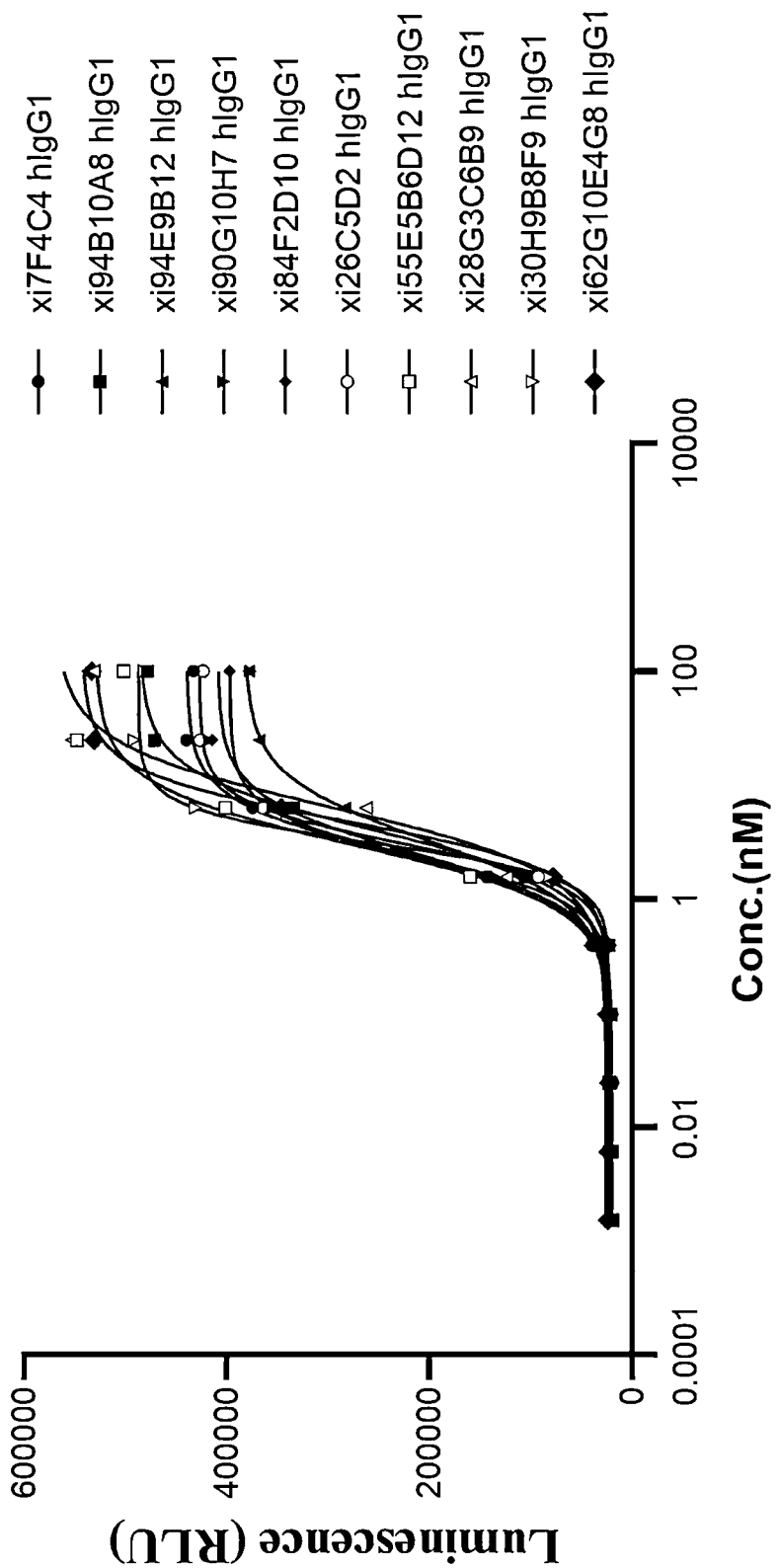
FIG. 7A-B show the ADCC activity of the chimeric antibodies against HEC293 cells expressing human SLC34A2.
Figure 7B:
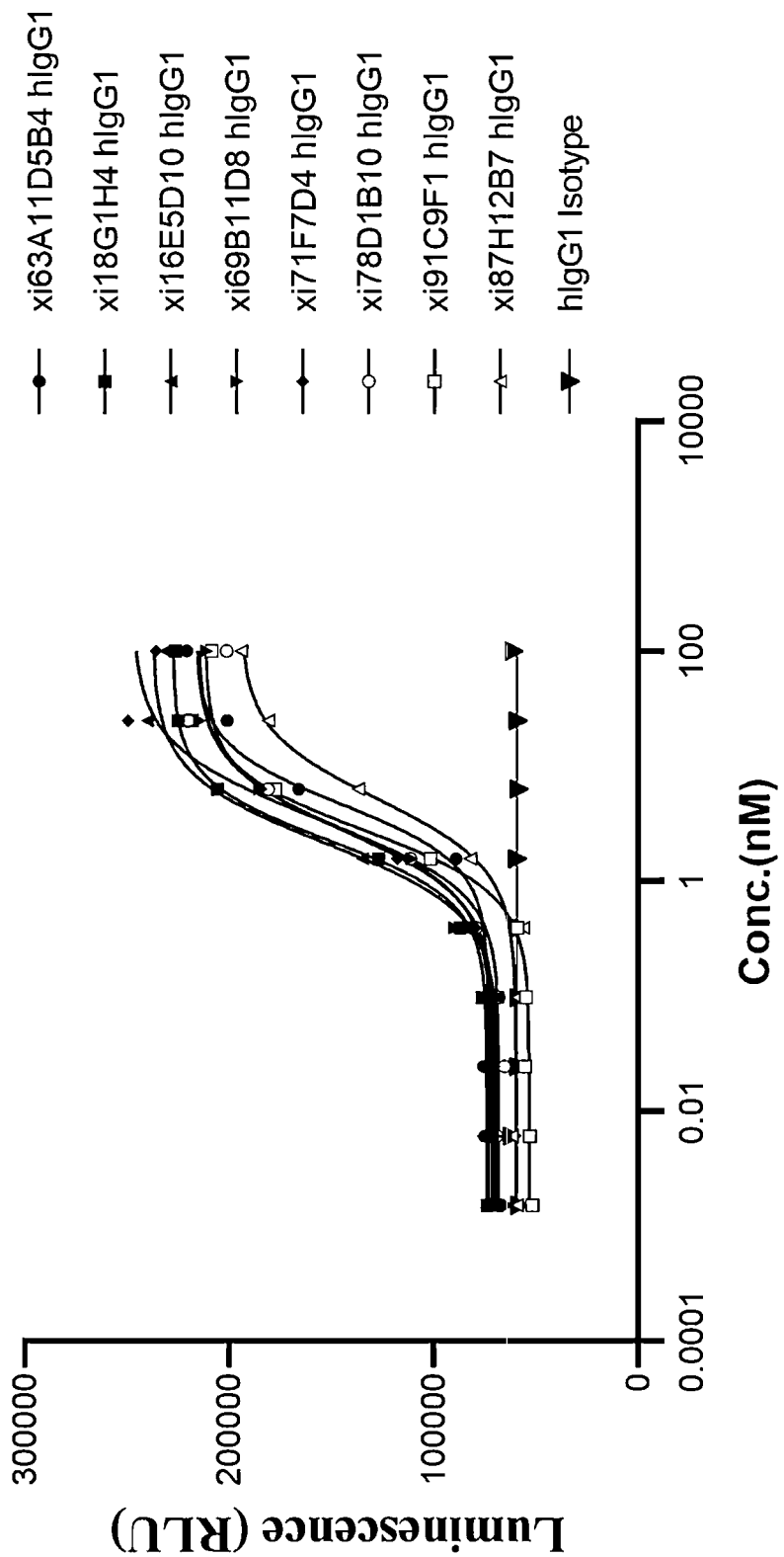

Serial dilutions of chimeric Abs were incubated for 6 hours of induction at 37° C. with engineered Jurkat effector cells (ADCC Bioassay Effector Cells), with ADCC Bioassay target Cells (expressing SLC34A2). Luciferase activity was quantified using ONE-Glo™ Luciferase Assay Buffer Reagent. The results are shown in FIG. 7A-B and Table 7. As shown, all of the tested chimeric antibodies exhibited patent ADCC induction activities.

TABLE 7

ADCC of Chimeric Antibodies

| Antibody | EC$_{50}$ (nM) | Top (MFI) |
|---|---|---|
| xi7F4C4 hIgG1 | 2.5 | 439624 |
| xi94B10A8 hIgG1 | 4.0 | 485769 |
| xi94E9B12 hIgG1 | 3.3 | 382205 |
| xi90G10H7 hIgG1 | 2.3 | 397344 |
| xi84F2D10 hIgG1 | 2.5 | 409115 |
| xi26C5D2 hIgG1 | 3.0 | 427014 |
| xi55E5B6D12 hIgG1 | 3.0 | 530043 |
| xi28G3C6B9 hIgG1 | 6.4 | 569103 |
| xi30H9B8F9 hIgG1 | 3.1 | 487349 |
| xi62G10E4G8 hIgG1 | 4.8 | 542275 |
| xi63A11D5B4 hIgG1 | 4.6 | 216320 |
| xi18G1H4 hIgG1 | 2.2 | 227773 |
| xi16E5D10 hIgG1 | 2.1 | 237571 |
| xi69B11D8 hIgG1 | 2.7 | 216267 |
| xi71F7D4 hIgG1 | 3.6 | 247281 |
| xi78D1B10 hIgG1 | 2.6 | 211795 |
| xi91C9F1 hIgG1 | 2.8 | 215229 |
| xi87H12B7 hIgG1 | 5.1 | 194715 |
| hIgG1 Isotype | NA | NA |

Example 6. Cytotoxic Effect Against Human SLC34A2-Expressing Cells

This example examined the cytotoxic effects of the chimeric antibodies.

The human SLC34A2 expressing HEK293 engineering cells (HEK293/H_SLC34A2), were seeded to a 96-well plate. The cells were treated with chimeric Abs complex at respective concentrations for 5 days. The cell viability was measured by CellTiter-Glo reagent. The luciferase activity was detected by Envison.

Figure 8A:
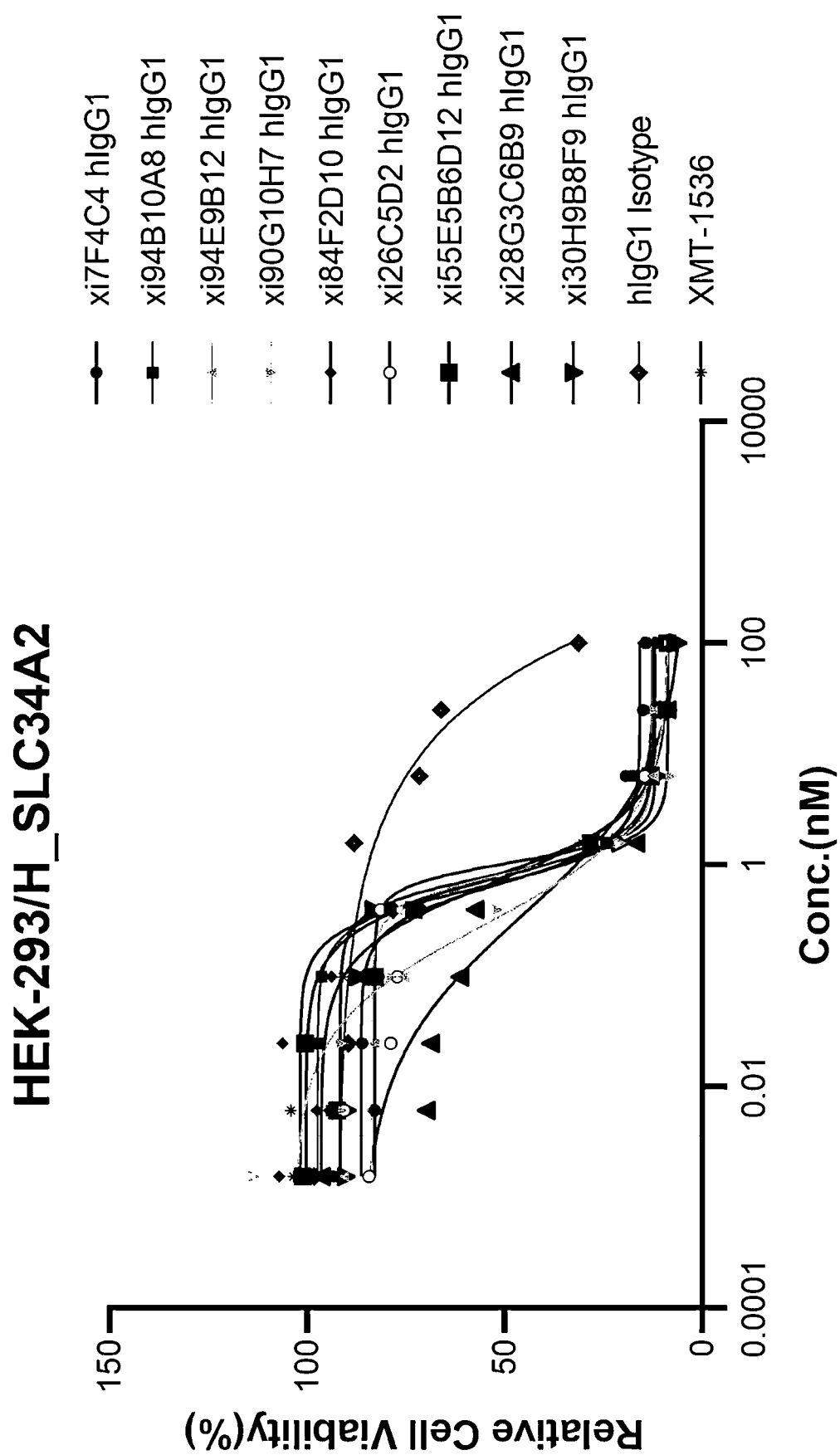
FIG. 8A-B show the cytotoxic activity of the chimeric antibodies against HEC293 cells expressing human SLC34A2.
Figure 8B:
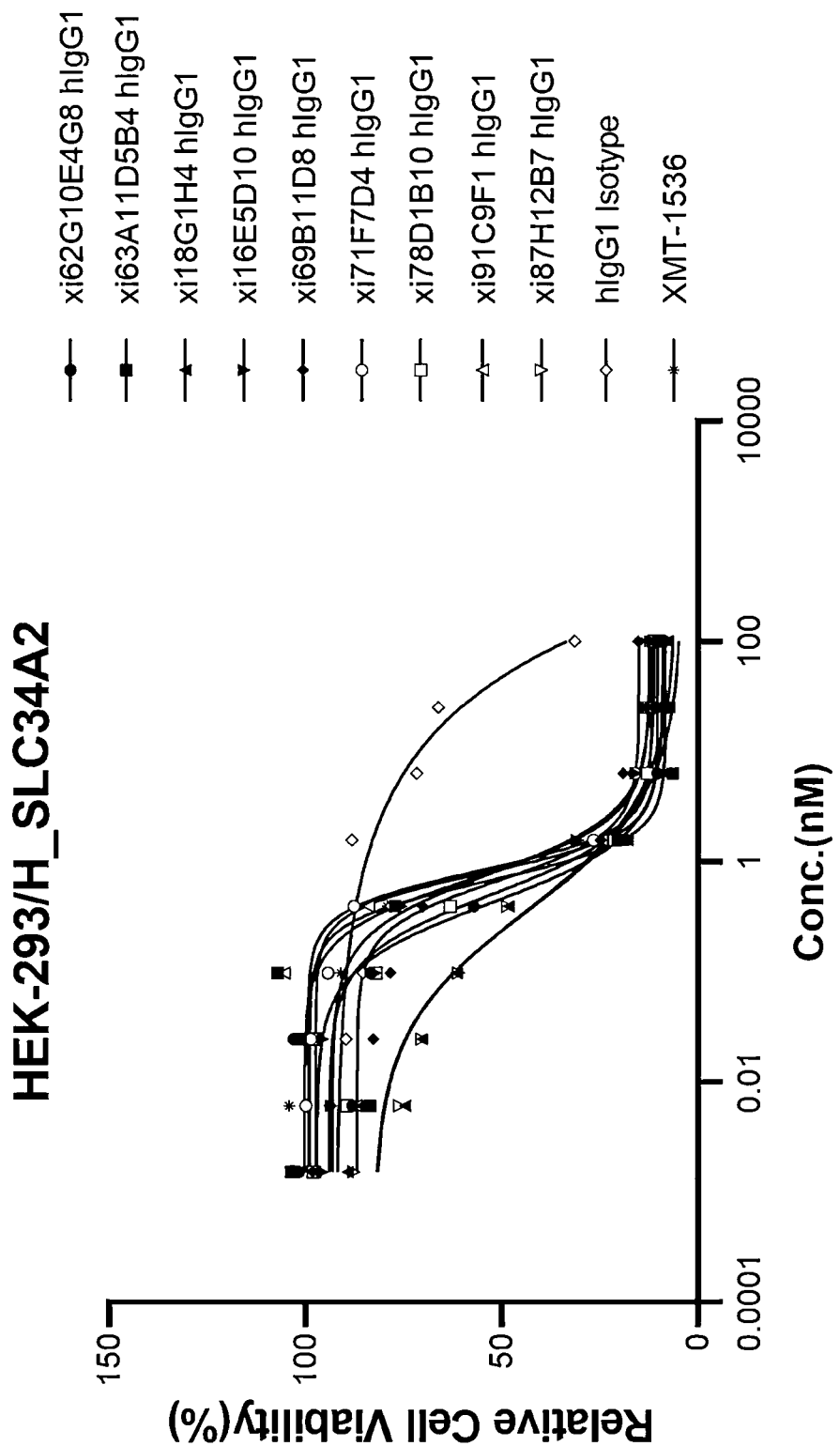

The results (FIG. 8A-B and Table 8) show that these chimeric Abs all had highly potent killing activities.

TABLE 8

Cytotoxic Activities

| Antibody | IC$_{50}$ (nM) | Inhibition % |
|---|---|---|
| xi7F4C4 hIgG1 | 0.67 | 86.5 |
| xi94B10A8 hIgG1 | 0.70 | 97.5 |
| xi94E9B12 hIgG1 | 0.85 | 83.6 |
| xi90G10H7 hIgG1 | 0.28 | 103.1 |
| xi84F2D10 hIgG1 | 0.61 | 101.9 |
| xi26C5D2 hIgG1 | 1.06 | 82.9 |
| xi55E5B6D12 hIgG1 | 0.69 | 96.7 |
| xi28G3C6B9 hIgG1 | 0.36 | 86.4 |
| xi30H9B8F9 hIgG1 | 0.84 | 91.7 |
| xi62G10E4G8 hIgG1 | 0.42 | 97.2 |
| xi63A11D5B4 hIgG1 | 0.66 | 99.0 |
| xi18G1H4 hIgG1 | 0.36 | 82.7 |
| xi16E5D10 hIgG1 | 0.78 | 93.1 |
| xi69B11D8 hIgG1 | 0.67 | 86.9 |
| xi71F7D4 hIgG1 | 0.83 | 99.4 |
| xi78D1B10 hIgG1 | 0.50 | 94.0 |
| xi91C9F1 hIgG1 | 0.80 | 97.4 |
| xi87H12B7 hIgG1 | 0.35 | 82.6 |
| hIgG1 Isotype | NA | 92.3 |
| XMT-1536 | 0.72 | 100.4 |

Example 7. Mutations to CDR to Prevent Post-Translational Modifications

Six of the murine antibodies, 90G10H7, 55E5B6D12, 30H9B8F9, 62G10E4G8, 63A11D5B4, and 91C9F1, were selected for humanization and amino acid mutations to prevent potential post-translational modifications (PTM), which are hereby referred to as a PTM-derisked sequences.

The PTM-derisked VH chains were first tested for their impact on target binding. Cell based binding of PTM Abs on human SLC34A2 expressing cells were assessed using flow cytometry. Briefly, the HEK293/H_SLC34A2 cells were incubated with PTM Abs (from 200 nM, 4 folds dilution, 8 points). After incubation at 4° C. for 60 minutes, the cells were washed with FACS buffer twice, then stained with fluorescent conjugated secondary antibody at 4° C. for 30 minutes. After that the cells were washed twice and analyzed by flow cytometry.

Figure 9A:
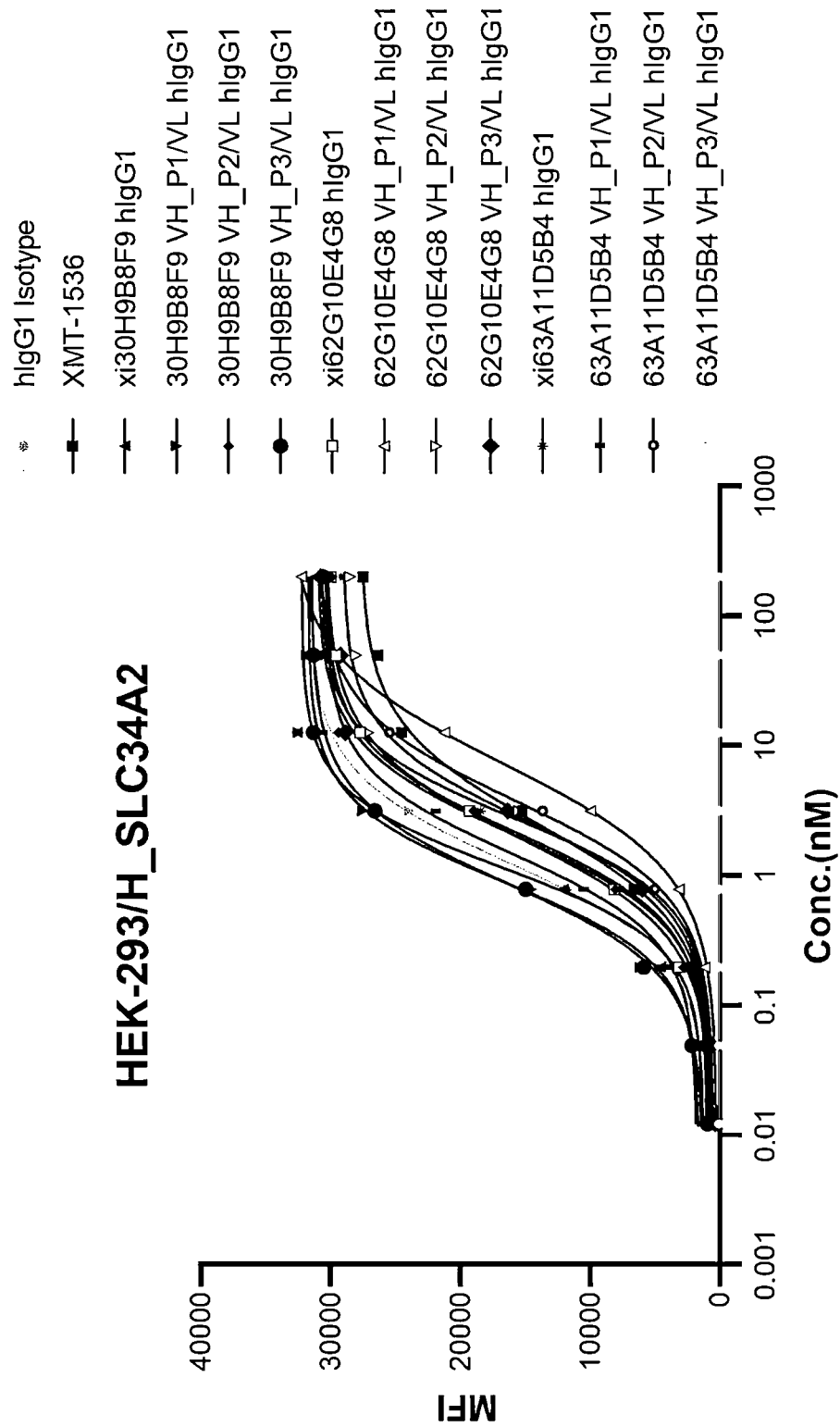
Figure 9B:
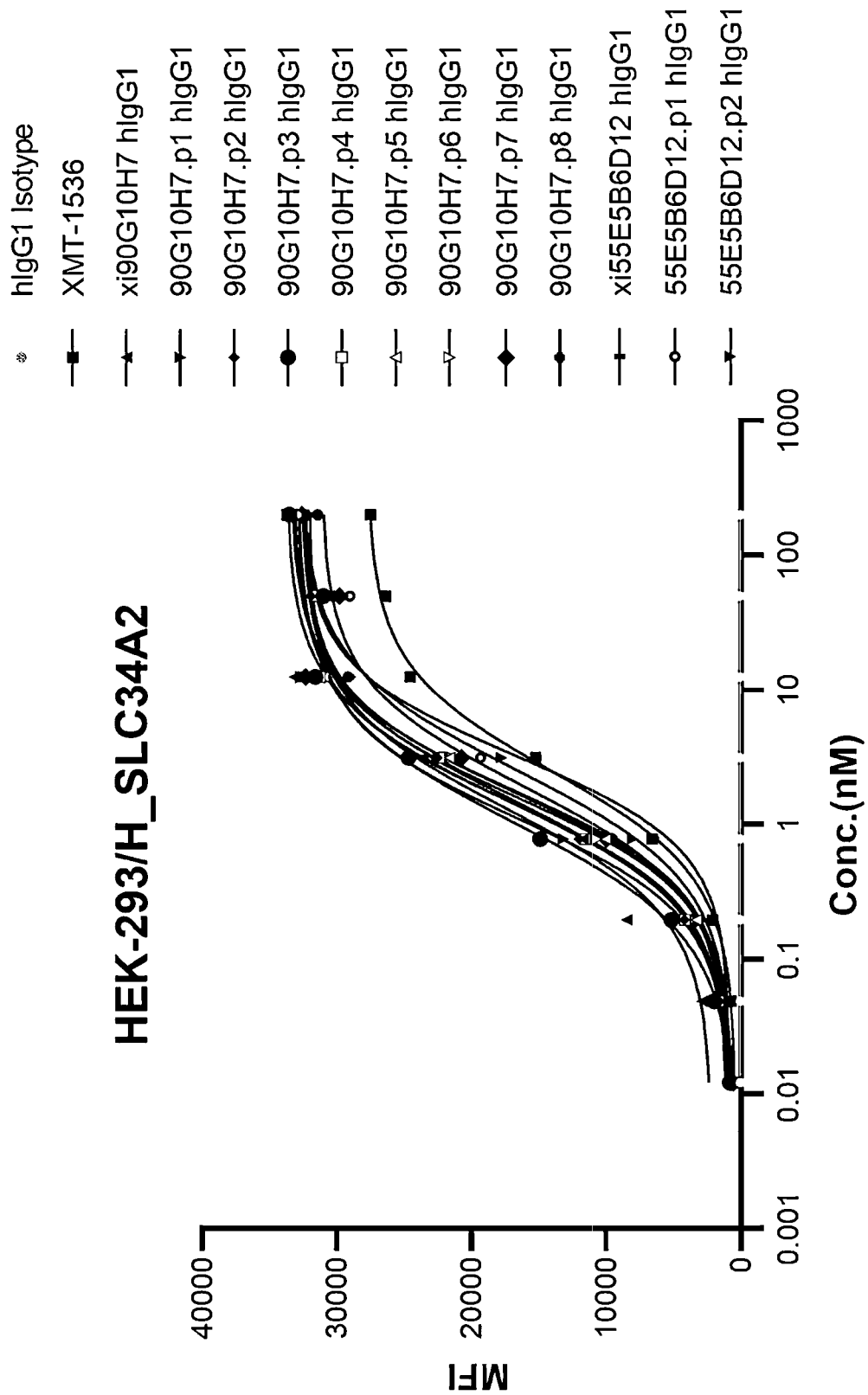

The results of the study (FIG. 9A-C and Table 9) show that the humanized/PTM-derisked antibodies can bind to human SLC34A2 with high affinity.

TABLE 9

Binding to SLC34A2-Expressing HEK293

| Antibody | EC$_{50}$ (nM) | Top (MFI) |
| --- | --- | --- |
| hIgG1 Isotype | NA | NA |
| XMT-1536 | 2.50 | 27716 |
| xi30H9B8F9 hIgG1 | 1.14 | 32228 |
| 30H9B8F9 VH_P1/VL hIgG1 | 0.89 | 31744 |
| 30H9B8F9 VH_P2/VL hIgG1 | 2.04 | 31036 |
| 30H9B8F9 VH_P3/VL hIgG1 | 0.86 | 31483 |
| xi62G10E4G8 hIgG1 | 1.95 | 30330 |
| 62G10E4G8 VH_P1/VL hIgG1 | 7.31 | 33356 |
| 62G10E4G8 VH_P2/VL hIgG1 | 2.63 | 29055 |
| 62G10E4G8 VH_P3/VL hIgG1 | 2.73 | 30766 |
| xi63A11D5B4 hIgG1 | 2.13 | 30449 |
| 63A11D5B4 VH_P1/VL hIgG1 | 1.48 | 30393 |
| 63A11D5B4 VH_P2/VL hIgG1 | 3.74 | 30993 |
| 63A11D5B4 VH_P3/VL hIgG1 | 1.26 | 31638 |
| xi90G10H7 hIgG1 | 1.14 | 32228 |
| 90G10H7.p1 hIgG1 | 0.89 | 31744 |
| 90G10H7.p2 hIgG1 | 2.04 | 31036 |
| 90G10H7.p3 hIgG1 | 0.86 | 31483 |
| 90G10H7.p4 hIgG1 | 1.95 | 30330 |
| 90G10H7.p5 hIgG1 | 7.31 | 33356 |
| 90G10H7.p6 hIgG1 | 2.63 | 29055 |
| 90G10H7.p7 hIgG1 | 2.73 | 30766 |
| 90G10H7.p8 hIgG1 | 2.13 | 30449 |
| xi55E5B6D12 hIgG1 | 1.48 | 30393 |
| 55E5B6D12.p1 hIgG1 | 3.74 | 30993 |
| 55E5B6D12.p2 hIgG1 | 1.26 | 31638 |
| xi91C9F1 hIgG1 | 1.57 | 28615 |
| 91C9F1.p1 hIgG1 | 0.68 | 28205 |
| 91C9F1.p2 hIgG1 | 2.07 | 26916 |

Figure 10:
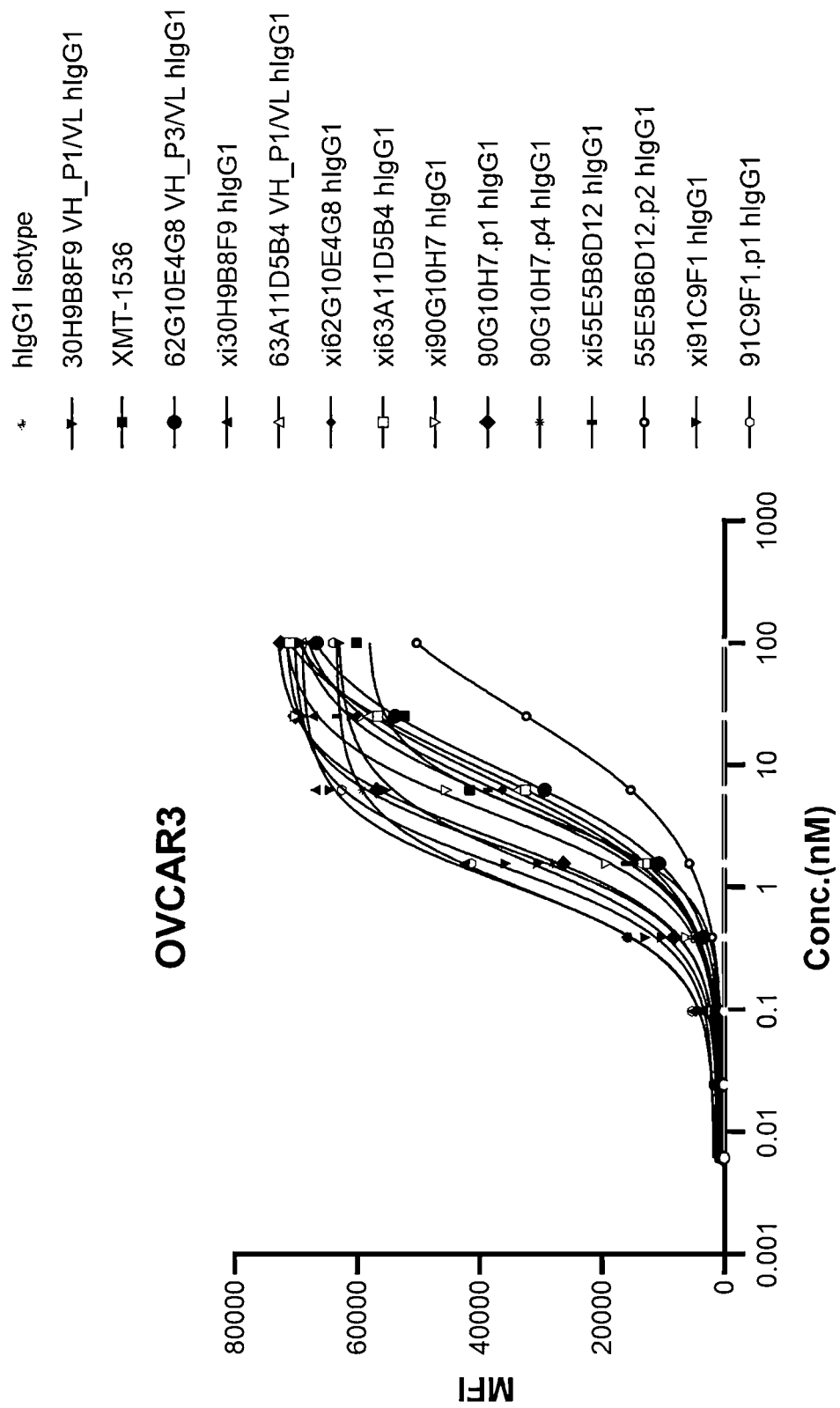
FIG. 10 shows the binding activity of the PTM-derisked antibodies to endogenously expressed SLC34A2 on OVCAR3 cells.

Similarly, these humanized/PTM-derisked antibodies' binding to OVCAR3 cells that express the protein endogenously were tested. The results are shown in FIG. 10 and Table 10. Again, the results confirmed the binding affinity of these antibodies.

TABLE 10

Binding to OVCAR3 Cells

| Antibody | EC$_{50}$ (nM) | Top (MFI) |
| --- | --- | --- |
| hIgG1 Isotype | NA | NA |
| XMT-1536 | 3.8 | 58447 |
| xi30H9B8F9 hIgG1 | 1.1 | 69144 |
| 30H9B8F9 VH_P1/VL hIgG1 | 1.5 | 70424 |
| xi62G10E4G8 hIgG1 | 5.8 | 71096 |
| 62G10E4G8 VH_P3/VL hIgG1 | 9.1 | 72506 |
| xi63A11D5B4 hIgG1 | 9.2 | 78584 |
| 63A11D5B4 VH_P1/VL hIgG1 | 7.5 | 75229 |

TABLE 10-continued

Binding to OVCAR3 Cells

| Antibody | EC$_{50}$ (nM) | Top (MFI) |
| --- | --- | --- |
| xi90G10H7 hIgG1 | 3.9 | 72926 |
| 90G10H7.p1 hIgG1 | 2.5 | 73591 |
| 90G10H7.p4 hIgG1 | 2.2 | 71848 |
| xi55E5B6D12 hIgG1 | 5.1 | 71368 |
| 55E5B6D12.p2 hIgG1 | 28 | 67983 |
| xi91C9F1 hIgG1 | 1.6 | 63258 |
| 91C9F1.p1 hIgG1 | 1 | 63499 |

Figure 11:
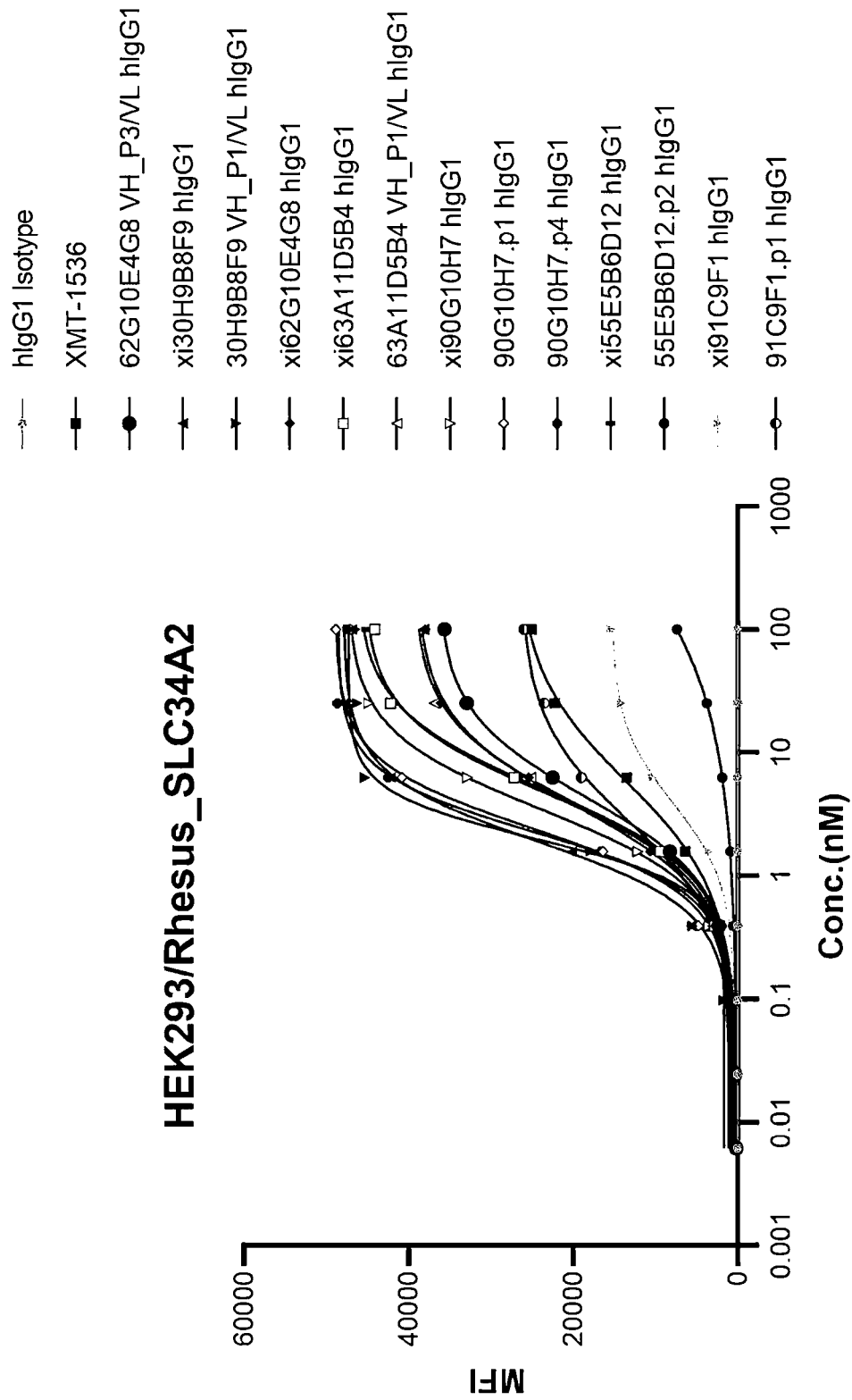
FIG. 11 shows the binding activity of the PTM-derisked antibodies to Rhesus SLC34A2 expressed on HEC293 cells.
Figure 12A:
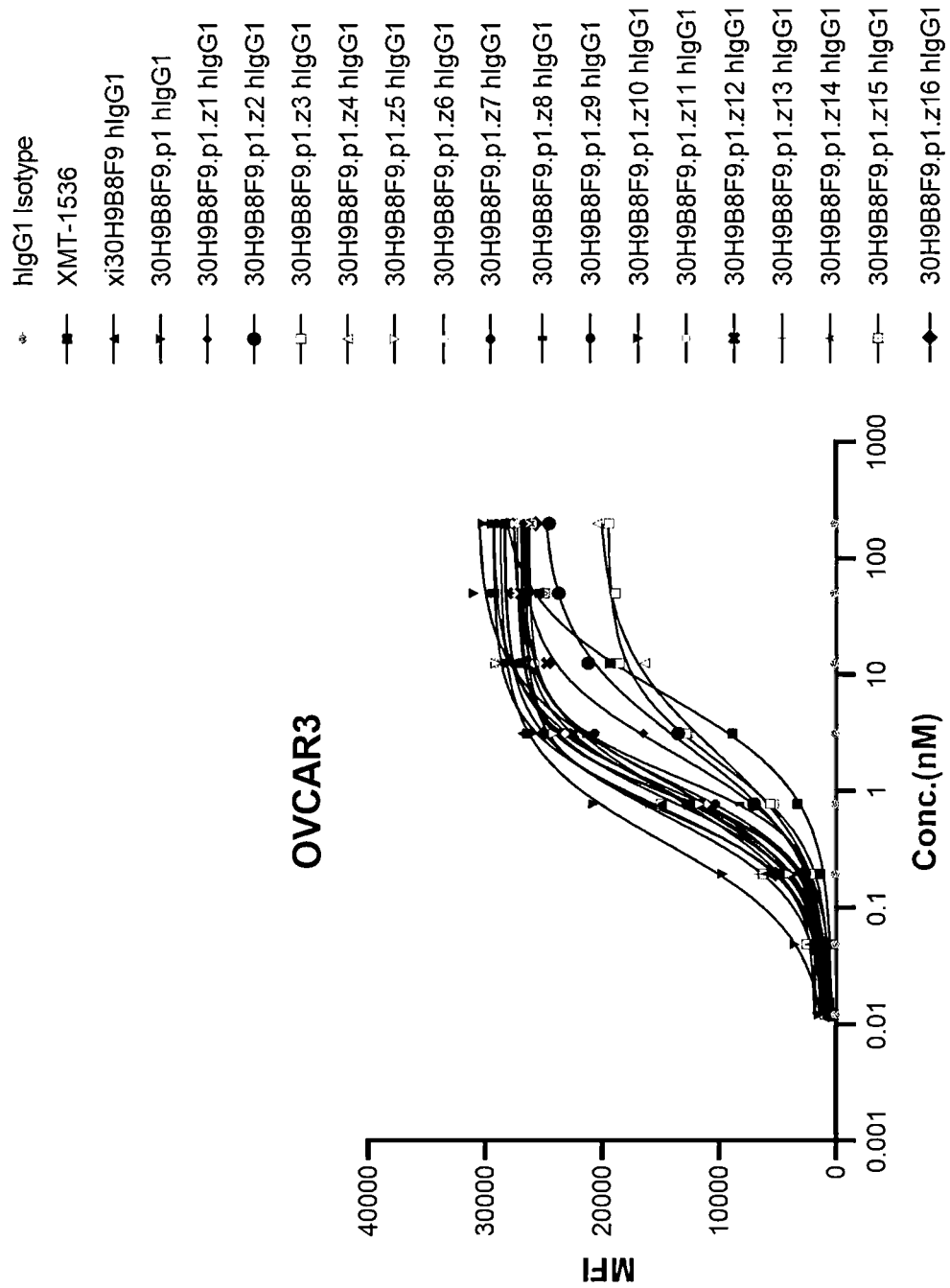
FIG. 12A-D show the binding activity of the humanized antibodies to endogenously expressed SLC34A2 on OVCAR3 cells.
Figure 12B:
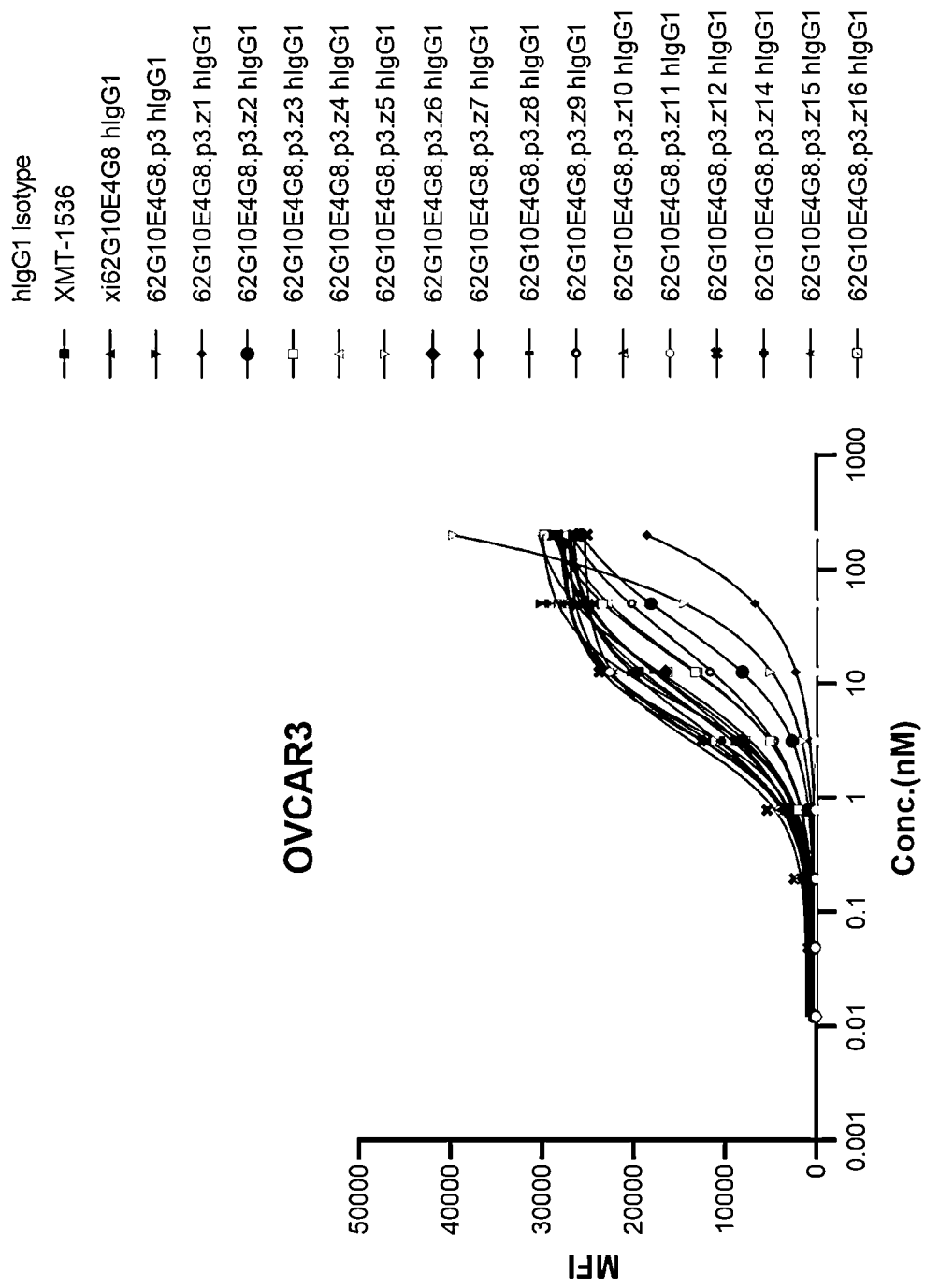
Figure 12C:
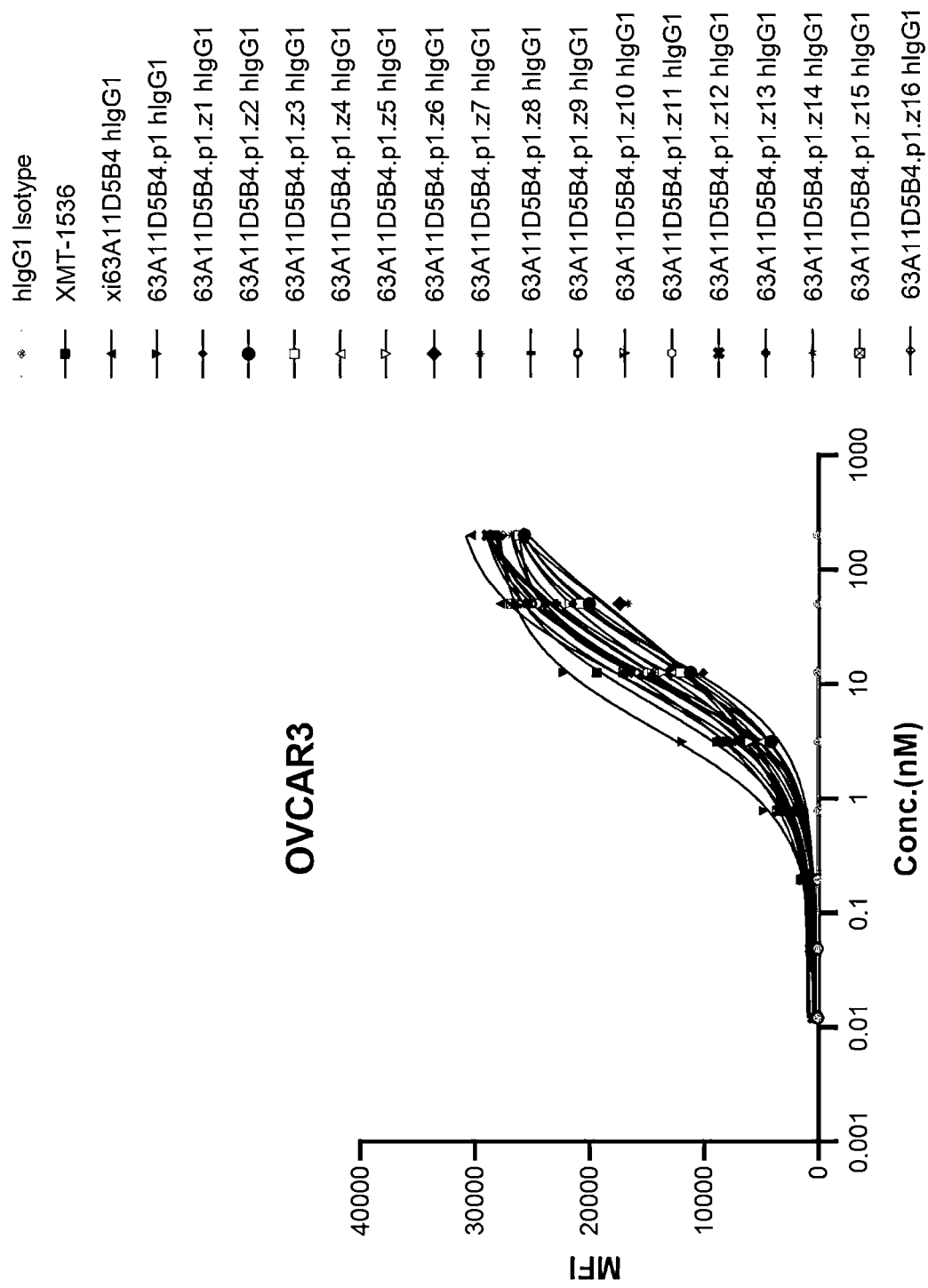
Figure 12D:
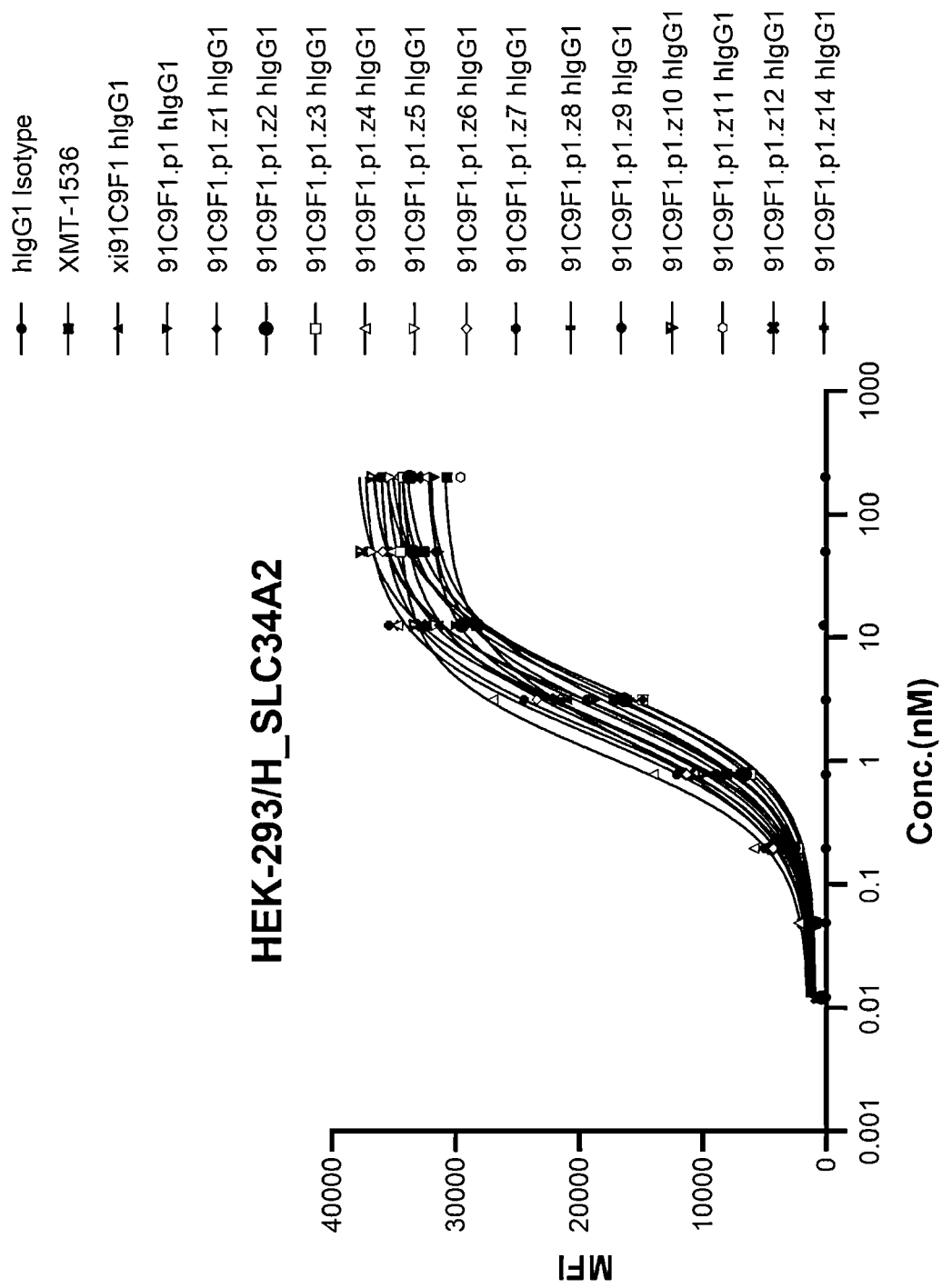
Figure 13A:
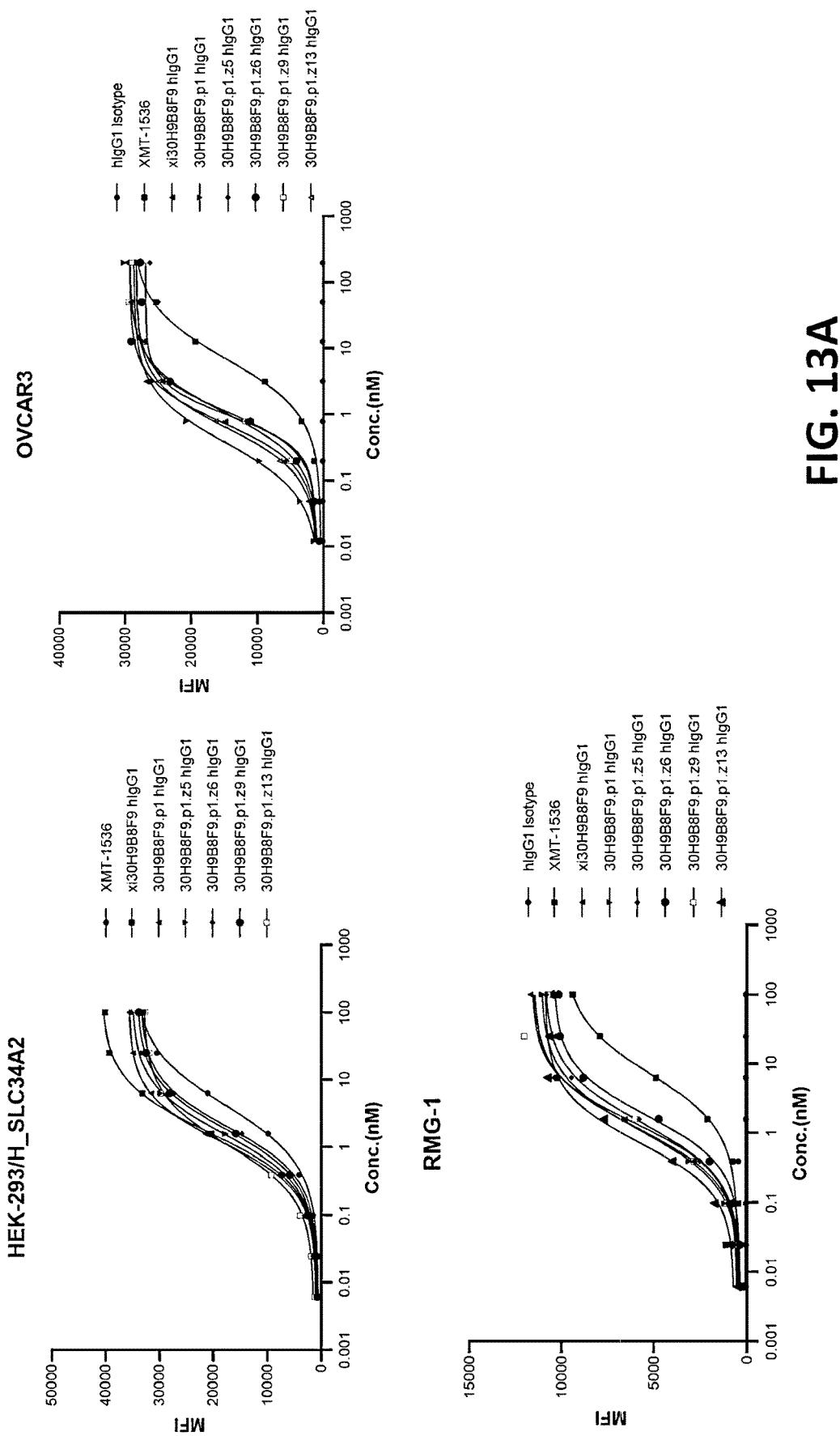
FIG. 13A-D show the binding activity of the humanized antibodies to human SLC34A2 on different types of cells.
Figure 13B:
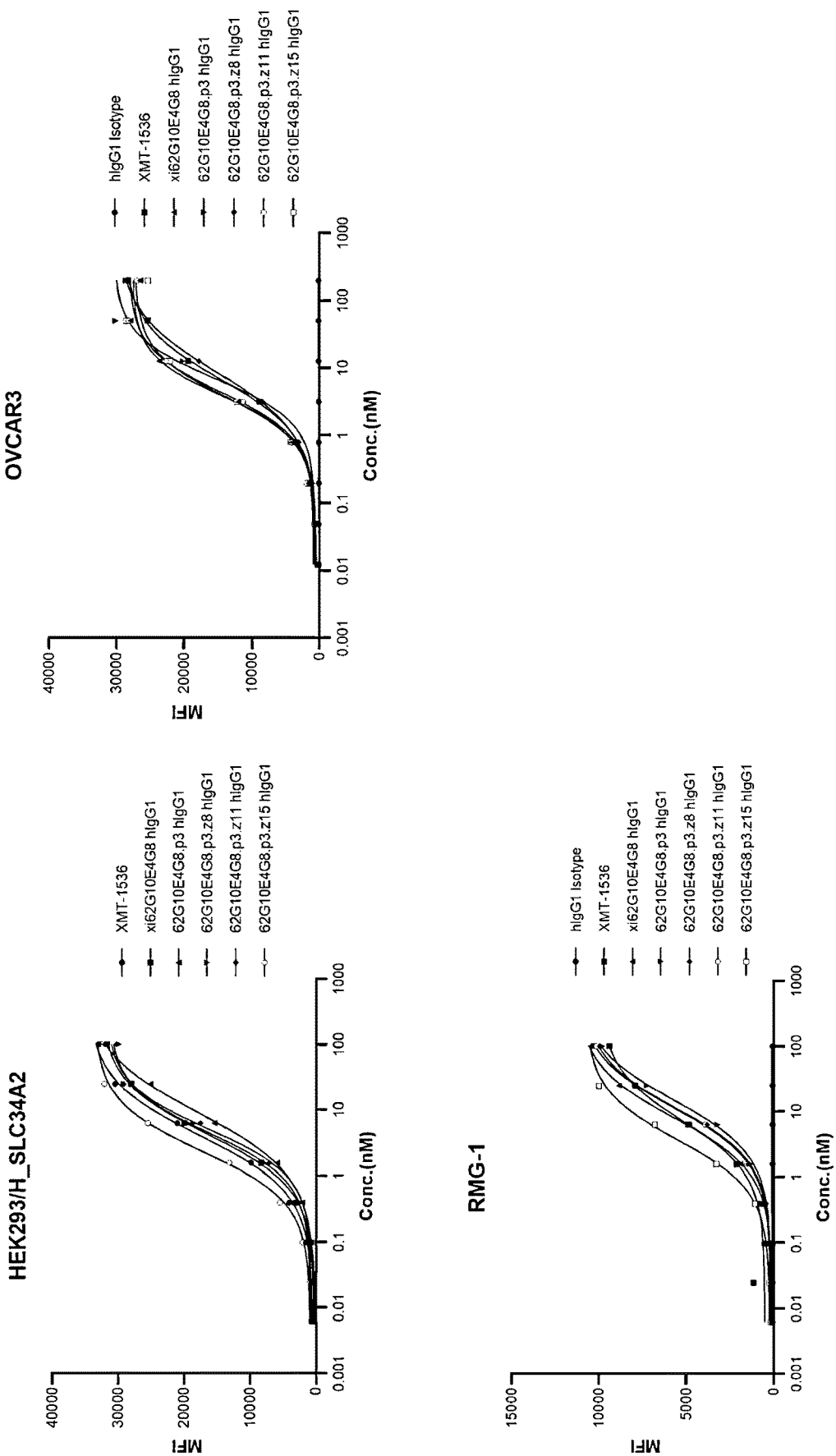
Figure 13C:
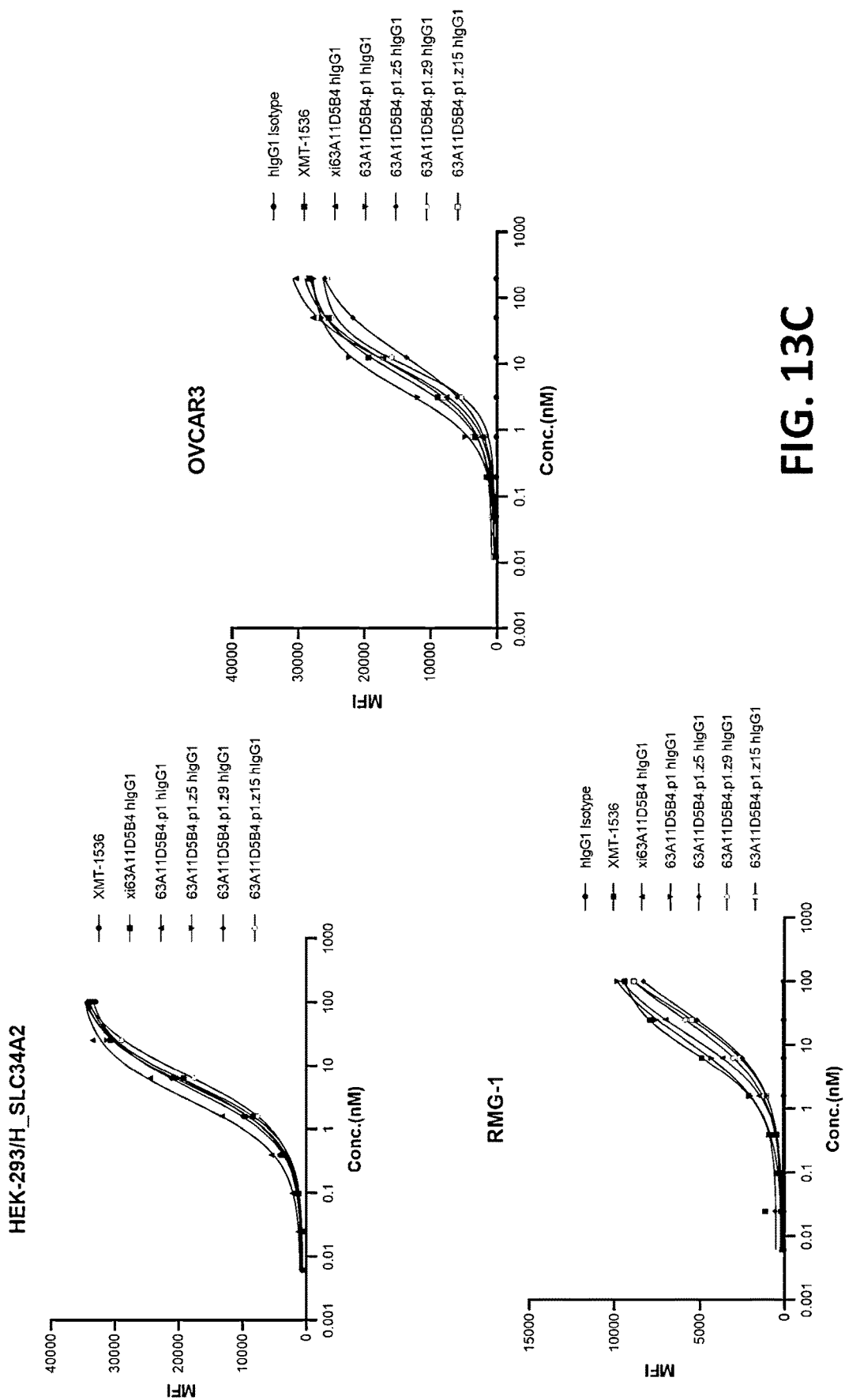
Figure 13D:
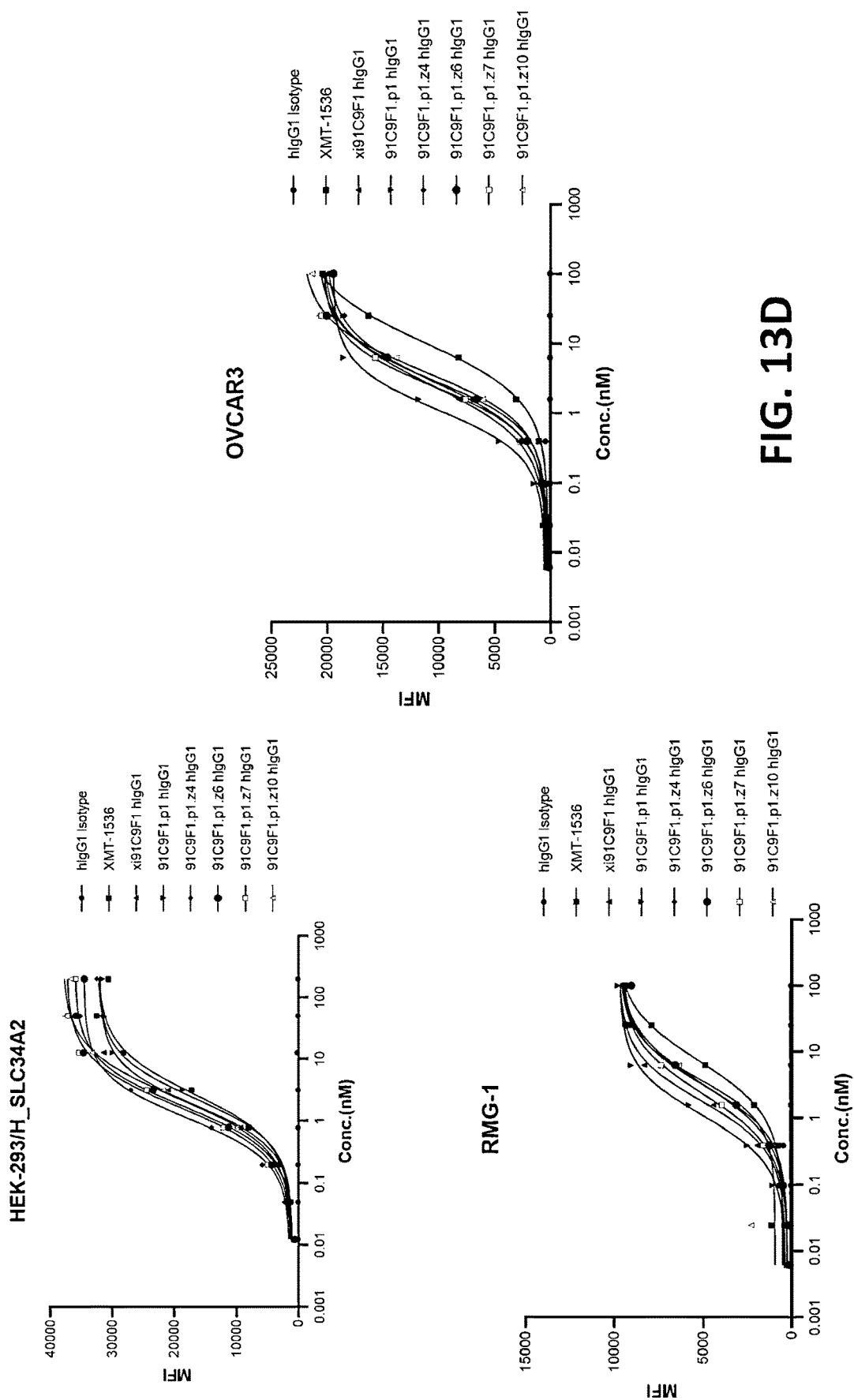

These antibodies' binding to Rhesus SLC34A2 was also tested using a procedure as described above. The results are shown in FIG. 11 and Table 11, confirming the high affinity of these PTM-derisked sequences.

TABLE 11

Binding to Rhesus SLC34A2

| Antibody | EC$_{50}$ (nM) | Top (MFI) |
| --- | --- | --- |
| hIgG1 Isotype | NA | NA |
| XMT-1536 | 5.8 | 27020 |
| xi30H9B8F9 hIgG1 | 1.9 | 47919 |
| 30H9B8F9 VH_P1/VL hIgG1 | 2 | 47355 |
| xi62G10E4G8 hIgG1 | 3.7 | 39085 |
| 62G10E4G8 VH_P3/VL hIgG1 | 4.3 | 36475 |
| xi63A11D5B4 hIgG1 | 4.6 | 45513 |
| 63A11D5B4 VH_P1/VL hIgG1 | 3.9 | 39411 |
| xi90G10H7 hIgG1 | 3.5 | 47439 |
| 90G10H7.p1 hIgG1 | 2.4 | 48938 |
| 90G10H7.p4 hIgG1 | 2.3 | 48591 |
| xi55E5B6D12 hIgG1 | 4.9 | 46426 |
| 55E5B6D12.p2 hIgG1 | ~21808 | ~121986 |
| xi91C9F1 hIgG1 | 3.9 | 15455 |
| 91C9F1.p1 hIgG1 | 2.8 | 26430 |

Example 8. Humanized Antibodies

Based on the above results, four of the above antibodies, 30H9B8F9, 62G10E4G8, 63A11D5B4, and 91C9F1, continued to be developed through humanization.

The amino acid sequences of the VH and VL of each murine antibody were compared against the available database of human Ig gene sequences to find the overall best-matching human germline Ig gene sequences. The CDRs of the murine antibodies were then grafted into the matched human sequences. The cDNA was synthesized and used to produce the humanized antibodies. Certain back mutations from the murine antibodies were then introduced back to the humanized antibodies.

The amino acid sequences of the humanized antibodies are provided in Tables 12-15 below.

Humanized and PTM-Derisked Sequences
A. 30-H9(B8)F9

TABLE 12A

| | Humanized Sequences | |
|---|---|---|
| Antibody chain | Sequence (bold residues are back mutations; PTM-derisked ones are boxed) | SEQ ID NO: |
| 30-H9(B8)F9 VH | QVQLQQPGAELVKPGASVKMSCKTSGYTFTTNNMHWVKQTPGQGLEWIGAI YPGNGATAYNQKFKGKATLTADKSSSTAYMQLSSLTSEASAVYYCARGMYG HGAMDYWGQGTSVIVSS | 1 |
| 30-H9(B8)F9.p1 VH_1 | QVQLVQSGAEVKKPGASVKVSCKASGYTFTTNNMHWVRQAPGQGLEWMGAI YPG[SG]ATAYNQKFKGRVTMTRDTSTSTVYMELSSLRSEDTAVYYCASGMYG HGAMDYWGQGTLVTVSS | 58 |
| 30-H9(B8)F9.p1 VH_2 | QVQLVQSGAEVKKPGASVKVSCTSGYTFTTNNMHWVRQAPGQGLEWIGAI YPG[SG]ATAYNQKFKGRVTMADTSTSTVYMELSSLRSEDTAVYYCARGMYG HGAMDYWGQGTLVTVSS | 59 |
| 30-H9(B8)F9.p1 VH_3 | QVQLVQSGAEVVKPGASVKVSCTSGYTFTTNNMHWVRQAPGQGLEWIGAI YPG[SG]ATAYNQKFKGRVTLTADKSTSTAYMELSSLRSEATAVYYCARGMYG HGAMDYWGQGTLVTVSS | 60 |
| 30-H9(B8)F9.p1 VH_4 | QVQLVQSGAEVVKPGASVKMSCTSGYTFTTNNMHWVKQAPGQGLEWIGAI YPG[SG]ATAYNQKFKGRATLTADKSTSTAYMELSSLRSEATAVYYCARGMYG HGAMDYWGQGTSVTVSS | 61 |
| 30-H9(B8)F9 VL | DIVMTQSHKFMSRSVGDRVRITCKASQDVGTAVAWYQQKPGQSPKLLIYWA TTRHSGVPDRFTGSGSGTDFIFTISNVQSEDLADYFCQQYSSNPLTFGAGT KLELK | 2 |
| 30-H9(B8)F9 VL_1 | DIQLTQSPSFLSASVGDRVTITCKASQDVGTAVAWYQQKPGKAPKLLIYWA TTRHSGVPSRFSGSGSGTEFTLTISSLQPEDFATYYCQQYSSNPLTFGQGT KLEIK | 62 |
| 30-H9(B8)F9 VL_2 | DIQLTQSPSFLSASVGDRVTITCKASQDVGTAVAWYQQKPGKSPKLLIYWA TTRHSGVPDRFSGSGSGTEFTFTISSLQPEDFATYFCQQYSSNPLTFGQGT KLEIK | 63 |
| 30-H9(B8)F9 VL_3 | DIQMTQSPSFLSASVGDRVTITCKASQDVGTAVAWYQQKPGKSPKLLIYWA TTRHSGVPDRFSGSGSGTEFIFTISSVQPEDFATYFCQQYSSNPLTFGAGT KLEIK | 64 |
| 30-H9(B8)F9 VL_4 | DIVMTQSPSFLSASVGDRVTITCKASQDVGTAVAWYQQKPGKSPKLLIYWA TTRHSGVPDRFTGSGSGTDFIFTISSVQPEDFATYFCQQYSSNPLTFGAGT KLEIK | 65 |

TABLE 12B

| CDR Sequences | | |
|---|---|---|
| Region | Sequence | SEQ ID NO: |
| VH CDR1 | TNNMH | 51 |
| VH CDR2 | AIYPGNGATAYNQKFKG | 57 |
| | AIYPG[SG]ATAYNQKFKG | 52 |
| VH CDR3 | GMYGHGAMDY | 53 |
| VL CDR1 | KASQDVGTAVA | 54 |
| VL CDR2 | WATTRHS | 55 |
| VL CDR3 | QQYSSNPLT | 56 |

TABLE 12C

| Humanized Antibodies | | | | |
|---|---|---|---|---|
| 30-H9(B8)F9.p1 | VH_1 | VH_2 | VH_3 | VH_4 |
| VL_1 | Z1 | Z5 | Z9 | Z13 |
| VL_2 | Z2 | Z6 | Z10 | Z14 |
| VL_3 | Z3 | Z7 | Z11 | Z15 |
| VL_4 | Z4 | Z8 | Z12 | Z16 |

B. 62-G10(E4)G8

TABLE 13A

| | Humanized Sequences | |
|---|---|---|
| Antibody chain | Sequence (bold residues are back mutations; PTM-derisked ones are boxed) | SEQ ID NO: |
| 62-G10(E4)G8 VH | QVQLQQSGAEVVKPGASVKMSCKASGYTFPSYITHWVKQTPGQGLEWIGA IYPGNGDTSYIQKFKGKATLTADKSSSTAYMQLSSLTSEDSAVYYCARGT YGTSAWFTYWGQGTLVTVSA | 3 |

TABLE 13A-continued

Humanized Sequences

| Antibody chain | Sequence (bold residues are back mutations; PTM-derisked ones are boxed) | SEQ ID NO: |
|---|---|---|
| 62-G10(E4)G8.p3 VH_1 | QVQLVQSGAEVKKPGASVKVSCKASGYTFPSYITHWVRQAPGQGLEWMGA IYPGNADTSYIQKFKGRVTMTRDTSTSTVYMELSSLRSEDTAVYYCARGT YGTSAWFTYWGQGTLVTVSS | 73 |
| 62-G10(E4)G8.p3 VH_2 | QVQLVQSGAEVKKPGASVKVSCKASGYTFPSYITHWVRQAPGQGLEIMGA IYPGNADTSYIQKFKGRVTMTADKSTSTVYMELSSLRSEDTAVYYCARGT YGTSAWFTYWGQGTLVTVSS | 74 |
| 62-G10(E4)G8.p3 VH_3 | QVQLVQSGAEVKKPGASVKVSCKASGYTFPSYITHWVKQAPGQGLEWIGA IYPGNADTSYIQKFKGRVTLADKSTSTAYMELSSLRSEDTAVYYCARGT YGTSAWFTYWGQGTLVTVSS | 75 |
| 62-G10(E4)G8.p3 VH_4 | QVQLVQSGAEVVKPGASVKMSCKASGYTFPSYITHWVKQAPGQGLEIMGA IYPGNADTSYIQKFKGRATLTADKSTSTAYMELSSLRSEDTAVYYCARGT YGTSAWFTYWGQGTLVTVSS | 76 |
| 62-G10(E4)G8 VL | DIVLTQSPATLSVTPGDSVSLSCRARQNIGNNLYWYQQKSHESPRLLIKY ASQSISGIPSRFSGSGSGTDFTLTINSVETEDFGVYFCQQSFSWPLTFGA GTKLELK | 4 |
| 62-G10(E4)G8 VL_1 | EIVMTQSPATLSVSPGERATLSCRARQNIGNNLYWYQQKPGQAPRLLIYY ASQSISGIPARFSGSGSGTEFTLTISSLQSEDFAVYYCQQSFSWPLTFGQ GTKLEIK | 77 |
| 62-G10(E4)G8 VL_2 | EIVMTQSPATLSVSPGERATLSCRARQNIGNNLYWYQQKPGQSPRLLIKY ASQSISGIPARFSGSGSGTEFTLTISSLQSEDFAVYFCQQSFSWPLTFGQ GTKLEIK | 78 |
| 62-G10(E4)G8 VL_3 | EIVLTQSPATLSVSPGERATLSCRARQNIGNNLYWYQQKPGQSPRLLIKY ASQSISGIPSRFSGSGSGTDFTLTISSLQSEDFAVYFCQQSFSWPLTFGQ GTKLEIK | 79 |
| 62-G10(E4)G8 VL_4 | EIVLTQSPATLSASPGERATLSCRARQNIGNNLYWYQQKPGQSPRLLIKY ASQSISGIPSRFSGSGSGTDFTLTISSVQSEDFAVYFCQQSFSWPLTFGA GTKLEIK | 80 |

TABLE 13B

CDR Sequences

| Region | Sequence | SEQ ID NO: |
|---|---|---|
| VH CDR1 | SYITH | 66 |
| VH CDR2 | AIYPGNGDTSYIQKFKG | 72 |
|  | AIYPGNADTSYIQKFKG | 67 |
| VH CDR3 | GTYGTSAWFTY | 68 |
| VL CDR1 | RARQNIGNNLY | 69 |
| VL CDR2 | YASQSIS | 70 |
| VL CDR3 | QQSFSWPLT | 71 |

TABLE 13C

Humanized Antibodies

| 62-G10(E4)G8.p3 | VH_1 | VH_2 | VH_3 | VH_4 |
|---|---|---|---|---|
| VL_1 | Z1 | Z5 | Z9 | Z13 |
| VL_2 | Z2 | Z6 | Z10 | Z14 |
| VL_3 | Z3 | Z7 | Z11 | Z15 |
| VL_4 | Z4 | Z8 | Z12 | Z16 |

C. 63-A11(D5)B4

TABLE 14A

Humanized Sequences

| Antibody chain | Sequence (bold residues are back mutations; PTM-derisked ones are boxed) | SEQ ID NO: |
|---|---|---|
| 63-A11(D5)B4 VH | QVQLQQPGAELVKPGASVKMSCRTSGYTFITYNMHWVKQTPGQGREWIGA IYPGNGDTSYNQKFKGKATLTADKSSSTAYMOLNSLTSEDSAVYYCSIST IITTGAVDYWGQGTSVTAS | 5 |
| 63-A11(D5)B4.p1 VH_1 | QVQLVQSGAEVKKPGASVKVSCKASGYTFITYNMHWVRQAPGQGLEWMGA IYPGSGDTSYNQKFKGRVTMTRDTSTSTVYMELSSLRSEDTAVYYCASST IITTGAVDYWGQGTLVTVSS | 88 |
| 63-A11(D5)B4.p1 VH_2 | QVQLVQSGAEVKKPGASVKVSCKTSGYTFITYNMHWVRQAPGQGLEWIGA IYPGSGDTSYNQKFKGRVTMTADTSTSTVYMELSSLRSEDTAVYYCSIST IITTGAVDYWGQGTLVTVSS | 89 |

TABLE 14A-continued

Humanized Sequences

| Antibody chain | Sequence (bold residues are back mutations; PTM-derisked ones are boxed) | SEQ ID NO: |
|---|---|---|
| 63-A11(D5)B4.p1 VH_3 | QVQLVQSGAEVVKPGASVKMSCKTSGYTFITYNMHWVRQAPGQGLEWIGA IYPG[SG]DTSYNQKFKGRVTLTADKSTSTAYMELSRSEDTAVYYCSIST IITTGAVDYWGQGTLVTVSS | 90 |
| 63-A11(D5)B4.p1 VH_4 | QVQLQQSGAEVVKPGASVKMSCKTSGYTFITYNMHWVKQAPGQGREWIGA IYPG[SG]DTSYNQKFKGRATLTADKSTSTAYMELSRSEDTAVYYCSIST IITTGAVDYWGQGTSVTVSS | 91 |
| 63-A11(D5)B4 VL | DIVMTQSHKFMSTSVGDRVSITCKASQDVGTAVAWYQQKAGQSPKLLIYW TSTRHTGVPDRFTGSGSGTDFTLI IRSLQSEDLADYFCQQYSRIPLTFGS GTKLEIK | 6 |
| 63-A11(D5)B4 VL_1 | DIQMTQSPSSLSASVGDRVTITCKASQDVGTAVAWYQQKPGKVPKLLIYW TSTRHTGVPSRFSGSGSGTDFTLTISSLOPEDVATYYCQQYSRIPLTFGG GTKVEIK | 92 |
| 63-A11(D5)B4 VL_2 | DIQMTQSPSSLSTSVGDRVTITCKASQDVGTAVAWYQQKPGKSPKLLIYW TSTRHTGVPSRFSGSGSGTDFTLIISSLOPEDVATYYCQQYSRIPLTFGG GTKVEIK | 93 |
| 63-A11(D5)B4 VL_3 | DIQMTQSPSSLSTSVGDRVTITCKASQDVGTAVAWYQQKPGQSPKLLIYW TSTRHTGVPDRFSGSGSGTDFTLIIRSLQPEDVATYFCQQYSRIPLTFGG GTKVEIK | 94 |
| 63-A11(D5)B4 VL_4 | DIVMTQSPSSLSTSVGDRVTITCKASQDVGTAVAWYQQKPGQSPKLLIYW TSTRHTGVPDRFTGSGSGTDFTLIIRSLQPEDVATYFCQQYSRIPLTFGS GTKVEIK | 95 |

TABLE 14B

CDR Sequences

| Region | Sequence | SEQ ID NO: |
|---|---|---|
| VH CDR1 | TYNMH | 81 |
| VH CDR2 | AIYPGNGDTSYNQKFKG | 87 |
| | AIYPG[SG]DTSYNQKFKG | 82 |
| VH CDR3 | STIITTGAVDY | 83 |
| VL CDR1 | KASQDVGTAVA | 84 |
| VL CDR2 | WTSTRHT | 85 |
| VL CDR3 | QQYSRIPLT | 86 |

TABLE 14C

Humanized Antibodies

| 63-A11(D5)B4.p1 | VH_1 | VH_2 | VH_3 | VH_4 |
|---|---|---|---|---|
| VL_1 | Z1 | Z5 | Z9 | Z13 |
| VL_2 | Z2 | Z6 | Z10 | Z14 |
| VL_3 | Z3 | Z7 | Z11 | Z15 |
| VL_4 | Z4 | Z8 | Z12 | Z16 |

D. 91-C9F1

TABLE 15A

Humanized Sequences

| Antibody chain | Sequence (bold residues are back mutations; PTM-derisked ones are boxed) | SEQ ID NO: |
|---|---|---|
| 91-C9F1 VH | EVQLQQSGPELVKPGTSVKISCKTSGFFFTEYIIHWVKQSHGRSLEWIGG IIPNNGVTNYKQNFRGKAALTADKSSNTAYMELRSLTSEDSAVYYCARWR NGYYSAMDSWGQGTSVTVSS | 7 |
| 91-C9F1.p1 VH_1 | QVQLVQSGAEVKKPGSSVKVSCKASGFFFTEYIIHWVRQAPGQGLEWMGG IIPN[ND]VTNYKQNFRGRVTITADESTSTAYMELSSLRSEDTAVYYCARWR [NA]YYSAMDSWGQGTTVTVSS | 104 |
| 91-C9F1.p1 VH_2 | QVQLVQSGAEVKKPGSSVKVSCKTSGFFFTEYIIHWVRQAPGQGLEWIGG IIPN[ND]VTNYKQNFRGRVTLTADKSTSTAYMELSSLRSEDTAVYYCARWR [NA]YYSAMDSWGQGTTVTVSS | 105 |
| 91-C9F1.p1 VH_3 | QVQLVQSGAEVVKPGSSVKVSCKTSGFFFTEYIIHWVRQSPGQGLEWIGG IIPN[ND]VTNYKQNFRGRATLTADKSTSTAYMELSSLRSEDTAVYYCARWR [NA]YYSAMDSWGQGTTVTVSS | 106 |

TABLE 15A-continued

Humanized Sequences

| Antibody chain | Sequence (bold residues are back mutations; PTM-derisked ones are boxed) | SEQ ID NO: |
|---|---|---|
| 91-C9F1.p1 VH_4 | QVQLVQSGAEVVKPGSSVKISCKTSGFFFTEYIIHWVKQSPGQGLEWIGG IIPN[ND]VTNYKQNFRGRATLTADKSTNTAYMELRSSLRSEDTAVYYCARW R[NA]YYSAMDSWGQGTTVTVSS | 107 |
| 91-C9F1 VL | DIVVTQSHKFMSTSLGDRVSITCTASQDVGTAVAWYQQKPGHSPKLLIYW ASTRHTGVPERPTGSGSGTDFTLTITNVQSEDLADYFCQQYRTSPLTFGV GTKLELK | 8 |
| 91-C9F1 VL_1 | DIQMTQSPSSLSASVGDRVTITCTASQDVGTAVAWYQQKPGKVPKLLIYW ASTRHTGVPSRFSGSGSGTDFTLTISSLOPEDVATYYCQQYRTSPLTFGG GTKVEIK | 108 |
| 91-C9F1 VL_2 | DIQMTQSPSSLSTSVGDRVTITCTASQDVGTAVAWYQQKPGKSPKLLIYW ASTRHTGVPERFSGSGSGTDFTLTISSLOPEDVATYFCQQYRTSPLTFGG GTKVEIK | 109 |
| 91-C9F1 VL_3 | DIQVTQSPSSLSTSVGDRVTITCTASQDVGTAVAWYQQKPGKSPKLLIYW ASTRHTGVPERFTGSGSGTDFTLTISSVQPEDVATYFCQQYRTSPLTFGV GTKVEIK | 110 |
| 91-C9F1 VL_4 | DIVVTQSPSSLSTSVGDRVTITCTASQDVGTAVAWYQQKPGKSPKLLIYW ASTRHTGVPERFTGSGSGTDFTLTISSVQPEDVATYFCQQYRTSPLTFGV GTKLELK | 111 |

TABLE 15B

CDR Sequences

| Region | Sequence | SEQ ID NO: |
|---|---|---|
| VH CDR1 | EYIIH | 96 |
| VH CDR2 | GIIPNNGVTNYKQNFRG | 102 |
|  | GIIPN[ND]VTNYKQNFRG | 97 |
| VH CDR3 | WRNGYYSAMDS | 103 |
|  | WR[NA]YYSAMDS | 98 |
| VL CDR1 | TASQDVGTAVA | 99 |
| VL CDR2 | WASTRHT | 100 |
| VL CDR3 | QQYRTSPLT | 101 |

TABLE 15C

Humanized Antibodies

| 91-C9F1.p1 | VH_1 | VH_2 | VH_3 | VH_4 |
|---|---|---|---|---|
| VL_1 | Z1 | Z5 | Z9 | Z13 |
| VL_2 | Z2 | Z6 | Z10 | Z14 |
| VL_3 | Z3 | Z7 | Z11 | Z15 |
| VL_4 | Z4 | Z8 | Z12 | Z16 |

The binding of these humanized antibodies to OVCAR3 cells was evaluated as described above, and the results are shown in FIG. 12A-D and Tables 16A-D.

TABLE 16A

Binding of Humanized Antibody to OVCAR3 - 30H9B8F9

| Antibody | EC$_{50}$ (nM) | Top (MFI) |
|---|---|---|
| hIgG1 Isotype | NA | NA |
| XMT-1536 | 6.87 | 28971 |
| xi30H9B8F9 hIgG1 | 1.19 | 29312 |
| 30H9B8F9.p1 hIgG1 | 0.68 | 28737 |
| 30H9B8F9.p1.z1 hIgG1 | 2.75 | 27108 |
| 30H9B8F9.p1.z2 hIgG1 | 3.09 | 25230 |
| 30H9B8F9.p1.z3 hIgG1 | 2.38 | 19581 |
| 30H9B8F9.p1.z4 hIgG1 | 2.76 | 20368 |
| 30H9B8F9.p1.z5 hIgG1 | 1.43 | 26938 |
| 30H9B8F9.p1.z6 hIgG1 | 1.62 | 28382 |
| 30H9B8F9.p1.z7 hIgG1 | 1.69 | 26723 |
| 30H9B8F9.p1.z8 hIgG1 | 1.90 | 26229 |
| 30H9B8F9.p1.z9 hIgG1 | 1.59 | 29362 |
| 30H9B8F9.p1.z10 hIgG1 | 1.93 | 30701 |
| 30H9B8F9.p1.z11 hIgG1 | 1.43 | 26954 |
| 30H9B8F9.p1.z12 hIgG1 | 1.40 | 27646 |
| 30H9B8F9.p1.z13 hIgG1 | 1.03 | 28350 |
| 30H9B8F9.p1.z14 hIgG1 | 1.31 | 27280 |
| 30H9B8F9.p1.z15 hIgG1 | 1.05 | 26470 |
| 30H9B8F9.p1.z16 hIgG1 | 1.41 | 26538 |

TABLE 16B

Binding of Humanized Antibody to OVCAR3 - 62G10E4G8

| Antibody | EC$_{50}$ (nM) | Top (MFI) |
|---|---|---|
| hIgG1 Isotype | NA | NA |
| XMT-1536 | 6.82 | 28971 |
| xi62G10E4G8 hIgG1 | 3.73 | 27650 |
| 62G10E4G8.p3 hIgG1 | 6.98 | 30347 |
| 62G10E4G8.p3.z1 hIgG1 | 943.80 | 87738 |
| 62G10E4G8.p3.z2 hIgG1 | 32.88 | 29698 |
| 62G10E4G8.p3.z3 hIgG1 | 17.33 | 31289 |
| 62G10E4G8.p3.z4 hIgG1 | 16.27 | 29908 |
| 62G10E4G8.p3.z5 hIgG1 | ~1361 | ~230025 |
| 62G10E4G8.p3.z6 hIgG1 | 8.06 | 28157 |
| 62G10E4G8.p3.z7 hIgG1 | 6.08 | 26810 |
| 62G10E4G8.p3.z8 hIgG1 | 8.61 | 29963 |
| 62G10E4G8.p3.z9 hIgG1 | 24.07 | 31332 |
| 62G10E4G8.p3.z10 hIgG1 | 4.87 | 27396 |
| 62G10E4G8.p3.z11 hIgG1 | 4.32 | 28200 |
| 62G10E4G8.p3.z12 hIgG1 | 2.96 | 25440 |
| 62G10E4G8.p3.z14 hIgG1 | 4.58 | 27907 |
| 62G10E4G8.p3.z15 hIgG1 | 3.76 | 27300 |
| 62G10E4G8.p3.z16 hIgG1 | 10.95 | 31916 |

TABLE 16C

Binding of Humanized Antibody to OVCAR3 - 63A11D5B4

| Antibody | EC$_{50}$ (nM) | Top (MFI) |
|---|---|---|
| hIgG1 Isotype | NA | NA |
| XMT-1536 | 6.82 | 28971 |
| xi63A11D5B4 hIgG1 | 10.48 | 32147 |
| 63A11D5B4.p1 hIgG1 | 4.03 | 28244 |
| 63A11D5B4.p1.z1 hIgG1 | 19.58 | 28022 |
| 63A11D5B4.p1.z2 hIgG1 | 20.55 | 28738 |
| 63A11D5B4.p1.z3 hIgG1 | 17.90 | 28559 |
| 63A11D5B4.p1.z4 hIgG1 | 18.15 | 29017 |
| 63A11D5B4.p1.z5 hIgG1 | 13.46 | 28246 |
| 63A11D5B4.p1.z6 hIgG1 | 36.79 | 34614 |
| 63A11D5B4.p1.z7 hIgG1 | 61.13 | 40970 |
| 63A11D5B4.p1.z8 hIgG1 | 14.17 | 27880 |
| 63A11D5B4.p1.z9 hIgG1 | 9.12 | 26528 |
| 63A11D5B4.p1.z10 hIgG1 | 12.27 | 29808 |
| 63A11D5B4.p1.z11 hIgG1 | 10.26 | 27701 |
| 63A11D5B4.p1.z12 hIgG1 | 11.74 | 31674 |
| 63A11D5B4.p1.z13 hIgG1 | 16.42 | 32592 |
| 63A11D5B4.p1.z14 hIgG1 | 16.09 | 32605 |
| 63A11D5B4.p1.z15 hIgG1 | 9.23 | 30225 |
| 63A11D5B4.p1.z16 hIgG1 | 11.43 | 29478 |

TABLE 16D

Binding of Humanized Antibody to OVCAR3 - 91C9F1

| Antibody | EC$_{50}$ (nM) | Top (MFI) |
|---|---|---|
| hIgG1 Isotype | NA | NA |
| XMT-1536 | 2.68 | 32389 |
| xi91C9F1 hIgG1 | 1.77 | 32062 |
| 91C9F1.p1 hIgG1 | 2.29 | 32342 |
| 91C9F1.p1.z1 hIgG1 | 3.78 | 34220 |
| 91C9F1.p1.z2 hIgG1 | 3.32 | 34537 |
| 91C9F1.p1.z3 hIgG1 | 4.04 | 35456 |
| 91C9F1.p1.z4 hIgG1 | 1.12 | 34629 |
| 91C9F1.p1.z5 hIgG1 | 2.95 | 36861 |
| 91C9F1.p1.z6 hIgG1 | 1.72 | 36117 |
| 91C9F1.p1.z7 hIgG1 | 1.67 | 37440 |
| 91C9F1.p1.z8 hIgG1 | 2.13 | 35657 |
| 91C9F1.p1.z9 hIgG1 | 2.72 | 37027 |
| 91C9F1.p1.z10 hIgG1 | 2.32 | 38122 |
| 91C9F1.p1.z11 hIgG1 | 1.41 | 30997 |
| 91C9F1.p1.z12 hIgG1 | 1.77 | 34468 |
| 91C9F1.p1.z14 hIgG1 | 3.87 | 36194 |

In another testing, cell based binding of hu Abs on human SLC34A2 expressing cells were assessed using flow cytometry. Briefly, the HEK293/H_SLC34A2, OVCAR3 and RMG-1 cells were incubated with hu Abs. After incubation at 4° C. for 60 minutes, the cells were washed with FACS buffer twice, then stained with fluorescent conjugated secondary antibody at 4° C. for 30 minutes. After that the cells were washed twice and analyzed by flow cytometry.

The results of the study (FIG. 13A-D and Tables 17A-D) show that the hu Abs can bind to human SLC34A2 with high affinity.

TABLE 17A

Binding to Cell Lines - 30H9B8F9

| Clone list | HEK293/H_SLC34AA2 | | OVCAR3 | | RMG-1 | |
|---|---|---|---|---|---|---|
| | EC50 | Top | EC50 | Top | EC50 | Top |
| XMT-1536 | 4.05 | 34736 | 6.82 | 28971 | 7.17 | 9935 |
| xi30H9B8F9 hIgG1 | 1.63 | 40795 | 0.74 | 29312 | 1.19 | 11535 |
| 30H9B8F9.p1 hIgG1 | 1.18 | 35742 | 0.37 | 28737 | 1.09 | 11137 |
| 30H9B8F9.p1.z5 hIgG1 | 1.55 | 35156 | 0.94 | 26938 | 1.39 | 10920 |
| 30H9B8F9.p1.z6 hIgG1 | 1.94 | 33613 | 1.10 | 28382 | 1.78 | 10416 |
| 30H9B8F9.p1.z9 hIgG1 | 1.81 | 34196 | 1.08 | 29362 | 1.40 | 11618 |
| 30H9B8F9.p1.z13 hIgG1 | 1.05 | 33013 | 0.62 | 28350 | 0.73 | 10895 |

TABLE 17B

Binding to Cell Lines - 62G10E4G8

| Clone list | HEK293/H_SLC34AA2 | | OVCAR3 | | RMG-1 | |
|---|---|---|---|---|---|---|
| | EC50 | Top | EC50 | Top | EC50 | Top |
| XMT-1536 | 4.05 | 34736 | 6.82 | 28971 | 7.17 | 9935 |
| xi62G10E4G8 hIgG1 | 4.26 | 32706 | 3.73 | 27650 | 7.97 | 11293 |
| 62G10E4G8.p3 hIgG1 | 9.08 | 35676 | 6.98 | 30347 | 14.82 | 11229 |
| 62G10E4G8.p3.z8 hIgG1 | 4.42 | 31469 | 8.61 | 29963 | 11.05 | 10902 |
| 62G10E4G8.p3.z11 hIgG1 | 5.07 | 31855 | 4.32 | 28200 | 11.38 | 11254 |
| 62G10E4G8.p3.z15 hIgG1 | 2.34 | 33628 | 3.76 | 27300 | 3.69 | 10772 |

TABLE 17C

Binding to Cell Lines - 63A11D5B4

| Clone list | HEK293/H_SLC34AA2 EC50 | Top | OVCAR3 EC50 | Top | RMG-1 EC50 | Top |
|---|---|---|---|---|---|---|
| XMT-1536 | 4.05 | 34736 | 6.82 | 28971 | 7.17 | 9935 |
| xi63A11D5B4 hIgG1 | 5.21 | 35560 | 10.48 | 32147 | 14.40 | 11224 |
| 63A11D5B4.p1 hIgG1 | 2.79 | 35551 | 4.03 | 28244 | 12.51 | 11703 |
| 63A11D5B4.p1.z5 hIgG1 | 4.80 | 35866 | 13.46 | 28246 | 36.23 | 11839 |
| 63A11D5B4.p1.z9 hIgG1 | 5.49 | 36832 | 9.12 | 26528 | 28.28 | 12195 |
| 63A11D5B4.p1.z15 hIgG1 | 7.12 | 37020 | 9.23 | 30225 | 40.59 | 13248 |

TABLE 17D

Binding to Cell Lines - 91C9F1

| Clone list | HEK293/H_SLC34AA2 EC50 | Top | OVCAR3 EC50 | Top | RMG-1 EC50 | Top |
|---|---|---|---|---|---|---|
| XMT-1536 | 2.68 | 32389 | 10.32 | 22452 | 7.17 | 9935 |
| xi91C9F1 hIgG1 | 1.77 | 32062 | 2.50 | 20996 | 1.76 | 9733 |
| 91C9F1.p1 hIgG1 | 2.29 | 32342 | 1.10 | 19527 | 1.09 | 9692 |
| 91C9F1.p1.z4 hIgG1 | 1.12 | 34629 | 2.71 | 20185 | 3.22 | 9817 |
| 91C9F1.p1.z6 hIgG1 | 1.72 | 36117 | 2.86 | 20347 | 3.03 | 9560 |
| 91C9F1.p1.z7 hIgG1 | 1.67 | 37440 | 2.41 | 20461 | 2.25 | 9725 |
| 91C9F1.p1.z10 hIgG1 | 2.32 | 38122 | 3.96 | 22335 | 3.91 | 9592 |

Figure 14:
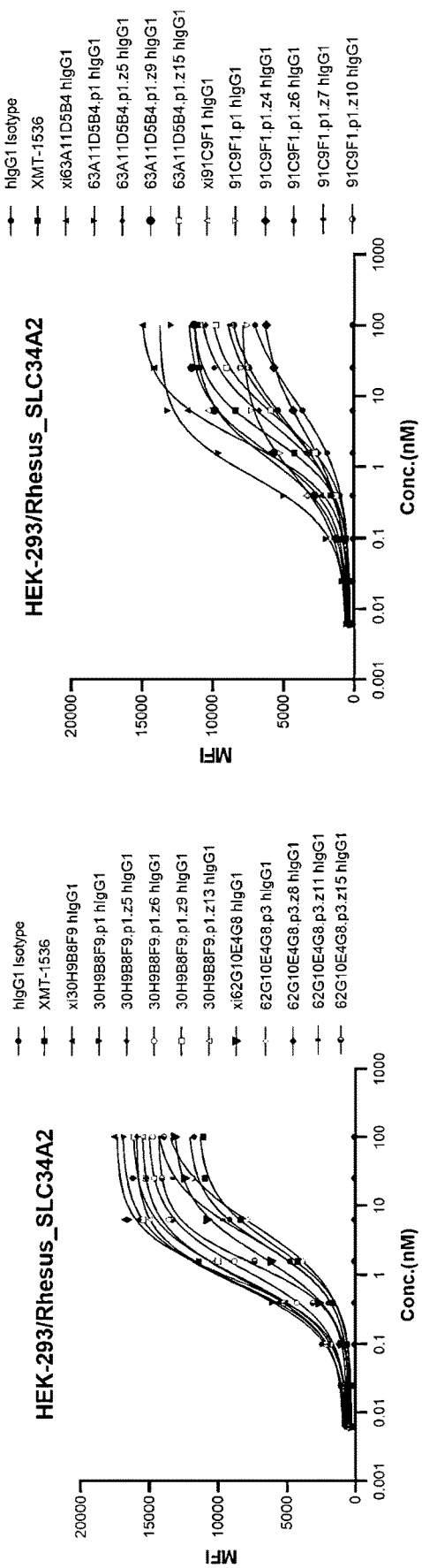
FIG. 14 shows the binding activity of the humanized antibodies to Rhesus SLC34A2 expressed on HEC293 cells.
Figure 15:
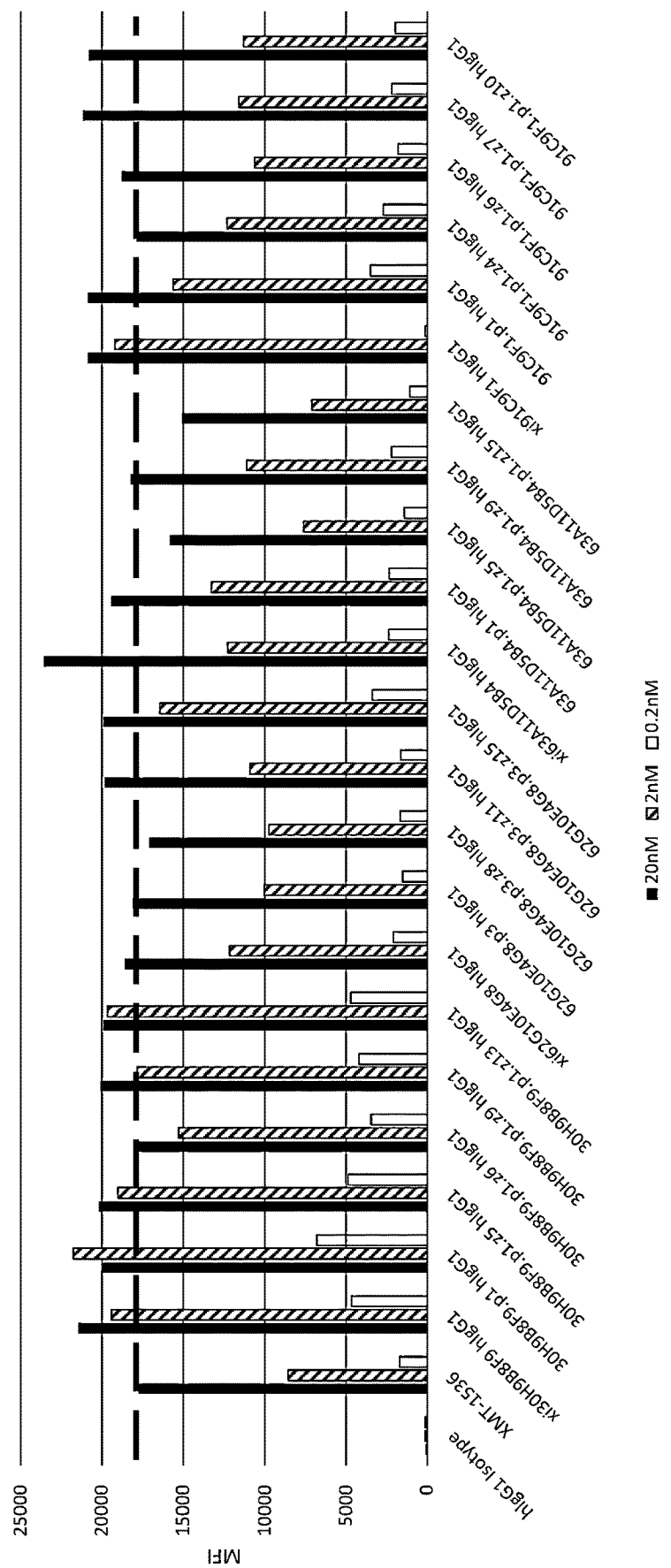
FIG. 15 shows the binding activity of the humanized antibodies to rat SLC34A2 expressed on HEC293 cells.
Figure 16:
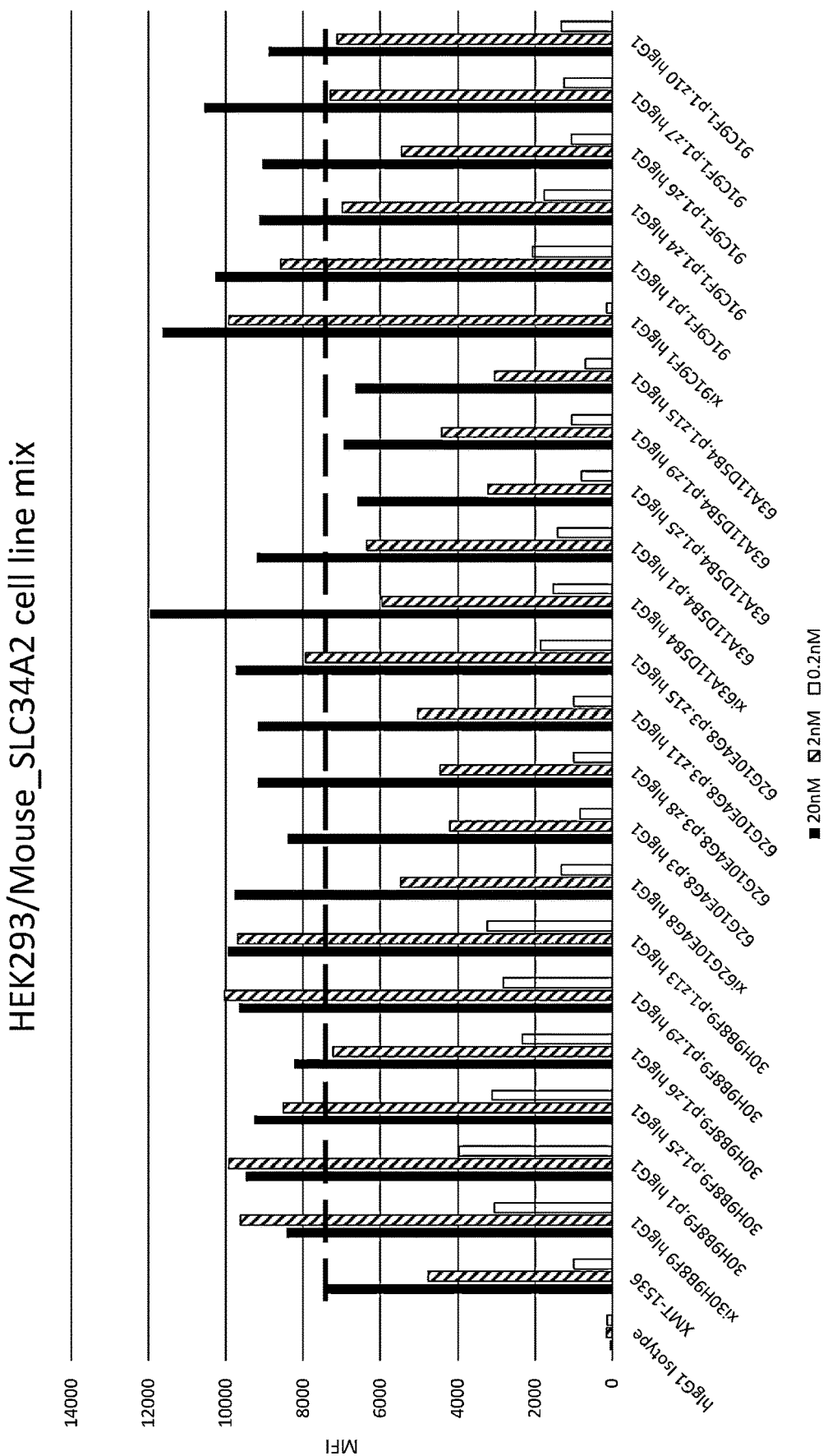
FIG. 16 shows the binding activity of the humanized antibodies to mouse SLC34A2 expressed on HEC293 cells.

In a further assay, these antibodies were evaluated for their binding affinity to Rhesus/rat/mouse SLC34A2, with the methods as described above. As shown in FIG. 14-16 and Table 18, these humanized antibodies retained the high affinity.

TABLE 18

Binding to Rhesus SLC34A2

| Antibody | $EC_{50}$ (nM) | Top (MFI) |
|---|---|---|
| hIgG1 Isotype | NA | NA |
| XMT-1536 | 2.6 | 11488 |
| xi30H9B8F9 hIgG1 | 0.9 | 17418 |
| 30H9B8F9.p1 hIgG1 | 0.8 | 17001 |
| 30H9B8F9.p1.z5 hIgG1 | 0.7 | 15993 |
| 30H9B8F9.p1.z6 hIgG1 | 1.1 | 15133 |
| 30H9B8F9.p1.z9 hIgG1 | 0.9 | 16265 |
| 30H9B8F9.p1.z13 hIgG1 | 0.8 | 15597 |
| xi62G10E4G8 hIgG1 | 1.8 | 13309 |
| 62G10E4G8.p3 hIgG1 | 5 | 14367 |
| 62G10E4G8.p3.z8 hIgG1 | 2.5 | 12206 |
| 62G10E4G8.p3.z11 hIgG1 | 3.4 | 14730 |
| 62G10E4G8.p3.z15 hIgG1 | 1.4 | 14363 |
| xi63A11D5B4 hIgG1 | 2.3 | 15157 |
| 63A11D5B4.p1 hIgG1 | 0.7 | 13775 |
| 63A11D5B4.p1.z5 hIgG1 | 3.9 | 11134 |
| 63A11D5B4.p1.z9 hIgG1 | 1.6 | 11777 |
| 63A11D5B4.p1.z15 hIgG1 | 4.7 | 10342 |
| xi91C9F1 hIgG1 | 1.2 | 11351 |
| 91C9F1.p1 hIgG1 | 0.8 | 7973 |
| 91C9F1.p1.z4 hIgG1 | 3.2 | 6719 |
| 91C9F1.p1.z6 hIgG1 | 8.8 | 8156 |
| 91C9F1.p1.z7 hIgG1 | 4.2 | 9495 |
| 91C9F1.p1.z10 hIgG1 | 4.2 | 9233 |

Example 8. ADCC of the Humanized Antibodies

This example measured the antibody-dependent cellular cytotoxicity (ADCC) of the humanized antibodies.

The ADCC Reporter Bioassay uses an alternative readout at an earlier point in ADCC MOA pathway activation: the activation of gene transcription through the NFAT (nuclear factor of activated T-cells) pathway in the effector cell. In addition, the ADCC Reporter Bioassay uses engineered Jurkat cells stably expressing the FcγRIIIa receptor, V158 (high affinity) variant, and an NFAT response element driving expression of firefly luciferase as effector cells. Antibody biological activity in ADCC MOA is quantified through the luciferase produced as a result of NFAT pathway activation; luciferase activity in the effector cell is quantified with luminescence readout. Signal is high, and assay background is low.

Serial dilutions of hu Abs were incubated for 6 hours of induction at 37° C. with engineered Jurkat effector cells (ADCC Bioassay Effector Cells), with ADCC Bioassay target Cells (expressing SLC34A2). Luciferase activity was quantified using ONE-Glo™ Luciferase Assay Buffer Reagent.

Figure 17:
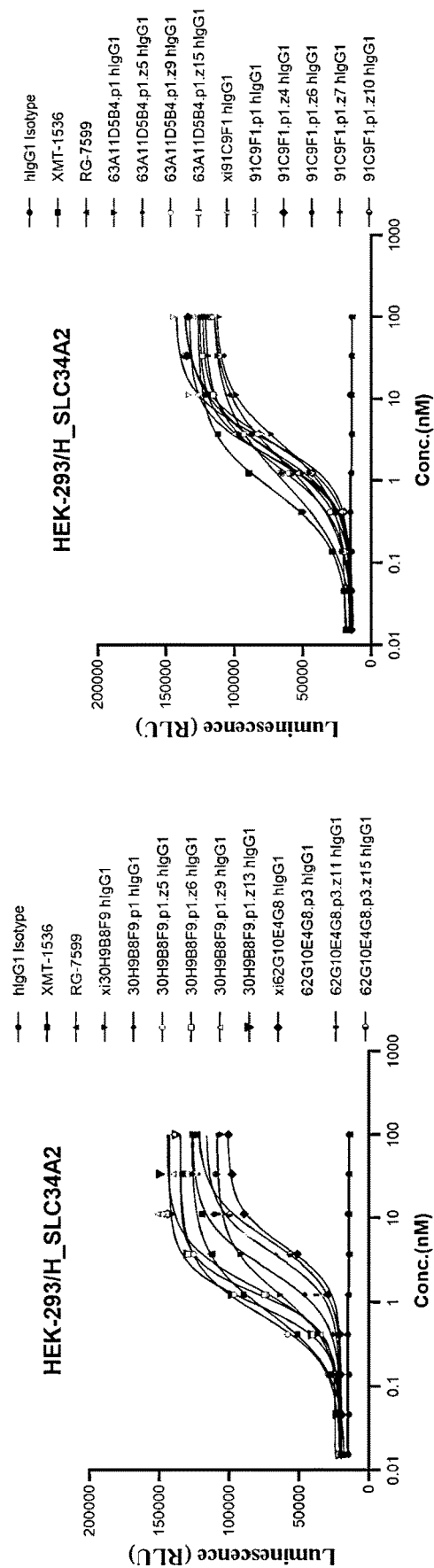
FIG. 17 shows the ADCC activity of the humanized antibodies against HEC293 cells expressing human SLC34A2.

The results are shown in FIG. 17 and Table 19, confirming the potent ADCC induction activity of these humanized antibodies.

TABLE 19

ADCC Activity

| Antibody | $EC_{50}$ (nM) | Top (MFI) |
|---|---|---|
| hIgG1 Isotype | ~33.32 | 14765 |
| XMT-1536 | 0.76 | 126843 |
| RG-7599 | ~1.310 | 15689 |
| xi30H9B8F9 hIgG1 | 1.26 | 108750 |
| 30H9B8F9.p1 hIgG1 | 2.52 | 126415 |
| 30H9B8F9.p1.z5 hIgG1 | 0.72 | 135100 |
| 30H9B8F9.p1.z6 hIgG1 | 1.25 | 134931 |
| 30H9B8F9.p1.z9 hIgG1 | 1.53 | 144513 |
| 30H9B8F9.p1.z13 hIgG1 | 0.96 | 142916 |
| xi62G10E4G8 hIgG1 | 4.56 | 100880 |
| 62G10E4G8.p3 hIgG1 | 4.23 | 122270 |
| 62G10E4G8.p3.z11 hIgG1 | 3.78 | 116421 |
| 62G10E4G8.p3.z15 hIgG1 | 5.39 | 122634 |
| 63A11D5B4.p1 hIgG1 | 2.83 | 113949 |
| 63A11D5B4.p1.z5 hIgG1 | 0.95 | 116223 |
| 63A11D5B4.p1.z9 hIgG1 | 1.69 | 116236 |
| 63A11D5B4.p1.z15 hIgG1 | 1.47 | 121606 |
| xi91C9F1 hIgG1 | 1.96 | 132927 |
| 91C9F1.p1 hIgG1 | 3.31 | 143117 |
| 91C9F1.p1.z4 hIgG1 | 3.14 | 137231 |
| 91C9F1.p1.z6 hIgG1 | 1.77 | 125245 |
| 91C9F1.p1.z7 hIgG1 | 2.12 | 123589 |
| 91C9F1.p1.z10 hIgG1 | 2.37 | 138028 |

Example 9. Testing of Selected Humanized Antibodies

Based on the previous results, four humanized antibodies were selected for further development, including 30-H9(B8) F9.p1.z5, 62-G10(E4)G8.p3.z15, 63-A11(D5)B4.p1.z9, and 91-C9F1.p1.z7.

Figure 18:
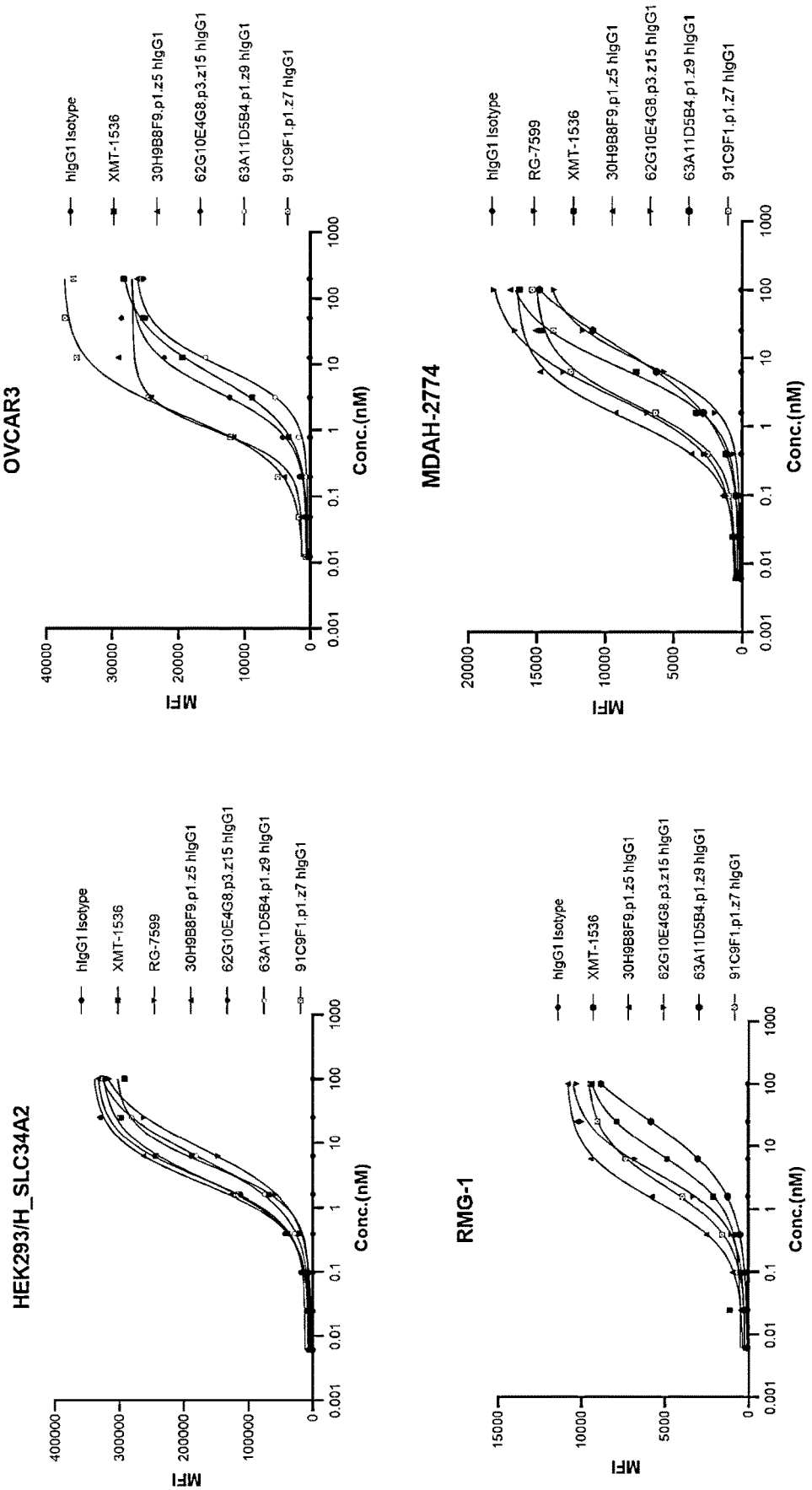
FIG. 18 compares selected humanized antibodies to benchmark ones with respect to SLC34A2 binding on different cell lines.
Figure 19:
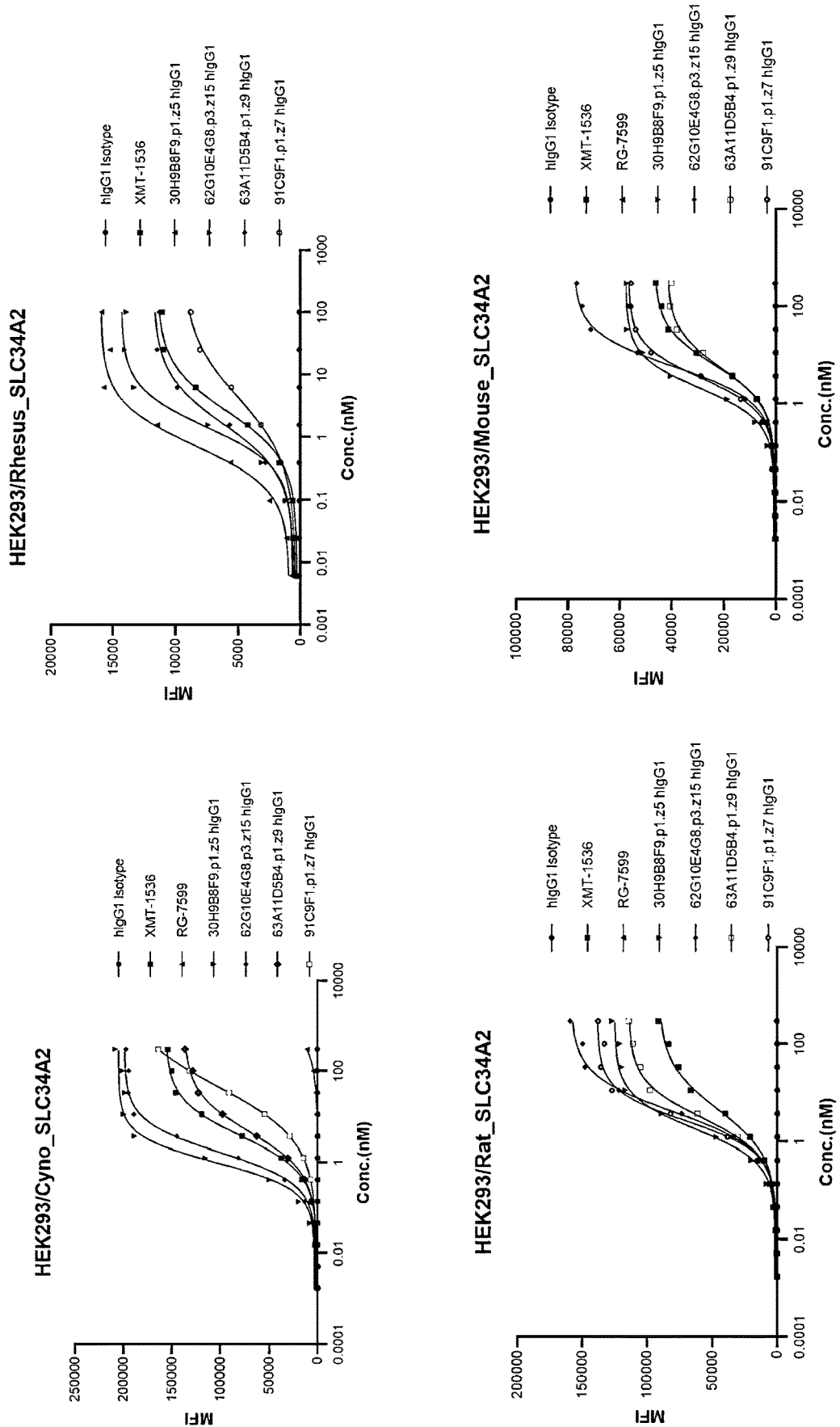
FIG. 19 compares the cross-reactivity of the selected humanized antibodies to benchmark ones.
Figure 20A:
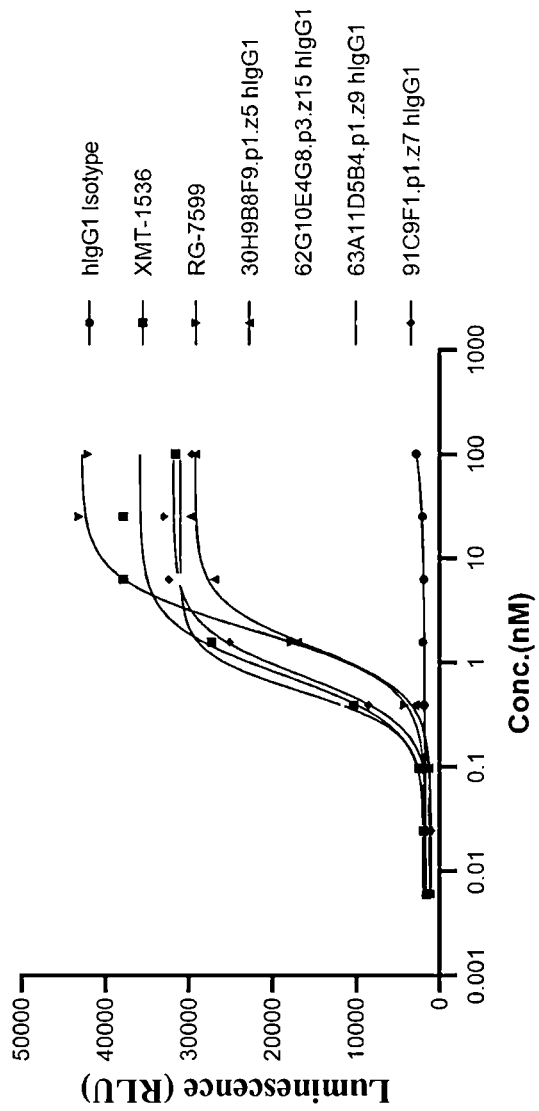
FIG. 20A-B compare the selected humanized antibodies to benchmark ones with respect to ADCC activities against different cells.
Figure 20B:
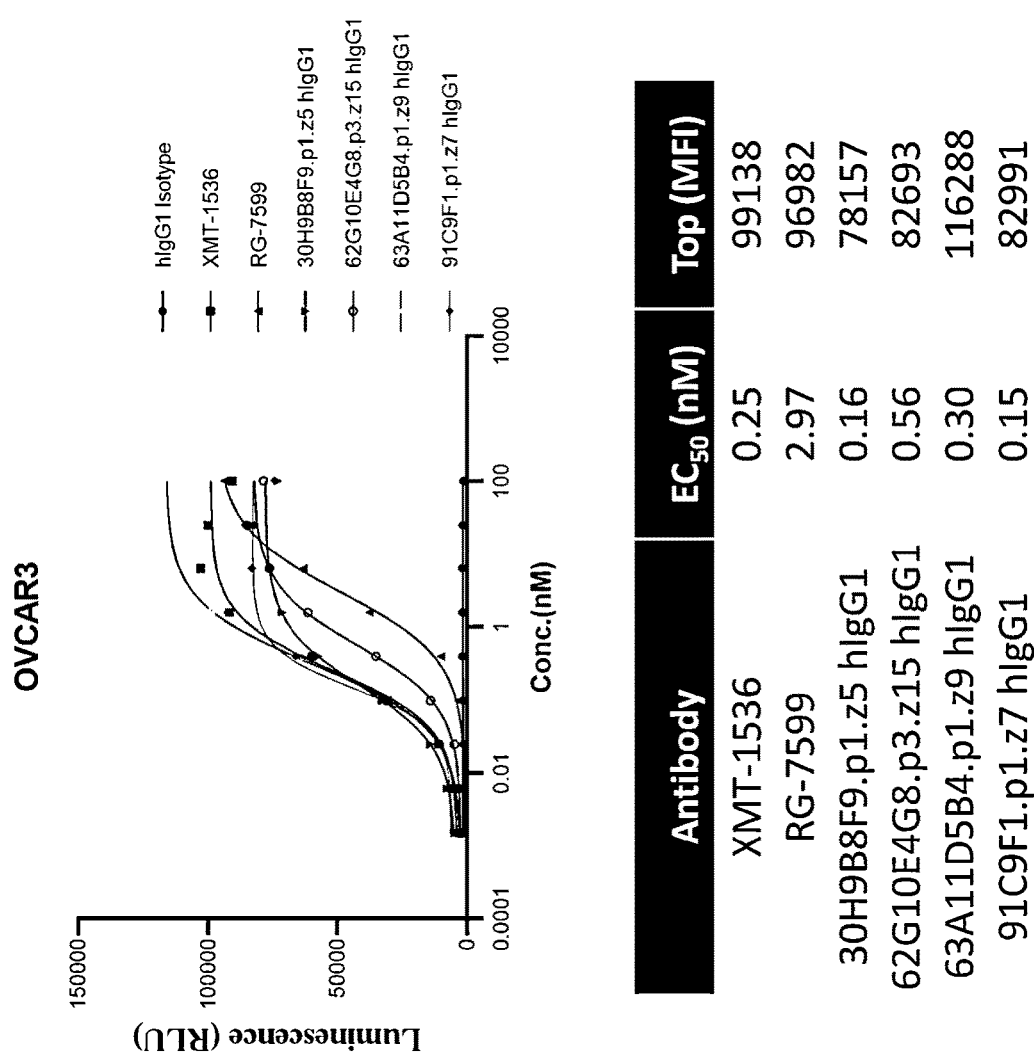

The candidate antibodies were subjected to further testing with comparison to the benchmark antibodies, XMT-1536 and RG-7599. FIG. 18 shows the comparison of binding to human SLC34A2 on different cell types. FIG. 19 compares the antibodies for their cross-reactivity to the SLC34A2 protein from different species. FIG. 20A-B compare their ADCC induction activities.

The above results are summarized in Table 20, which shows that the instantly developed antibodies outperformed the benchmarks (XMT-1536 and RG-7599) significantly in many aspects.

TABLE 20

Summary of Comparison

| Assays | 30H9B8F9 | 62G10E4G8 | 63A11D5B4 | 91C9F1 | BMK-01 (XMT-1536) | BMK-02 (RG-7599) |
|---|---|---|---|---|---|---|
| Binding-HEK293 | 2.40 nM | 2.86 nM | 5.87 nM | 2.72 nM | 4.27 nM | 8.25 nM |
| Binding-OVCAR3 | 0.90 nM | 3.80 nM | 9.10 nM | 2.40 nM | 6.80 nM | |
| Binding-RMG-1 | 1.40 nM | 3.70 nM | 28.30 nM | 2.30 nM | 7.20 nM | |
| Binding-MDAH2774 | 1.28 nM | 2.82 nM | 15.14 nM | 2.06 nM | 7.09 nM | 8.74 nM |
| Cross-species-Cyno | 0.97 nM | 1.63 nM | 4.45 nM | 45.67 nM | 3.72 nM | 1080.00 nM |
| Cross-species-Rhesus | 0.7 nM | 1.4 nM | 1.6 nM | 4.2 nM | 2.6 nM | |
| Cross-species-Rat | 1.81 nM | 4.04 nM | 3.04 nM | 2.62 nM | 4.48 nM | 714.80 nM |
| Cross-species-Mouse | 2.06 nM | 5.74 nM | 5.38 nM | 3.34 nM | 6.13 nM | 411.70 nM |
| ADCC-HEK293 | 1.40 nM | 1.55 nM | 0.52 nM | 0.75 nM | 0.76 nM | 2.02 nM |
| ADCC-OVCAR3 | 0.16 nM | 0.56 nM | 0.30 nM | 0.15 nM | 0.25 nM | 2.97 nM |
| Cytotoxic Effect - MDAH-2774 | 0.21 nM | 0.24 nM | 1.50 nM | 0.39 nM | 0.28 nM | 6.83 nM |
| Cytotoxic Effect - OVCAR3 | 0.020 nM | 0.025 nM | 0.060 nM | 0.014 nM | 0.029 nM | 0.325 nM |

The present disclosure is not to be limited in scope by the specific embodiments described which are intended as single illustrations of individual aspects of the disclosure, and any compositions or methods which are functionally equivalent are within the scope of this disclosure. It will be apparent to those skilled in the art that various modifications and variations can be made in the methods and compositions of the present disclosure without departing from the spirit or scope of the disclosure. Thus, it is intended that the present disclosure cover the modifications and variations of this disclosure provided they come within the scope of the appended claims and their equivalents.

All publications and patent applications mentioned in this specification are herein incorporated by reference to the same extent as if each individual publication or patent application was specifically and individually indicated to be incorporated by reference.

What is claimed is:

1. An antibody or fragment thereof having binding specificity to a human solute carrier 34 A2 (SLC34A2) protein, wherein the antibody or fragment thereof comprises a heavy chain variable region comprising heavy chain complementarity determining regions CDRH1, CDRH2, and CDRH3 and a light chain variable region light chain comprising complementarity determining regions CDRL1, CDRL2, and CDRL3, and wherein:

(a) the CDRH1 comprises the amino acid sequence of SEQ ID NO: 51,
the CDRH2 comprises the amino acid sequence of SEQ ID NO: 52 or 57,
the CDRH3 comprises the amino acid sequence of SEQ ID NO: 53,
the CDRL1 comprises the amino acid sequence of SEQ ID NO: 54,
the CDRL2 comprises the amino acid sequence of SEQ ID NO: 55, and
the CDRL3 comprises the amino acid sequence of SEQ ID NO: 56, (b) the CDRH1 comprises the amino acid sequence of SEQ ID NO: 66,
the CDRH2 comprises the amino acid sequence of SEQ ID NO: 67 or 72,
the CDRH3 comprises the amino acid sequence of SEQ ID NO: 68,
the CDRL1 comprises the amino acid sequence of SEQ ID NO: 69,
the CDRL2 comprises the amino acid sequence of SEQ ID NO: 70, and
the CDRL3 comprises the amino acid sequence of SEQ ID NO: 71, (c) the CDRH1 comprises the amino acid sequence of SEQ ID NO: 81,
the CDRH2 comprises the amino acid sequence of SEQ ID NO: 82 or 87,
the CDRH3 comprises the amino acid sequence of SEQ ID NO: 83,
the CDRL1 comprises the amino acid sequence of SEQ ID NO: 84,
the CDRL2 comprises the amino acid sequence of SEQ ID NO: 85, and
the CDRL3 comprises the amino acid sequence of SEQ ID NO: 86, or (d) the CDRH1 comprises the amino acid sequence of SEQ ID NO: 96,
the CDRH2 comprises the amino acid sequence of SEQ ID NO: 97 or 102,
the CDRH3 comprises the amino acid sequence of SEQ ID NO: 98 or 103,
the CDRL1 comprises the amino acid sequence of SEQ ID NO: 99,
the CDRL2 comprises the amino acid sequence of SEQ ID NO: 100, and
the CDRL3 comprises the amino acid sequence of SEQ ID NO: 101.

2. The antibody or fragment thereof of claim 1, wherein the CDRH1 comprises the amino acid sequence of SEQ ID NO: 51, the CDRH2 comprises the amino acid sequence of SEQ ID NO: 52, the CDRH3 comprises the amino acid sequence of SEQ ID NO: 53, the CDRL1 comprises the amino acid sequence of SEQ ID NO: 54, the CDRL2 comprises the amino acid sequence of SEQ ID NO: 55, and the CDRL3 comprises the amino acid sequence of SEQ ID NO: 56.

3. The antibody or fragment thereof of claim 2, wherein the heavy chain variable region comprises an amino acid sequence selected from the group consisting of SEQ ID NO: 1 and 58-61, and the light chain variable region comprises an amino acid sequence selected from the group consisting of SEQ ID NO: 2 and 62-65.

4. The antibody or fragment thereof of claim 2, wherein the heavy chain variable region comprises the amino acid sequence of SEQ ID NO:59, and the light chain variable region comprises the amino acid sequence of SEQ ID NO:62.

5. The antibody or fragment thereof of claim 1, wherein the CDRH1 comprises the amino acid sequence of SEQ ID NO: 66, the CDRH2 comprises the amino acid sequence of SEQ ID NO: 67 or 72, the CDRH3 comprises the amino acid sequence of SEQ ID NO: 68, the CDRL1 comprises the amino acid sequence of SEQ ID NO: 69, the CDRL2 comprises the amino acid sequence of SEQ ID NO: 70, and the CDRL3 comprises the amino acid sequence of SEQ ID NO: 71.

6. The antibody or fragment thereof of claim 5, wherein the CDRH2 comprises the amino acid sequence of SEQ ID NO: 67.

7. The antibody or fragment thereof of claim 5, wherein the heavy chain variable region comprises an amino acid sequence selected from the group consisting of SEQ ID NO: 3 and 73-76, and the light chain variable region comprises an amino acid sequence selected from the group consisting of SEQ ID NO: 4 and 77-80.

8. The antibody or fragment thereof of claim 5, wherein the heavy chain variable region comprises the amino acid sequence of SEQ ID NO:76, and the light chain variable region comprises the amino acid sequence of SEQ ID NO:79.

9. The antibody or fragment thereof of claim 1, wherein the CDRH1 comprises the amino acid sequence of SEQ ID NO: 81, the CDRH2 comprises the amino acid sequence of SEQ ID NO: 82 or 87, the CDRH3 comprises the amino acid sequence of SEQ ID NO: 83, the CDRL1 comprises the amino acid sequence of SEQ ID NO: 84, the CDRL2 comprises the amino acid sequence of SEQ ID NO: 85, and the CDRL3 comprises the amino acid sequence of SEQ ID NO: 86.

10. The antibody or fragment thereof of claim 9, wherein the CDRH2 comprises the amino acid sequence of SEQ ID NO: 82.

11. The antibody or fragment thereof of claim 9, wherein the heavy chain variable region comprises an amino acid sequence selected from the group consisting of SEQ ID NO: 5 and 88-91, and the light chain variable region comprises an amino acid sequence selected from the group consisting of SEQ ID NO: 6 and 92-95.

12. The antibody or fragment thereof of claim 9, wherein the heavy chain variable region comprises the amino acid sequence of SEQ ID NO:90, and the light chain variable region comprises the amino acid sequence of SEQ ID NO:92.

13. The antibody or fragment thereof of claim 1, wherein the CDRH1 comprises the amino acid sequence of SEQ ID NO: 96, the CDRH2 comprises the amino acid sequence of SEQ ID NO: 97 or 102, the CDRH3 comprises the amino acid sequence of SEQ ID NO: 98 or 103, the CDRL1 comprises the amino acid sequence of SEQ ID NO: 99, the CDRL2 comprises the amino acid sequence of SEQ ID NO: 100, and the CDRL3 comprises the amino acid sequence of SEQ ID NO: 101.

14. The antibody or fragment thereof of claim 13, wherein the CDRH2 comprises the amino acid sequence of SEQ ID NO: 97, and the CDRH3 comprises the amino acid sequence of SEQ ID NO: 98.

15. The antibody or fragment thereof of claim 13, wherein the heavy chain variable region comprises an amino acid sequence selected from the group consisting of SEQ ID NO: 7 and 104-107, and the light chain variable region comprises an amino acid sequence selected from the group consisting of SEQ ID NO: 8 and 108-111.

16. The antibody or fragment thereof of claim 13, wherein the heavy chain variable region comprises the amino acid sequence of SEQ ID NO: 105, and the light chain variable region comprises the amino acid sequence of SEQ ID NO:110.

17. An isolated polynucleotide encoding the antibody or fragment thereof of claim 1.

* * * * *

```
                         SEQUENCE LISTING

Sequence total quantity: 111
SEQ ID NO: 1              moltype = AA  length = 119
FEATURE                   Location/Qualifiers
source                    1..119
                          mol_type = protein
                          organism = Mus musculus
SEQUENCE: 1
QVQLQQPGAE LVKPGASVKM SCKTSGYTFT TNNMHWVKQT PGQGLEWIGA IYPGNGATAY   60
NQKFKGKATL TADKSSSTAY MQLSSLTSEA SAVYYCARGM YGHGAMDYWG QGTSVIVSS    119

SEQ ID NO: 2              moltype = AA  length = 107
FEATURE                   Location/Qualifiers
source                    1..107
                          mol_type = protein
                          organism = Mus musculus
SEQUENCE: 2
DIVMTQSHKF MSRSVGDRVR ITCKASQDVG TAVAWYQQKP GQSPKLLIYW ATTRHSGVPD   60
RFTGSGSGTD FIFTISNVQS EDLADYFCQQ YSSNPLTFGA GTKLELK                 107

SEQ ID NO: 3              moltype = AA  length = 120
FEATURE                   Location/Qualifiers
source                    1..120
                          mol_type = protein
                          organism = Mus musculus
SEQUENCE: 3
QVQLQQSGAE VVKPGASVKM SCKASGYTFP SYITHWVKQT PGQGLEWIGA IYPGNGDTSY   60
```

```
IQKFKGKATL TADKSSSTAY MQLSSLTSED SAVYYCARGT YGTSAWFTYW GQGTLVTVSA   120

SEQ ID NO: 4              moltype = AA   length = 107
FEATURE                   Location/Qualifiers
source                    1..107
                          mol_type = protein
                          organism = Mus musculus
SEQUENCE: 4
DIVLTQSPAT LSVTPGDSVS LSCRARQNIG NNLYWYQQKS HESPRLLIKY ASQSISGIPS   60
RFSGSGSGTD FTLTINSVET EDFGVYFCQQ SFSWPLTFGA GTKLELK                107

SEQ ID NO: 5              moltype = AA   length = 120
FEATURE                   Location/Qualifiers
source                    1..120
                          mol_type = protein
                          organism = Mus musculus
SEQUENCE: 5
QVQLQQPGAE LVKPGASVKM SCRTSGYTFI TYNMHWVKQT PGQGREWIGA IYPGNGDTSY   60
NQKFKGKATL TADKSSSTAY MQLNSLTSED SAVYYCSIST IITTGAVDYW GQGTSVTVAS  120

SEQ ID NO: 6              moltype = AA   length = 107
FEATURE                   Location/Qualifiers
source                    1..107
                          mol_type = protein
                          organism = Mus musculus
SEQUENCE: 6
DIVMTQSHKF MSTSVGDRVS ITCKASQDVG TAVAWYQQKA GQSPKLLIYW TSTRHTGVPD   60
RFTGSGSGTD FTLIIRSLQS EDLADYFCQQ YSRIPLTFGS GTKLEIK                107

SEQ ID NO: 7              moltype = AA   length = 120
FEATURE                   Location/Qualifiers
source                    1..120
                          mol_type = protein
                          organism = Mus musculus
SEQUENCE: 7
EVQLQQSGPE LVKPGTSVKI SCKTSGFFFT EYIIHWVKQS HGRSLEWIGG IIPNNGVTNY   60
KQNFRGKAAL TADKSSNTAY MELRSLTSED SAVYYCARWR NGYYSAMDSW GQGTSVTVSS  120

SEQ ID NO: 8              moltype = AA   length = 107
FEATURE                   Location/Qualifiers
source                    1..107
                          mol_type = protein
                          organism = Mus musculus
SEQUENCE: 8
DIVVTQSHKF MSTSLGDRVS ITCTASQDVG TAVAWYQQKP GHSPKLLIYW ASTRHTGVPE   60
RFTGSGSGTD FTLTITNVQS EDLADYFCQQ YRTSPLTFGV GTKLELK                107

SEQ ID NO: 9              moltype = AA   length = 119
FEATURE                   Location/Qualifiers
source                    1..119
                          mol_type = protein
                          organism = Mus musculus
SEQUENCE: 9
QVQLQQPGAE LVKPGASVKM SCKASGYTFT SYNIHWVKQT PGQGLEWIGA VYPGNGDTSY   60
NQKFRGKATL TSDKSSNTAY MQLSSLTSED SAVFYCARGI YGHGAMDSWG QGTSVTVSS   119

SEQ ID NO: 10             moltype = AA   length = 107
FEATURE                   Location/Qualifiers
source                    1..107
                          mol_type = protein
                          organism = Mus musculus
SEQUENCE: 10
DIVMTQSHKF MSTSLGARVS ITYKASQDVG TAVAWYQQKP GQSPKLLIYW ASTRHTGVPD   60
RFTGSGSGTD FTLTISNVQS EDLADYFCQQ YSSNPLTFGA GTKLELK                107

SEQ ID NO: 11             moltype = AA   length = 120
FEATURE                   Location/Qualifiers
source                    1..120
                          mol_type = protein
                          organism = Mus musculus
SEQUENCE: 11
QVQLQQTGAE LVKPGASVKM SCKASGYTFT GYIIHWIKQR PGQGLEWIGA IYPGNGDTSY   60
NQKIKGRATL TADKSSTTAY MQLSSLTSED SAVYYCARGD YGNPAWFAYW GQGTLVTVSA  120

SEQ ID NO: 12             moltype = AA   length = 107
FEATURE                   Location/Qualifiers
source                    1..107
                          mol_type = protein
                          organism = Mus musculus
```

```
SEQUENCE: 12
DVVLTQSPAT LSVTPGDRVS LSCRASQSIS NYLYWYQQKA HESPRLLIKF ASQSISGIPS    60
RFRGSGSGTD FTLSINSVET EDFGMYFCQQ SNKWPLTFGA GTKLELK                 107

SEQ ID NO: 13           moltype = AA  length = 119
FEATURE                 Location/Qualifiers
source                  1..119
                        mol_type = protein
                        organism = Mus musculus
SEQUENCE: 13
QVQLQQPGAE LVKPGASVKM SCKASGYTFT SYNMQWVKQT YGQGLEWIGA ISPGSGETSY    60
NQNFKVKATL TADKISSTAY MQLSSLTSED SAVYYCARAA RAEGWFAYWG QGTLVTVSA    119

SEQ ID NO: 14           moltype = AA  length = 107
FEATURE                 Location/Qualifiers
source                  1..107
                        mol_type = protein
                        organism = Mus musculus
SEQUENCE: 14
DIVMTQSHKF MSTSVGDRVS ITCKASQDVG HAVVWYQQKP GQFPKLLIYW ASTRHAGVPD    60
RFTGSGSGTD FTLTISNVQS EDLADYFCQQ FRSIPLTFGS GTKLEIK                 107

SEQ ID NO: 15           moltype = AA  length = 121
FEATURE                 Location/Qualifiers
source                  1..121
                        mol_type = protein
                        organism = Mus musculus
SEQUENCE: 15
DVKLVESGGG LVKLGGSLKL SCAASGFTFS SYFMSWIRQT PEKRVDLVAV INSNGGSTYS    60
PDTVKGRFTI SRDNAKNTLY LQMTSLKSED TALYYCARHF YSYDGAWFPY WGQGTLVTVS   120
A                                                                  121

SEQ ID NO: 16           moltype = AA  length = 107
FEATURE                 Location/Qualifiers
source                  1..107
                        mol_type = protein
                        organism = Mus musculus
SEQUENCE: 16
DIVMTQSHKF MSTLVGDRVS ITCKASQDVS TSVAWYQQKP GQSPKLLIYW ASTRHTGVPD    60
RFTGSGSGTD FTLTISSVQA EDLALYYCQQ HHSTPITFGV GTKLELK                 107

SEQ ID NO: 17           moltype = AA  length = 121
FEATURE                 Location/Qualifiers
source                  1..121
                        mol_type = protein
                        organism = Mus musculus
SEQUENCE: 17
QVQLQQPGAV LVKPGASVKM SCKASGYTFT SYIIHWVKQT PGQGLEWVGA IYPGNGDASS    60
IQKFKGKATL TVDKSSSTAY MQLSSLTSAD SAVYYCARGH YYGSAAWFAY WGQGTLVTVS   120
A                                                                  121

SEQ ID NO: 18           moltype = AA  length = 107
FEATURE                 Location/Qualifiers
source                  1..107
                        mol_type = protein
                        organism = Mus musculus
SEQUENCE: 18
DILLTQSPAI LSVSPGERVS FSCRASQNIG TGIHWYQQRT NGSLRLLIKY ASESISGIPS    60
RFSGSGSGTD FTLSINSVES EDIADYYCQQ SNSWPLTFGA GTKLELK                 107

SEQ ID NO: 19           moltype = AA  length = 122
FEATURE                 Location/Qualifiers
source                  1..122
                        mol_type = protein
                        organism = Mus musculus
SEQUENCE: 19
EVQLQQSGPE LVKPGASVKI SCKTSGFTFT EYTMHWVKQS HGKSLEWIGG INPNNGISSY    60
NQNFKGKATL TVDKSSSTAY MELRSLTSED STVYYCARCR YYDTSYYDMD YWGQGTSVTV   120
SS                                                                 122

SEQ ID NO: 20           moltype = AA  length = 107
FEATURE                 Location/Qualifiers
source                  1..107
                        mol_type = protein
                        organism = Mus musculus
SEQUENCE: 20
DIQMTQTTSS LSASLGDRVT ISCRASQDIR NFLNWYQQKP DGTVKLLIYY TSRLHSGVPS    60
RFSGSGSGTD YSLTISNLEE EDIATYFCQQ SNTLPWTFGG GTKLEIK                 107
```

```
SEQ ID NO: 21          moltype = AA   length = 120
FEATURE                Location/Qualifiers
source                 1..120
                       mol_type = protein
                       organism = Mus musculus
SEQUENCE: 21
QVQLQQPGAV LVKPGASVKM SCKASGYTFT SYNLHWVKQT PGQGLEWIGA IYPGNGDTSY    60
IQKFKGKATL TADKSSSTAY MQLSSLTSED SAVYYCARGK YGNYEGFAYW GQGTLVTVSA   120

SEQ ID NO: 22          moltype = AA   length = 107
FEATURE                Location/Qualifiers
source                 1..107
                       mol_type = protein
                       organism = Mus musculus
SEQUENCE: 22
DILLTQSPAI LSVSPGERVS ISCRASQSIG TSIYWYQQRR NGSPRLLIKF ASESISGIPS    60
RFSGSGSGTD FTLSINSVES EDIADYYCQQ NNRWPFTFGS GTKLEIK                 107

SEQ ID NO: 23          moltype = AA   length = 119
FEATURE                Location/Qualifiers
source                 1..119
                       mol_type = protein
                       organism = Mus musculus
SEQUENCE: 23
QVQLLQPGAE LVKPGASVLM SCKTSGYTFT TYNMHWVKQT PGQGLEWTGV ISPGNGATSY    60
TQKFKGKATL TADKSSNTVY MQLRSLTSED SAVYNCARGY GNTGAMDHWG QGTSVTVSS    119

SEQ ID NO: 24          moltype = AA   length = 107
FEATURE                Location/Qualifiers
source                 1..107
                       mol_type = protein
                       organism = Mus musculus
SEQUENCE: 24
DIVMTQSHKF ISTSVGERVI ITCKASQDVG TAVTWYQRKP RQSPKLLISW ASTRHTGVPD    60
RFTGSGSGTD FTFTINNVQS EDLADYFCQQ YRAIPLTFGA GTKLELK                 107

SEQ ID NO: 25          moltype = AA   length = 119
FEATURE                Location/Qualifiers
source                 1..119
                       mol_type = protein
                       organism = Mus musculus
SEQUENCE: 25
DVKLVESGGG LIKLGGSLKL SCAASGFTFS GYYMSWFRQT PEKRLELVAV INSNGGSTYY    60
AVTVKGRFTI SRDNAKNTLY LQMSSLKSED TALYYCARHE GSQAWFAHWG QGTLVTVSA    119

SEQ ID NO: 26          moltype = AA   length = 107
FEATURE                Location/Qualifiers
source                 1..107
                       mol_type = protein
                       organism = Mus musculus
SEQUENCE: 26
DIVMTQSHKF MSTSVGDRVS ITCKASQDVT TAVAWYQQKP GQSPKLLIYW ASTRHTGVPD    60
RFTGSGSGTD YTLTISSVQA EDLALYYCQQ HHSTPLTFGA GTKLELK                 107

SEQ ID NO: 27          moltype = AA   length = 120
FEATURE                Location/Qualifiers
source                 1..120
                       mol_type = protein
                       organism = Mus musculus
SEQUENCE: 27
DVKLVESGGG LVRLGGSLKL SCAASGFTFS SHYMSWVRQT PKKRLELVAT INSSGGNTYY    60
PDTVKGRFTI SRDNARNTLF LQMTSLKSED TALYYCARQP INTVAYFDYW GQGTTLTVSS   120

SEQ ID NO: 28          moltype = AA   length = 107
FEATURE                Location/Qualifiers
source                 1..107
                       mol_type = protein
                       organism = Mus musculus
SEQUENCE: 28
DIVMTQSHEF MSTSVGARVS ITCKASQDLT TAVAWYQQKP GQSPKLLIYW ASTRHIGVPD    60
RFTGSGSGAD YTLTISSVQA EDLALYYCQQ YHSTPLTFGA GTKLELK                 107

SEQ ID NO: 29          moltype = AA   length = 120
FEATURE                Location/Qualifiers
source                 1..120
                       mol_type = protein
                       organism = Mus musculus
SEQUENCE: 29
QVHQQQSGPE LVKPGASVRI SCKASGYTFT SYYIHWVKQR PGQGLEWIGC IYPGNLFTKY    60
```

```
NEKFKDKATL TADTSSTTAY MHLSSLTSED SAVYFCARFL NWNAWYFDVW GAGTTVSVSS    120

SEQ ID NO: 30             moltype = AA   length = 112
FEATURE                   Location/Qualifiers
source                    1..112
                          mol_type = protein
                          organism = Mus musculus
SEQUENCE: 30
DVLMTQTPLS LPVSLGDQAS ISCRSSQSIE HSNGNTNLEW YLQKPGQSPR LLIYKVSNRF     60
SGVPDRFSGS GSGTDFTLKI TGVEAEDLGV YYCFQGSHFP WTFGGGTKLE IK            112

SEQ ID NO: 31             moltype = AA   length = 119
FEATURE                   Location/Qualifiers
source                    1..119
                          mol_type = protein
                          organism = Mus musculus
SEQUENCE: 31
QVQLQQSGAE VVNSGASVKM SCKASGYTFT TYNMHWVKQT PGQGLEWIGA IYPGNGDTSY     60
NQRFKGKATF TADRSSGTAY MQLSSLPSED SAVYYCARGG YANGALVDWG QGTLVTVSA    119

SEQ ID NO: 32             moltype = AA   length = 107
FEATURE                   Location/Qualifiers
source                    1..107
                          mol_type = protein
                          organism = Mus musculus
SEQUENCE: 32
DILMTQSHKF MSTSVGDRVT ITCKASQDVG TAVAWYQNKP GQSPKLLIFW TSTRHTGVPD     60
RFTGSGSGTD FTLTISNVQS EDLADYFCQQ YSRQPLTFGP GTKLEIK                 107

SEQ ID NO: 33             moltype = AA   length = 121
FEATURE                   Location/Qualifiers
source                    1..121
                          mol_type = protein
                          organism = Mus musculus
SEQUENCE: 33
QVQLQQPGAE VVKPGASVKM SCKASGYTFT SYIIHWVKQA PGQGLEWIGA IYPGNGDTSY     60
SQRFKGKAKL TADKSSSTAY MQLNSLTSED SVVYYCARGN NYGSPAWFGY WGQGTLVTVS   120
A                                                                   121

SEQ ID NO: 34             moltype = AA   length = 107
FEATURE                   Location/Qualifiers
source                    1..107
                          mol_type = protein
                          organism = Mus musculus
SEQUENCE: 34
DIVLTQSPVT LSVTPGDRVS LSCRASQSIG NFLYWYQQKS HESPRLLIKY ASQSMSGIPS     60
RFSGSGSGTD FTLSISRVET EDFGMYFCQQ SNSWPVTFGA GTKLELK                 107

SEQ ID NO: 35             moltype = AA   length = 120
FEATURE                   Location/Qualifiers
source                    1..120
                          mol_type = protein
                          organism = Mus musculus
SEQUENCE: 35
QVQLQQPGAE LVKPGASVRM SCKASAYTFT TYNLHWVKQT PGQGLEWIGA ISPGNGVTSY     60
NQKFRGKATL TADKSSSTAY MQLSSLTSED SAVYYCARGY GYSVGAMDYW GQGTSVTVSS   120

SEQ ID NO: 36             moltype = AA   length = 107
FEATURE                   Location/Qualifiers
source                    1..107
                          mol_type = protein
                          organism = Mus musculus
SEQUENCE: 36
DIQMTQTTSS LSASLGDRVN ISCSASQGIG NFLNWYQQKP DGTVKLLIYY TSSLHSGVPP     60
RFSGSGSGTD YSLTISNLEP EDIATYYCQQ YHKLPLTFGA GTKLELK                 107

SEQ ID NO: 37             moltype = AA   length = 119
FEATURE                   Location/Qualifiers
source                    1..119
                          mol_type = protein
                          organism = Mus musculus
SEQUENCE: 37
QVQLQQPGAE LVKPGASVMM SCKASGYTFS NHNLHWLKKT PGQGLDWIGA IYPGNGDTSY     60
NQKFKGRATL TVDKSSNTAY MQFSSLTSED SAVFYCARGK YGNGAMDYWG QGTAVTVSS    119

SEQ ID NO: 38             moltype = AA   length = 107
FEATURE                   Location/Qualifiers
source                    1..107
                          mol_type = protein
```

```
                        organism = Mus musculus
SEQUENCE: 38
DIVMTQSHKF MSTSVGDRVS ITCRASQDVG TAVVWYQQKL GQSPKLLFDW ASSRHTGVPD    60
RFTGSGSGTD FTLTITDVQS EDLADYFCQQ YSRQPLTFGA GTKLELK                107

SEQ ID NO: 39           moltype = AA   length = 119
FEATURE                 Location/Qualifiers
source                  1..119
                        mol_type = protein
                        organism = Mus musculus
SEQUENCE: 39
EVQLQQSGPE LVKPGAAVKI SCKTSGYTFT DYTMHWVRQS HGKSLEWIGG IHPNNGGTGY    60
NQKLRGKATL TVDKSSSTAY MELRSLTSDD SAVYYCARGR ESDGWFTYWG QGTLVTFSA    119

SEQ ID NO: 40           moltype = AA   length = 107
FEATURE                 Location/Qualifiers
source                  1..107
                        mol_type = protein
                        organism = Mus musculus
SEQUENCE: 40
DVHMTQTTSS LSASLGDRVT ITCSASQGIG NSLNWYQQQP DGTVKLLIYY TSRLHSGVPS    60
RFSGSGSGTD YSLTISNLEP EDLATYYCQQ YSRFPPTFGG GTKLEIK                107

SEQ ID NO: 41           moltype = AA   length = 123
FEATURE                 Location/Qualifiers
source                  1..123
                        mol_type = protein
                        organism = Mus musculus
SEQUENCE: 41
DVKLVESGGD LVKLGGSLKL SCAASGFTFS NYYMSWVRQT PEKRLELVAV INSNGGTTYY    60
PDNMKGRFTI SRDNAKNTLY LQTSSLKSED TALYYCGRHE HYYGTNIAWF AYWGQGTLVT   120
VSA                                                                123

SEQ ID NO: 42           moltype = AA   length = 107
FEATURE                 Location/Qualifiers
source                  1..107
                        mol_type = protein
                        organism = Mus musculus
SEQUENCE: 42
DIVMTQSHKF MSTSVGDRVS ITCKASQDVT TAVAWYQQKP GQSPKLLIYW ASTRHTGVPD    60
RFTGSGSGTD HTLTISSVQA EDLALYYCQQ HYSTPVTFGG GTKLEIK                107

SEQ ID NO: 43           moltype = AA   length = 120
FEATURE                 Location/Qualifiers
source                  1..120
                        mol_type = protein
                        organism = Mus musculus
SEQUENCE: 43
QVQLQQPGAD LVKPGASVKL SCKASGFTFT SYIIHWVKQT PGQGLEWIGA IYPGNGDTSY    60
IQKFKGRATL TADKSSTTAY MQLGGLTSED SAVYYCARGT YGSSAWFVYW GQGTLVTVSA   120

SEQ ID NO: 44           moltype = AA   length = 107
FEATURE                 Location/Qualifiers
source                  1..107
                        mol_type = protein
                        organism = Mus musculus
SEQUENCE: 44
DIVLTQSPAT LSVTPGDSVS LSCRASQSIS NNLYWYQQKS HESPRLLIKY ASQSISGIPS    60
RFRGSGSGTD FTLSINSVET EDFGMYFCQQ SNSWPLTFGA GTKLELK                107

SEQ ID NO: 45           moltype = AA   length = 121
FEATURE                 Location/Qualifiers
source                  1..121
                        mol_type = protein
                        organism = Mus musculus
SEQUENCE: 45
QVQLQQPGAE VVRPGASVKM SCKASGYTFT SYIVHWVKQP PGQGLEWIGA IYPGNGDTSY    60
IQKFKGRATL TADKSSSTVY MQLSSLTSED SAVYYCARGH YYGSAAWFGF WGQGTLVTVS   120
A                                                                  121

SEQ ID NO: 46           moltype = AA   length = 107
FEATURE                 Location/Qualifiers
source                  1..107
                        mol_type = protein
                        organism = Mus musculus
SEQUENCE: 46
DILLTQSPAI LSVSPGERVS FSCRASQNIG TSIHWYQQRT NDSPRLLMRY ASESVSGIPS    60
RFSGSGSGTD FTLSINSVES EDIADYYCQQ SNTWPLTFGA GTKLELK                107
```

```
SEQ ID NO: 47              moltype = AA   length = 116
FEATURE                    Location/Qualifiers
source                     1..116
                           mol_type = protein
                           organism = Mus musculus
SEQUENCE: 47
EVKLVESGGN LVKPGGSLKL SCAASGFTFS SYAMSWVRQT PEKRLEWVAS ISNGGTTYYP    60
DSVKGRFTIS RDVARNILYL QMTSLRSEDT AMYYCARTHY RDFVYWGQGT LVTVSA       116

SEQ ID NO: 48              moltype = AA   length = 112
FEATURE                    Location/Qualifiers
source                     1..112
                           mol_type = protein
                           organism = Mus musculus
SEQUENCE: 48
EIVLTQAAFS NPVTLGTSAS ISCRSSKSLL HSNGITYLYW YLQKPGQSPQ LLIYQMSNLA    60
SGVPDRFSCS GSGTDFTLRI SRVEAEDVGV YYCAQNLEFP WTFGGGTKLE IK           112

SEQ ID NO: 49              moltype = AA   length = 119
FEATURE                    Location/Qualifiers
source                     1..119
                           mol_type = protein
                           organism = Mus musculus
SEQUENCE: 49
QVQLQQPGAE LVKPGASVKM SCKTSGYTFT TNNMHWVKQT PGQGLEWIGA IYPGNGATAY    60
NQKFKGKATL TADKSSSTAY MQLSSLTSEA SAVYYCARGM YGHGAMDYWG QGTSVIVSS    119

SEQ ID NO: 50              moltype = AA   length = 107
FEATURE                    Location/Qualifiers
source                     1..107
                           mol_type = protein
                           organism = Mus musculus
SEQUENCE: 50
DIVLTQSPAT LSVTPGDSVS LSCRARQNIG NNLYWYQQKS NESPRLLIKY ASQSISGIPS    60
RFSGSGSGTD FTLTINSVET EDFGVYFCQQ SFSWPLTFGA GTKLELK                 107

SEQ ID NO: 51              moltype = AA   length = 5
FEATURE                    Location/Qualifiers
source                     1..5
                           mol_type = protein
                           organism = Mus musculus
SEQUENCE: 51
TNNMH                                                               5

SEQ ID NO: 52              moltype = AA   length = 17
FEATURE                    Location/Qualifiers
source                     1..17
                           mol_type = protein
                           organism = Mus musculus
SEQUENCE: 52
AIYPGSGATA YNQKFKG                                                  17

SEQ ID NO: 53              moltype = AA   length = 10
FEATURE                    Location/Qualifiers
source                     1..10
                           mol_type = protein
                           organism = Mus musculus
SEQUENCE: 53
GMYGHGAMDY                                                          10

SEQ ID NO: 54              moltype = AA   length = 11
FEATURE                    Location/Qualifiers
source                     1..11
                           mol_type = protein
                           organism = Mus musculus
SEQUENCE: 54
KASQDVGTAV A                                                        11

SEQ ID NO: 55              moltype = AA   length = 7
FEATURE                    Location/Qualifiers
source                     1..7
                           mol_type = protein
                           organism = Mus musculus
SEQUENCE: 55
WATTRHS                                                             7

SEQ ID NO: 56              moltype = AA   length = 9
FEATURE                    Location/Qualifiers
source                     1..9
```

```
                        mol_type = protein
                        organism = Mus musculus
SEQUENCE: 56
QQYSSNPLT                                                             9

SEQ ID NO: 57           moltype = AA   length = 17
FEATURE                 Location/Qualifiers
source                  1..17
                        mol_type = protein
                        organism = Mus musculus
SEQUENCE: 57
AIYPGNGATA YNQKFKG                                                    17

SEQ ID NO: 58           moltype = AA   length = 119
FEATURE                 Location/Qualifiers
source                  1..119
                        mol_type = protein
                        organism = synthetic construct
SEQUENCE: 58
QVQLVQSGAE VKKPGASVKV SCKASGYTFT TNNMHWVRQA PGQGLEWMGA IYPGSGATAY     60
NQKFKGRVTM TRDTSTSTVY MELSSLRSED TAVYYCASGM YGHGAMDYWG QGTLVTVSS      119

SEQ ID NO: 59           moltype = AA   length = 119
FEATURE                 Location/Qualifiers
source                  1..119
                        mol_type = protein
                        organism = synthetic construct
SEQUENCE: 59
QVQLVQSGAE VKKPGASVKV SCKTSGYTFT TNNMHWVRQA PGQGLEWIGA IYPGSGATAY     60
NQKFKGRVTM TADTSTSTVY MELSSLRSED TAVYYCARGM YGHGAMDYWG QGTLVTVSS      119

SEQ ID NO: 60           moltype = AA   length = 119
FEATURE                 Location/Qualifiers
source                  1..119
                        mol_type = protein
                        organism = synthetic construct
SEQUENCE: 60
QVQLVQSGAE VVKPGASVKV SCKTSGYTFT TNNMHWVRQA PGQGLEWIGA IYPGSGATAY     60
NQKFKGRVTL TADKSTSTAY MELSSLRSEA TAVYYCARGM YGHGAMDYWG QGTLVTVSS      119

SEQ ID NO: 61           moltype = AA   length = 119
FEATURE                 Location/Qualifiers
source                  1..119
                        mol_type = protein
                        organism = synthetic construct
SEQUENCE: 61
QVQLVQSGAE VVKPGASVKM SCKTSGYTFT TNNMHWVKQA PGQGLEWIGA IYPGSGATAY     60
NQKFKGRATL TADKSTSTAY MELSSLRSEA TAVYYCARGM YGHGAMDYWG QGTSVTVSS      119

SEQ ID NO: 62           moltype = AA   length = 107
FEATURE                 Location/Qualifiers
source                  1..107
                        mol_type = protein
                        organism = synthetic construct
SEQUENCE: 62
DIQLTQSPSF LSASVGDRVT ITCKASQDVG TAVAWYQQKP GKAPKLLIYW ATTRHSGVPS     60
RFSGSGSGTE FTLTISSLQP EDFATYYCQQ YSSNPLTFGQ GTKLEIK                   107

SEQ ID NO: 63           moltype = AA   length = 107
FEATURE                 Location/Qualifiers
source                  1..107
                        mol_type = protein
                        organism = synthetic construct
SEQUENCE: 63
DIQLTQSPSF LSASVGDRVT ITCKASQDVG TAVAWYQQKP GKSPKLLIYW ATTRHSGVPD     60
RFSGSGSGTE FTFTISSLQP EDFATYFCQQ YSSNPLTFGQ GTKLEIK                   107

SEQ ID NO: 64           moltype = AA   length = 107
FEATURE                 Location/Qualifiers
source                  1..107
                        mol_type = protein
                        organism = synthetic construct
SEQUENCE: 64
DIQMTQSPSF LSASVGDRVT ITCKASQDVG TAVAWYQQKP GKSPKLLIYW ATTRHSGVPD     60
RFSGSGSGTE FIFTISSVQP EDFATYFCQQ YSSNPLTFGA GTKLEIK                   107

SEQ ID NO: 65           moltype = AA   length = 107
FEATURE                 Location/Qualifiers
source                  1..107
```

```
                            mol_type = protein
                            organism = synthetic construct
SEQUENCE: 65
DIVMTQSPSF LSASVGDRVT ITCKASQDVG TAVAWYQQKP GKSPKLLIYW ATTRHSGVPD    60
RFTGSGSGTD FIFTISSVQP EDFATYFCQQ YSSNPLTFGA GTKLEIK                 107

SEQ ID NO: 66           moltype = AA  length = 5
FEATURE                 Location/Qualifiers
source                  1..5
                        mol_type = protein
                        organism = Mus musculus
SEQUENCE: 66
SYITH                                                                 5

SEQ ID NO: 67           moltype = AA  length = 17
FEATURE                 Location/Qualifiers
source                  1..17
                        mol_type = protein
                        organism = synthetic construct
SEQUENCE: 67
AIYPGNADTS YIQKFKG                                                   17

SEQ ID NO: 68           moltype = AA  length = 11
FEATURE                 Location/Qualifiers
source                  1..11
                        mol_type = protein
                        organism = Mus musculus
SEQUENCE: 68
GTYGTSAWFT Y                                                         11

SEQ ID NO: 69           moltype = AA  length = 11
FEATURE                 Location/Qualifiers
source                  1..11
                        mol_type = protein
                        organism = Mus musculus
SEQUENCE: 69
RARQNIGNNL Y                                                         11

SEQ ID NO: 70           moltype = AA  length = 7
FEATURE                 Location/Qualifiers
source                  1..7
                        mol_type = protein
                        organism = Mus musculus
SEQUENCE: 70
YASQSIS                                                               7

SEQ ID NO: 71           moltype = AA  length = 9
FEATURE                 Location/Qualifiers
source                  1..9
                        mol_type = protein
                        organism = Mus musculus
SEQUENCE: 71
QQSFSWPLT                                                             9

SEQ ID NO: 72           moltype = AA  length = 17
FEATURE                 Location/Qualifiers
source                  1..17
                        mol_type = protein
                        organism = Mus musculus
SEQUENCE: 72
AIYPGNGDTS YIQKFKG                                                   17

SEQ ID NO: 73           moltype = AA  length = 120
FEATURE                 Location/Qualifiers
source                  1..120
                        mol_type = protein
                        organism = synthetic construct
SEQUENCE: 73
QVQLVQSGAE VKKPGASVKV SCKASGYTFP SYITHWVRQA PGQGLEWMGA IYPGNADTSY    60
IQKFKGRVTM TRDTSTSTVY MELSSLRSED TAVYYCARGT YGTSAWFTYW GQGTLVTVSS   120

SEQ ID NO: 74           moltype = AA  length = 120
FEATURE                 Location/Qualifiers
source                  1..120
                        mol_type = protein
                        organism = synthetic construct
SEQUENCE: 74
QVQLVQSGAE VKKPGASVKV SCKASGYTFP SYITHWVRQA PGQGLEWIGA IYPGNADTSY    60
IQKFKGRVTM TADKSTSTVY MELSSLRSED TAVYYCARGT YGTSAWFTYW GQGTLVTVSS   120
```

```
SEQ ID NO: 75           moltype = AA   length = 120
FEATURE                 Location/Qualifiers
source                  1..120
                        mol_type = protein
                        organism = synthetic construct
SEQUENCE: 75
QVQLVQSGAE VKKPGASVKV SCKASGYTFP SYITHWVKQA PGQGLEWIGA IYPGNADTSY    60
IQKFKGRVTL TADKSTSTAY MELSSLRSED TAVYYCARGT YGTSAWFTYW GQGTLVTVSS   120

SEQ ID NO: 76           moltype = AA   length = 120
FEATURE                 Location/Qualifiers
source                  1..120
                        mol_type = protein
                        organism = synthetic construct
SEQUENCE: 76
QVQLVQSGAE VVKPGASVKM SCKASGYTFP SYITHWVKQA PGQGLEWIGA IYPGNADTSY    60
IQKFKGRATL TADKSTSTAY MELSSLRSED TAVYYCARGT YGTSAWFTYW GQGTLVTVSS   120

SEQ ID NO: 77           moltype = AA   length = 107
FEATURE                 Location/Qualifiers
source                  1..107
                        mol_type = protein
                        organism = synthetic construct
SEQUENCE: 77
EIVMTQSPAT LSVSPGERAT LSCRARQNIG NNLYWYQQKP GQAPRLLIYY ASQSISGIPA    60
RFSGSGSGTE FTLTISSLQS EDFAVYYCQQ SFSWPLTFGQ GTKLEIK                 107

SEQ ID NO: 78           moltype = AA   length = 107
FEATURE                 Location/Qualifiers
source                  1..107
                        mol_type = protein
                        organism = synthetic construct
SEQUENCE: 78
EIVMTQSPAT LSVSPGERAT LSCRARQNIG NNLYWYQQKP GQSPRLLIKY ASQSISGIPA    60
RFSGSGSGTE FTLTISSLQS EDFAVYFCQQ SFSWPLTFGQ GTKLEIK                 107

SEQ ID NO: 79           moltype = AA   length = 107
FEATURE                 Location/Qualifiers
source                  1..107
                        mol_type = protein
                        organism = synthetic construct
SEQUENCE: 79
EIVLTQSPAT LSVSPGERAT LSCRARQNIG NNLYWYQQKP GQSPRLLIKY ASQSISGIPS    60
RFSGSGSGTD FTLTISSLQS EDFAVYFCQQ SFSWPLTFGQ GTKLEIK                 107

SEQ ID NO: 80           moltype = AA   length = 107
FEATURE                 Location/Qualifiers
source                  1..107
                        mol_type = protein
                        organism = synthetic construct
SEQUENCE: 80
EIVLTQSPAT LSASPGERAT LSCRARQNIG NNLYWYQQKP GQSPRLLIKY ASQSISGIPS    60
RFSGSGSGTD FTLTISSVQS EDFAVYFCQQ SFSWPLTFGA GTKLEIK                 107

SEQ ID NO: 81           moltype = AA   length = 5
FEATURE                 Location/Qualifiers
source                  1..5
                        mol_type = protein
                        organism = Mus musculus
SEQUENCE: 81
TYNMH                                                                 5

SEQ ID NO: 82           moltype = AA   length = 17
FEATURE                 Location/Qualifiers
source                  1..17
                        mol_type = protein
                        organism = synthetic construct
SEQUENCE: 82
AIYPGSGDTS YNQKFKG                                                   17

SEQ ID NO: 83           moltype = AA   length = 11
FEATURE                 Location/Qualifiers
source                  1..11
                        mol_type = protein
                        organism = Mus musculus
SEQUENCE: 83
STIITTGAVD Y                                                         11
```

```
SEQ ID NO: 84              moltype = AA  length = 11
FEATURE                    Location/Qualifiers
source                     1..11
                           mol_type = protein
                           organism = Mus musculus
SEQUENCE: 84
KASQDVGTAV A                                                            11

SEQ ID NO: 85              moltype = AA  length = 7
FEATURE                    Location/Qualifiers
source                     1..7
                           mol_type = protein
                           organism = Mus musculus
SEQUENCE: 85
WTSTRHT                                                                 7

SEQ ID NO: 86              moltype = AA  length = 9
FEATURE                    Location/Qualifiers
source                     1..9
                           mol_type = protein
                           organism = Mus musculus
SEQUENCE: 86
QQYSRIPLT                                                               9

SEQ ID NO: 87              moltype = AA  length = 17
FEATURE                    Location/Qualifiers
source                     1..17
                           mol_type = protein
                           organism = Mus musculus
SEQUENCE: 87
AIYPGNGDTS YNQKFKG                                                      17

SEQ ID NO: 88              moltype = AA  length = 120
FEATURE                    Location/Qualifiers
source                     1..120
                           mol_type = protein
                           organism = synthetic construct
SEQUENCE: 88
QVQLVQSGAE VKKPGASVKV SCKASGYTFI TYNMHWVRQA PGQGLEWMGA IYPGSGDTSY        60
NQKFKGRVTM TRDTSTSTVY MELSSLRSED TAVYYCASST IITTGAVDYW GQGTLVTVSS        120

SEQ ID NO: 89              moltype = AA  length = 120
FEATURE                    Location/Qualifiers
source                     1..120
                           mol_type = protein
                           organism = synthetic construct
SEQUENCE: 89
QVQLVQSGAE VKKPGASVKV SCKTSGYTFI TYNMHWVRQA PGQGLEWIGA IYPGSGDTSY        60
NQKFKGRVTM TADTSTSTVY MELSSLRSED TAVYYCSIST IITTGAVDYW GQGTLVTVSS        120

SEQ ID NO: 90              moltype = AA  length = 120
FEATURE                    Location/Qualifiers
source                     1..120
                           mol_type = protein
                           organism = synthetic construct
SEQUENCE: 90
QVQLVQSGAE VVKPGASVKM SCKTSGYTFI TYNMHWVRQA PGQGLEWIGA IYPGSGDTSY        60
NQKFKGRVTL TADKSTSTAY MELSSLRSED TAVYYCSIST IITTGAVDYW GQGTLVTVSS        120

SEQ ID NO: 91              moltype = AA  length = 120
FEATURE                    Location/Qualifiers
source                     1..120
                           mol_type = protein
                           organism = synthetic construct
SEQUENCE: 91
QVQLQQSGAE VVKPGASVKM SCKTSGYTFI TYNMHWVKQA PGQGREWIGA IYPGSGDTSY        60
NQKFKGRATL TADKSTSTAY MELSSLRSED TAVYYCSIST IITTGAVDYW GQGTSVTVSS        120

SEQ ID NO: 92              moltype = AA  length = 107
FEATURE                    Location/Qualifiers
source                     1..107
                           mol_type = protein
                           organism = synthetic construct
SEQUENCE: 92
DIQMTQSPSS LSASVGDRVT ITCKASQDVG TAVAWYQQKP GKVPKLLIYW TSTRHTGVPS        60
RFSGSGSGTD FTLTISSLQP EDVATYYCQQ YSRIPLTFGG GTKVEIK                     107

SEQ ID NO: 93              moltype = AA  length = 107
FEATURE                    Location/Qualifiers
```

```
source                  1..107
                        mol_type = protein
                        organism = synthetic construct
SEQUENCE: 93
DIQMTQSPSS LSTSVGDRVT ITCKASQDVG TAVAWYQQKP GKSPKLLIYW TSTRHTGVPS    60
RFSGSGSGTD FTLIISSLQP EDVATYYCQQ YSRIPLTFGG GTKVEIK                 107

SEQ ID NO: 94           moltype = AA   length = 107
FEATURE                 Location/Qualifiers
source                  1..107
                        mol_type = protein
                        organism = synthetic construct
SEQUENCE: 94
DIQMTQSPSS LSTSVGDRVT ITCKASQDVG TAVAWYQQKP GQSPKLLIYW TSTRHTGVPD    60
RFSGSGSGTD FTLIIRSLQP EDVATYFCQQ YSRIPLTFGG GTKVEIK                 107

SEQ ID NO: 95           moltype = AA   length = 107
FEATURE                 Location/Qualifiers
source                  1..107
                        mol_type = protein
                        organism = synthetic construct
SEQUENCE: 95
DIVMTQSPSS LSTSVGDRVT ITCKASQDVG TAVAWYQQKP GQSPKLLIYW TSTRHTGVPD    60
RFTGSGSGTD FTLIIRSLQP EDVATYFCQQ YSRIPLTFGS GTKVEIK                 107

SEQ ID NO: 96           moltype = AA   length = 5
FEATURE                 Location/Qualifiers
source                  1..5
                        mol_type = protein
                        organism = Mus musculus
SEQUENCE: 96
EYIIH                                                                 5

SEQ ID NO: 97           moltype = AA   length = 17
FEATURE                 Location/Qualifiers
source                  1..17
                        mol_type = protein
                        organism = synthetic construct
SEQUENCE: 97
GIIPNNDVTN YKQNFRG                                                   17

SEQ ID NO: 98           moltype = AA   length = 11
FEATURE                 Location/Qualifiers
source                  1..11
                        mol_type = protein
                        organism = synthetic construct
SEQUENCE: 98
WRNAYYSAMD S                                                         11

SEQ ID NO: 99           moltype = AA   length = 11
FEATURE                 Location/Qualifiers
source                  1..11
                        mol_type = protein
                        organism = Mus musculus
SEQUENCE: 99
TASQDVGTAV A                                                         11

SEQ ID NO: 100          moltype = AA   length = 7
FEATURE                 Location/Qualifiers
source                  1..7
                        mol_type = protein
                        organism = Mus musculus
SEQUENCE: 100
WASTRHT                                                               7

SEQ ID NO: 101          moltype = AA   length = 9
FEATURE                 Location/Qualifiers
source                  1..9
                        mol_type = protein
                        organism = Mus musculus
SEQUENCE: 101
QQYRTSPLT                                                             9

SEQ ID NO: 102          moltype = AA   length = 17
FEATURE                 Location/Qualifiers
source                  1..17
                        mol_type = protein
                        organism = Mus musculus
SEQUENCE: 102
```

```
GIIPNNGVTN YKQNFRG                                                          17

SEQ ID NO: 103          moltype = AA   length = 11
FEATURE                 Location/Qualifiers
source                  1..11
                        mol_type = protein
                        organism = Mus musculus
SEQUENCE: 103
WRNGYYSAMD S                                                                11

SEQ ID NO: 104          moltype = AA   length = 120
FEATURE                 Location/Qualifiers
source                  1..120
                        mol_type = protein
                        organism = synthetic construct
SEQUENCE: 104
QVQLVQSGAE VKKPGSSVKV SCKASGFFFT EYIIHWVRQA PGQGLEWMGG IIPNNDVTNY            60
KQNFRGRVTI TADESTSTAY MELSSLRSED TAVYYCARWR NAYYSAMDSW GQGTTVTVSS           120

SEQ ID NO: 105          moltype = AA   length = 120
FEATURE                 Location/Qualifiers
source                  1..120
                        mol_type = protein
                        organism = synthetic construct
SEQUENCE: 105
QVQLVQSGAE VKKPGSSVKV SCKTSGFFFT EYIIHWVRQA PGQGLEWIGG IIPNNDVTNY            60
KQNFRGRVTL TADKSTSTAY MELSSLRSED TAVYYCARWR NAYYSAMDSW GQGTTVTVSS           120

SEQ ID NO: 106          moltype = AA   length = 120
FEATURE                 Location/Qualifiers
source                  1..120
                        mol_type = protein
                        organism = synthetic construct
SEQUENCE: 106
QVQLVQSGAE VVKPGSSVKV SCKTSGFFFT EYIIHWVRQS PGQGLEWIGG IIPNNDVTNY            60
KQNFRGRATL TADKSTSTAY MELSSLRSED TAVYYCARWR NAYYSAMDSW GQGTTVTVSS           120

SEQ ID NO: 107          moltype = AA   length = 121
FEATURE                 Location/Qualifiers
source                  1..121
                        mol_type = protein
                        organism = synthetic construct
SEQUENCE: 107
QVQLVQSGAE VVKPGSSVKI SCKTSGFFFT EYIIHWVKQS PGQGLEWIGG IIPNNDVTNY            60
KQNFRGRATL TADKSTNTAY MELRSSLRSE DTAVYYCARW RNAYYSAMDS WGQGTTVTVS           120
S                                                                          121

SEQ ID NO: 108          moltype = AA   length = 107
FEATURE                 Location/Qualifiers
source                  1..107
                        mol_type = protein
                        organism = synthetic construct
SEQUENCE: 108
DIQMTQSPSS LSASVGDRVT ITCTASQDVG TAVAWYQQKP GKVPKLLIYW ASTRHTGVPS            60
RFSGSGSGTD FTLTISSLQP EDVATYYCQQ YRTSPLTFGG GTKVEIK                        107

SEQ ID NO: 109          moltype = AA   length = 107
FEATURE                 Location/Qualifiers
source                  1..107
                        mol_type = protein
                        organism = synthetic construct
SEQUENCE: 109
DIQMTQSPSS LSTSVGDRVT ITCTASQDVG TAVAWYQQKP GKSPKLLIYW ASTRHTGVPE            60
RFSGSGSGTD FTLTISSLQP EDVATYFCQQ YRTSPLTFGG GTKVEIK                        107

SEQ ID NO: 110          moltype = AA   length = 107
FEATURE                 Location/Qualifiers
source                  1..107
                        mol_type = protein
                        organism = synthetic construct
SEQUENCE: 110
DIQVTQSPSS LSTSVGDRVT ITCTASQDVG TAVAWYQQKP GKSPKLLIYW ASTRHTGVPE            60
RFTGSGSGTD FTLTISSVQP EDVATYFCQQ YRTSPLTFGV GTKVEIK                        107

SEQ ID NO: 111          moltype = AA   length = 107
FEATURE                 Location/Qualifiers
source                  1..107
                        mol_type = protein
                        organism = synthetic construct
```

```
SEQUENCE: 111
DIVVTQSPSS LSTSVGDRVT ITCTASQDVG TAVAWYQQKP GKSPKLLIYW ASTRHTGVPE    60
RFTGSGSGTD FTLTISSVQP EDVATYFCQQ YRTSPLTFGV GTKLELK                107
```